(12) United States Patent
Dietz et al.

(10) Patent No.: US 10,358,426 B2
(45) Date of Patent: *Jul. 23, 2019

(54) FUNGICIDAL SUBSTITUTED 2-[2-HALOGENALKYL-4-(PHENOXY)-PHENYL]-1-[1,2,4]TRIAZOL-1-YL-ETHANOL COMPOUNDS

(71) Applicant: BASF Agro B.V., Arnhem (NL)

(72) Inventors: Jochen Dietz, Karlsruhe (DE); Richard Riggs, Mannheim (DE); Nadege Boudet, Hemsbach (DE); Jan Klaas Lohmann, Lambsheim (DE); Ian Robert Craig, Ludwigshafen (DE); Egon Haden, Speyer (DE); Erica May Cambeis, Mannheim (DE); Bernd Mueller, Frankenthal (DE); Wassilios Grammenos, Ludwigshafen (DE); Thomas Grote, Wachenheim (DE)

(73) Assignee: BASF Agro B.V., Arnhem (NL)

( * ) Notice: Subject to any disclaimer, the term of this patent is extended or adjusted under 35 U.S.C. 154(b) by 93 days.

This patent is subject to a terminal disclaimer.

(21) Appl. No.: 15/358,774

(22) Filed: Nov. 22, 2016

(65) Prior Publication Data

US 2017/0081296 A1    Mar. 23, 2017

Related U.S. Application Data

(63) Continuation of application No. 14/131,811, filed as application No. PCT/EP2012/063626 on Jul. 12, 2012.

(60) Provisional application No. 61/507,150, filed on Jul. 13, 2011.

(30) Foreign Application Priority Data

Jul. 13, 2011    (EP) .................................... 11173846

(51) Int. Cl.
| C07D 249/08 | (2006.01) |
| A01N 43/653 | (2006.01) |
| C07C 43/263 | (2006.01) |
| C07C 49/255 | (2006.01) |
| C07D 303/22 | (2006.01) |

(52) U.S. Cl.
CPC .......... *C07D 249/08* (2013.01); *A01N 43/653* (2013.01); *C07C 43/263* (2013.01); *C07C 49/255* (2013.01); *C07D 303/22* (2013.01)

(58) Field of Classification Search
None
See application file for complete search history.

(56) References Cited

U.S. PATENT DOCUMENTS

| 4,242,121 A | 12/1980 | Hawkins et al. |
| 4,599,362 A | 7/1986 | Nakatani et al. |
| 4,940,720 A | 7/1990 | Nevill et al. |
| 4,945,100 A | 7/1990 | Nyfeler et al. |
| 4,992,458 A | 2/1991 | Riebli et al. |
| 5,143,932 A | 9/1992 | Jautelat et al. |
| 5,162,358 A | 11/1992 | Jautelat et al. |
| 2008/0108686 A1 | 5/2008 | Gewehr et al. |
| 2009/0036509 A1 | 2/2009 | Gewehr et al. |
| 2009/0286768 A1 | 11/2009 | Crew et al. |
| 2014/0128255 A1 | 5/2014 | Dietz et al. |

FOREIGN PATENT DOCUMENTS

| AU | 611315 | 6/1991 |
| CA | 1100976 | 5/1981 |
| CA | 1209152 | 8/1986 |
| CN | 101225074 | 7/2008 |
| CS | 247 200 | 12/1986 |
| DE | 2 325 878 | 12/1974 |
| DE | 3801233 | 8/1988 |
| DE | 40 03 180 | 8/1991 |
| EP | 0 000 017 | 12/1978 |
| EP | 0113640 | 7/1984 |
| EP | 0 126 430 | 11/1984 |
| EP | 0 275 955 | 7/1988 |
| EP | 0 354 183 | 2/1990 |
| EP | 0 440 950 | 8/1991 |
| EP | 0 470 466 | 2/1992 |
| EP | 1 431 275 | 6/2004 |
| FR | 2 491 924 | 4/1982 |
| GB | 2 132 195 | 7/1984 |
| WO | WO 1996/041804 | 12/1996 |
| WO | WO 03 064572 | 8/2003 |
| WO | WO 2005/123689 | 12/2005 |
| WO | WO 2005/123690 | 12/2005 |
| WO | WO 2006/015866 | 2/2006 |
| WO | WO 2006/087373 | 8/2006 |
| WO | WO 2006/109933 | 10/2006 |

(Continued)

OTHER PUBLICATIONS

Yu et al., J. Agric. Food Chem., 2009, 57, 4854-4860.*
Office Action dated Jun. 23, 2015, issued in U.S. Appl. No. 14/237,463.
Office Action dated Jun. 12, 2015, issued in U.S. Appl. No. 14/237,048.
Office Action dated Jul. 27, 2015, issued in U.S. Appl. No. 14/237,041.
Office Action dated Dec. 10, 2014, issued in U.S. Appl. No. 14/237,463.

(Continued)

*Primary Examiner* — Alicia L Otton
(74) *Attorney, Agent, or Firm* — Brinks Gilson & Lione

(57) ABSTRACT

The present invention relates to substituted 2-[2-halogenalkyl-4-(phenoxy)-phenyl]-1-[1,2,4]triazol-1-yl-ethanol compounds of formula I as defined in the description, and the N-oxides, and salts thereof, their preparation and intermediates for preparing them. The invention also relates to the use of these compounds for combating harmful fungi and seed coated with at least one such compound and also to compositions comprising at least one such compound.

5 Claims, No Drawings

(56) References Cited

FOREIGN PATENT DOCUMENTS

| WO | WO 2006/119876 | | 11/2006 | | |
|---|---|---|---|---|---|
| WO | WO 2008/082198 | | 7/2008 | | |
| WO | WO 10/146114 | * | 12/2010 | ........... | C07D 405/06 |
| WO | WO 2010/146114 | | 12/2010 | | |
| WO | WO 2011/099804 | | 8/2011 | | |
| WO | WO 2012/037782 | | 3/2012 | | |
| WO | WO 2013/010862 | | 1/2013 | | |
| WO | WO 2013/010885 | | 1/2013 | | |
| WO | WO 2013/010894 | | 1/2013 | | |
| WO | WO 2013/024076 | | 1/2013 | | |
| WO | WO 2013/024077 | | 1/2013 | | |
| WO | WO 2013/024082 | | 1/2013 | | |
| WO | WO 2013007767 | | 1/2013 | | |
| WO | WO 2013/024075 | | 2/2013 | | |
| WO | WO 2013/024080 | | 2/2013 | | |
| WO | WO 2013/024081 | | 2/2013 | | |
| WO | WO 2013/024083 | | 2/2013 | | |

OTHER PUBLICATIONS

Office Action dated Dec. 1, 2014, issued in U.S. Appl. No. 14/232,434.
Office Action dated Dec. 8, 2014, issued in U.S. Appl. No. 14/232,462.
Office Action dated Dec. 8, 2014, issued in U.S. Appl. No. 14/237,048.
Lima, Lidia Moreira et al., "Bioisosterism: A useful strategy for molecular Modification and drug design", Current Medicinal Chemistry, 2005, p. 23-49, vol. 12.
Akama, Tsutomu, et al. "Discovery and structure-activity study of a novel benzoxaborole anti-inflammatory agent (AN2728) for the potential topical treatment of psoriasis and atopic dermatitis", Bioorganic & Medicinal Chemistry Letters, 2009, p. 2129-2132, vol. 19.
International Preliminary Report on Patentability, issued in PCT/EP2012/063626, dated Sep. 10, 2013.
International Search Report, issued in PCT/EP2012/063626, dated Oct. 9, 2012.
Yu et al., "Synthesis and Fungicidal Evaluation of 2-arylphenyl ether-3-(1H-1,2,4-triazol-1-yl)propan-2-ol Derivatives," Journal of Agricultural and Food Chemistry, vol. 57, No. 11, (2009), pp. 4854-4860.
Database CA [Online], Chemical Abstracts Service, Columbus, Ohio, US, Crew, et al., "Substituted imidazopyrazines and imidazotriazines as ACK1 inhibitors and their preparation" retrieved from STN Database accession No. 2009-1436665.
Database CA [Online], Chemical Abstracts Service, Columbus, Ohio, US, Schlafke, et al., "Phenoxy derivatives of trifluoromethylbenzene", retrieved from STN, Database accession No. 1975-170346.
Database CA [Online], Chemical Abstracts Service, Columbus, Ohio, US, Wan, et al., "Preparation of tricyclic compounds as Lp-PLA2 inhibitors", retrieved from STN, Database accession No. 2012-459740.

* cited by examiner

FUNGICIDAL SUBSTITUTED 2-[2-HALOGENALKYL-4-(PHENOXY)-PHENYL]-1-[1,2,4]TRIAZOL-1-YL-ETHANOL COMPOUNDS

CROSS REFERENCE TO RELATED APPLICATIONS

This application is a continuation of U.S. application Ser. No. 14/131,811, filed Jan. 9, 2014, the entire contents of which is hereby incorporated herein by reference. U.S. application Ser. No. 14/131,811, is a National Stage application of International Application No. PCT/EP2012/063626, filed Jul. 12, 2012, which claims the benefit of U.S. Provisional Application No. 61/507,150, filed Jul. 13, 2011, the entire contents of which are hereby incorporated herein by reference. U.S. application No. 14/131,811, also claims priority under 35 U.S.C. § 119 to European Patent Application No. 11173846.4, filed Jul. 13, 2011, the entire contents of which is hereby incorporated herein by reference.

The present invention relates to fungicidal substituted 2-[2-halogenalkyl-4-phenoxy-phenyl]-1-[1,2,4]triazol-1-yl-ethanol compounds and the N-oxides and the salts thereof for combating phytopathogenic fungi, and to the use and methods for combating phytopathogenic fungi and to seeds coated with at least one such compound. The invention also relates to processes for preparing these compounds, intermediates and to compositions comprising at least one compound I. The preparations of 2-[2-chloro-4-(4-chloro-phenoxy)-phenyl]-1-[1,2,4]triazol-1-yl-ethanol and certain derivatives thereof of formula

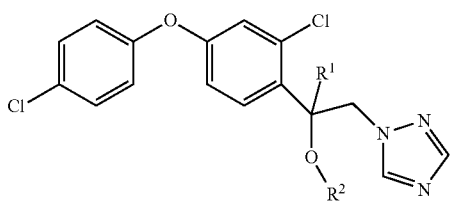

and their use for controlling phytopathogenic fungi is known from EP 0 275 955 A1; J. Agric. Food Chem. (2009) 57, 4854-4860; CN 101225074 A; DE 40 03 180 A1; EP 0 113 640 A2; EP 0 470 466 A2; U.S. Pat. No. 4,940,720 and EP 0 126 430 A2. The compounds according to the present invention differ from those described in the abovementioned publications inter alia by the replacement of the abovementioned 2-chloro group by the specific $C_1$-$C_2$-halogenalkyl substituent R as defined herein. DE 3801233 A1 relates to microbiocides of the formula

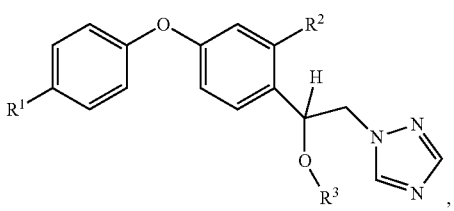

wherein $R^2$ is halogen.

Some intermediates can be found in DE 2325878, WO 2012/037782 A1, EP 1 431 275 A1, WO 2005/044780. WO 2010/146114 relates to triazole compounds carrying a sulfur substituent according to formulae I and II as defined in WO 2010/146114 and inter alia to intermediate compounds IV, their use as fungicides and production methods:

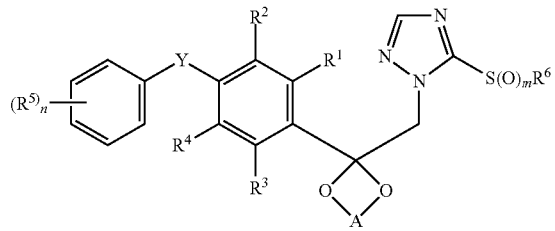

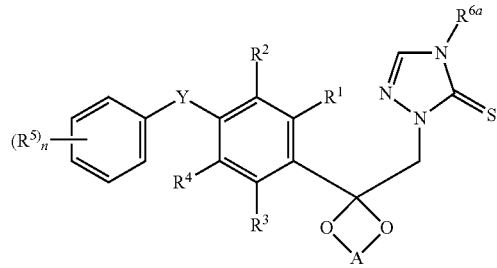

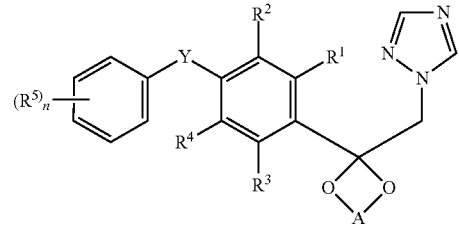

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

This object is achieved by the use of certain substituted 2-[2-halogenalkyl-4-phenoxy-phenyl]-1-[1,2,4]triazol-1-yl-ethanol compounds having good fungicidal activity against phytopathogenic harmful fungi.

Accordingly, the present invention relates to the compounds of formula I:

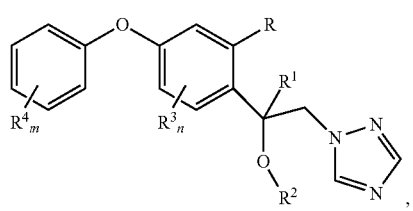

wherein:
R $C_1$-$C_2$-halogenalkyl;
$R^1$ hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl;
$R^2$ hydrogen, $C_1$-$C_6$-alkyl, $C_2$-$C_6$-alkenyl, $C_2$-$C_6$-alkynyl, $C_3$-$C_8$-cycloalkyl, phenyl, phenyl-$C_1$-$C_4$-alkyl, phenyl-$C_2$-$C_4$-alkenyl or phenyl-$C_2$-$C_4$-alkynyl;
wherein the aliphatic groups $R^1$ and/or $R^2$ may carry 1, 2, 3 or up to the maximum possible number of identical or different groups $R^a$ which independently of one another are selected from:

$R^a$ halogen, CN, nitro, $C_1$-$C_4$-alkoxy and $C_1$-$C_4$-halogenalkoxy;

wherein the cycloalkyl and/or phenyl moieties of $R^1$ and/or $R^2$ may carry 1, 2, 3, 4, 5 or up to the maximum number of identical or different groups $R^b$ which independently of one another are selected from:

$R^b$ halogen, CN, nitro, $C_1$-$C_4$-alkyl, $C_1$-$C_4$-alkoxy, $C_1$-$C_4$-halogenalkyl, $C_1$-$C_4$-halogenalkoxy;

$R^3$ is halogen, CN, nitro, $C_1$-$C_4$-alkyl, $C_1$-$C_4$-halogenalkyl, $C_1$-$C_4$-alkoxy or $C_1$-$C_4$-halogenalkoxy n is an integer and is 0, 1, 2 or 3;

$R^4$ is halogen, CN, nitro, $C_1$-$C_4$-alkyl, $C_1$-$C_4$-halogenalkyl, $C_1$-$C_4$-alkoxy or $C_1$-$C_4$-halogenalkoxy m is an integer and is 0, 1, 2, 3, 4 or 5;

and the N-oxides and the agriculturally acceptable salts thereof.

The term "compounds I" refers to compounds of formula I. Likewise, this terminology applies to all sub-formulae, e.g. "compounds I.A" refers to compounds of formula I.A or "compounds V" refers to compounds of formula V, etc.

The present invention furthermore relates to processes for preparing compounds of formula I.

The present invention furthermore relates to intermediates such as compounds of formulae IV, V, Va, VI, VII, IX, X and XI and the preparation thereof.

The compounds I can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2) and by the synthesis routes shown in the following schemes and in the experimental part of this application.

In a first process, for example, phenoles II are reacted, in a first step, with derivatives IIIb,

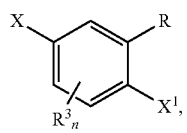

wherein $X^1$ stands for I or Br, in particular bromo derivatives III, preferably in the presence of a base. Thereafter, the resulting compounds IVa, in particular IV (wherein $X^1$ is Br) are then transformed into Grignard reagents by the reaction with transmetallation reagents such as isopropylmagnesium halides and subsequently reacted with acetyl chloride preferably under anhydrous conditions and preferably in the presence of a catalyst such as $CuCl_2$, $AlCl_3$, LiCl and mixtures thereof, to obtain acetophenones V. These compounds V can be halogenated e.g. with bromine preferably in an organic solvent such as diethyl ether, methyl tert.-butyl ether (MTBE), methanol or acetic acid. The resulting compounds VI, wherein "Hal" stands for "halogen" such as e.g. Br or Cl, can subsequently reacted with 1H-1,2,4-triazole preferably in the presence of a solvent such as tetrahydrofuran (THF), dimethylformamide (DMF), toluene and in the presence of a base such as potassium carbonate, sodium hydroxide or sodium hydride to obtain compounds VII. These triazole compounds VII can be reacted with a Grignard reagent such as $R^1$MgBr or an organo-lithium reagent $R^1$Li preferably under anhydrous conditions to obtain compounds I wherein $R^2$ is hydrogen, which compounds are of formula I.A. Optionally, a Lewis acid such as $LaCl_3 \cdot 2$ LiCl or $MgBr_2 \cdot xOEt_2$ can be used. If appropriate, these compounds I.A can subsequently be alkylated e.g. with $R^2$-LG, wherein LG represents a nucleophilically replaceable leaving group such as halogen, alkylsulfonyl, alkylsulfonyloxy and arylsulfonyloxy, preferably chloro, bromo or iodo, particularly preferably bromo, preferably in the presence of a base, such as for example, NaH in a suitable solvent such as THF, to form compounds I. The preparation of compounds I can be illustrated by the following scheme:

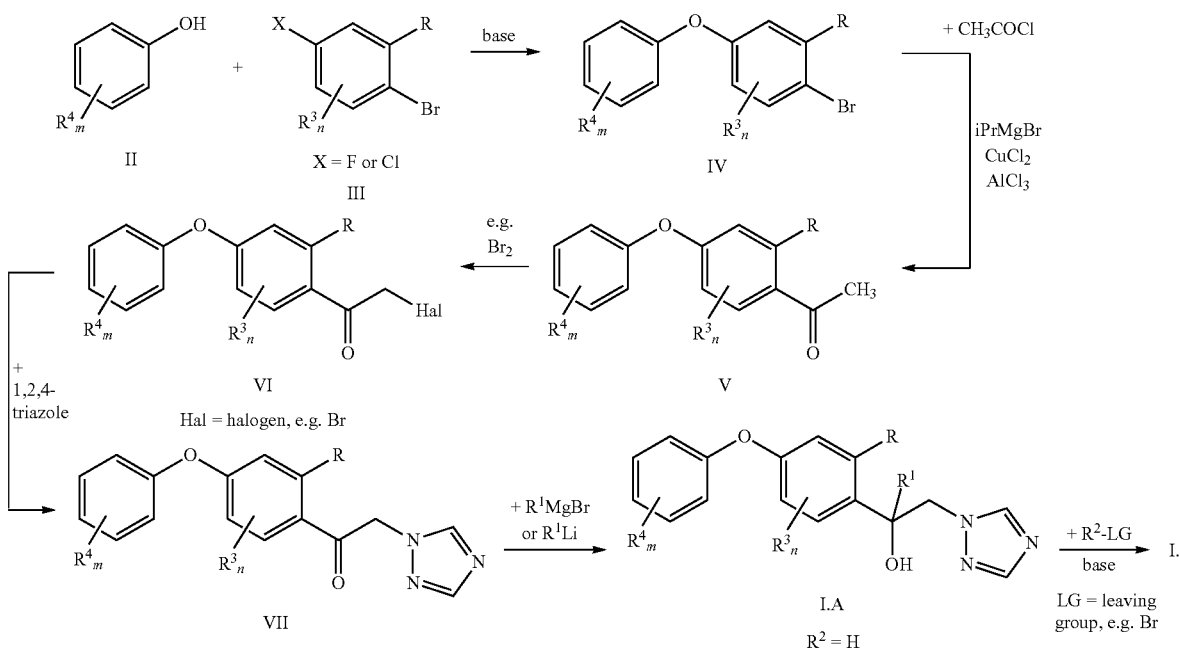

In a second process to obtain compounds I, bromo derivatives IIIa, in a first step, are reacted with e.g. isopropylmagnesium bromide followed by an acyl chloride agent R¹COCl (e.g. acetyl chloride) preferably under anhydrous conditions and optionally in the presence of a catalyst such as CuCl₂, AlCl₃, LiCl and mixtures thereof, to obtain ketones VIII. Thereafter, ketones VIII are reacted with phenoles II preferably in the presence of a base to obtain compounds Va wherein R¹ is as defined herein. Compounds Va may also be obtained in analogy to the first process described for compounds V. This is illustrated in the following scheme:

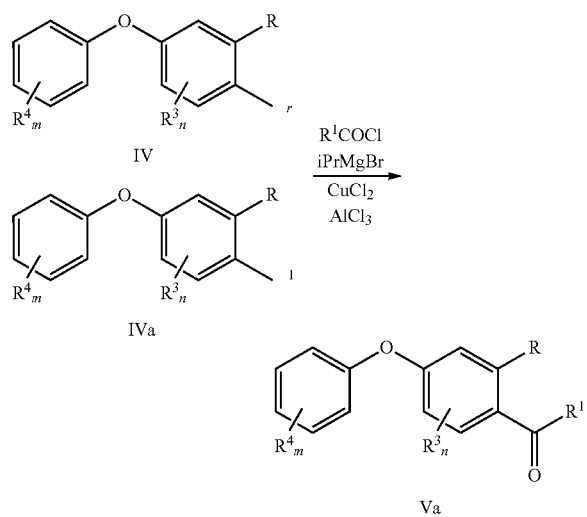

Thereafter, intermediates Va are reacted with trimethylsulf(ox)onium halides, preferably iodide, preferably in the presence of a base such as sodium hydroxide. Thereafter, the epoxides IX are reacted with 1H-1,2,4-triazole preferably in the presence of a base such as potassium carbonate and preferably in the presence of an organic solvent such as DMF to obtain compounds I.A which may be further derivatized as described above. The preparation of compounds I.A can be illustrated by the following scheme:

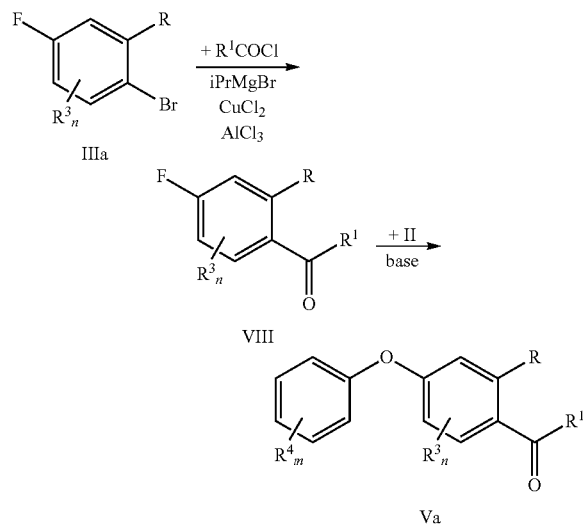

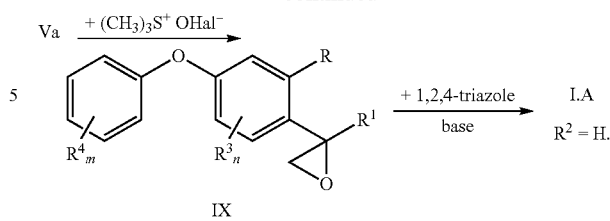

In a third process, the epoxide ring of intermediates IX is cleaved by reaction with alcohols R²OH preferably under acidic conditions. Thereafter, the resulting compounds X are reacted with halogenating agents or sulfonating agents such as PBr₃, PCl₃ mesyl chloride, tosyl chloride or thionyl chloride to obtain compounds XI wherein LG is a nucleophilically replaceable leaving group such as halogen, alkylsulfonyl, alkylsulfonyloxy and arylsulfonyloxy, preferably chloro, bromo or iodo, particularly preferably bromo or alkylsulfonyl. Then compounds XI are reacted with 1H-1,2,4-triazole to obtain compounds I. The preparation of compounds I can be illustrated by the following scheme:

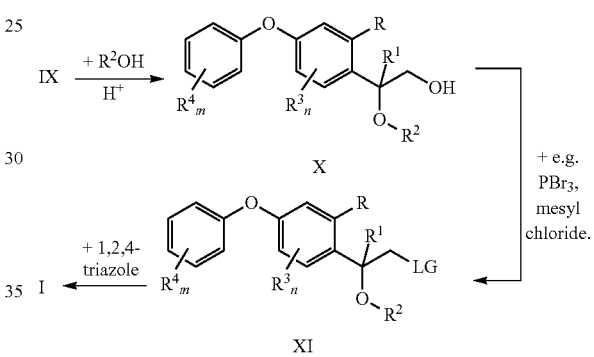

If individual compounds I cannot be obtained by the routes described above, they can be prepared by derivatization of other compounds I.

The N-oxides may be prepared from the compounds I according to conventional oxidation methods, e.g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e.g. under the action of light, acids or bases). Such conversions may also take place after use, e.g. in the treatment of plants in the treated plant, or in the harmful fungus to be controlled.

In the following, the intermediate compounds are further described. A skilled person will readily understand that the preferences for the substituents given herein in connection with compounds I apply for the intermediates accordingly. Thereby, the substituents in each case have independently of each other or more preferably in combination the meanings as defined herein.

Compounds of formula IVa and IV are partially new. Consequently, a further embodiment of the present invention are compounds of formula IVa and IV

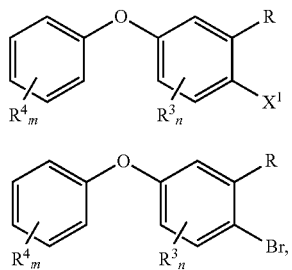

wherein the variables R, $R^3$, $R^4$, n and m are as defined and preferably defined for formula I herein, and wherein $X^1$ stands for I or Br, with the proviso that if $X^1$ is Br and R is $CF_3$ and n is 0, $R^4_m$ is not 4-Br, 3-$CF_3$, 4-F or 2-Cl and m is not 0.

According to one embodiment of formula IVa, $X^1$ is I. According to another embodiment of formula IVa, $X^1$ is Br, corresponding to formula IV, taking into account said proviso. According to a further embodiment, n is 0, with the said proviso.

According to one preferred embodiment, in compounds IV and IVa m is 1, 2 or 3 and at least one $R^4$ is at the para-position. According to a further preferred embodiment, in compounds IV and IVa m is 1, 2 or 3 and at least one $R^4$ is para-halogen, for example Cl or F, in particular Cl, with the said proviso. In particular, $R^4_m$ is 4-Cl.

In specific embodiments of compounds IV and IVa according to the present invention, the substituents R, $R^4$, $R^3$, m and n are as defined in tables 1 to 72, 73 to 237 and/or 73a to 237a for compounds I, taking into account the above proviso for compounds IV, wherein the substituents are specific embodiments independently of each other or in any combination.

A further embodiment of the present invention are compounds of formulae Va and V:

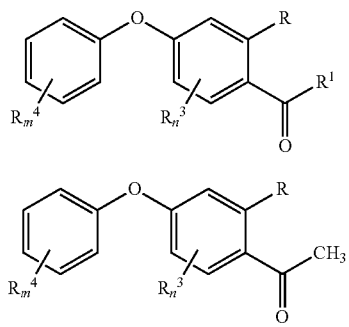

Wherein the variables R, $R^1$, $R^3$, $R^4$, n and m are as defined and preferably defined for formula I herein, with the proviso, that in formula Va, if $R^1$ is hydrogen and R is $CF_3$ and n=0, $R^4_m$ is not 3-$CF_3$ or 3-$CF_3$-4-Cl.

According to one preferred embodiment, in compounds V and Va m is 1 and $R^4$ is at the para-position.

According to a further preferred embodiment, in compounds IVa $R^1$ is not hydrogen, but selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl and phenyl-$C_2$-$C_4$-alkynyl.

In specific embodiments of compounds Va and V according to the present invention, the substituents R, $R^1$, R4, $R^3$, m and n are as defined in tables 1 to 72, 73 to 237 and/or 73a to 237a for compounds I, taking into account the above proviso for compounds Va, wherein the substituents are specific embodiments independently of each other or in any combination.

A further embodiment of the present invention are compounds of formula VI:

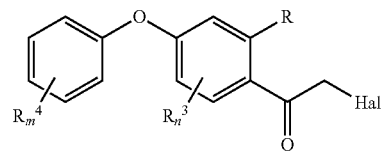

Wherein the variables R, $R^3$, $R^4$, n and m are as defined and preferably defined for formula I herein, and wherein Hal stands for halogen, in particular Cl or Br. According to one preferred embodiment, in compounds VI m is 1, 2 or 3 and at least one $R^4$ is at the para-position. In a specific embodiment, m is 1 and $R^4$ is at the para-position. According to another preferred embodiment, Hal in compounds VI stands for Br.

In specific embodiments of compounds VI according to the present invention, the substituents R, $R^4$, $R^3$, m and n are as defined in tables 1 to 72, 73 to 237 and/or 73a to 237a for compounds I, wherein the substituents are specific embodiments independently of each other or in any combination.

A further embodiment of the present invention are compounds of formula VII:

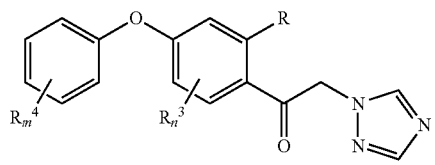

Wherein the variables R, $R^3$, $R^4$, n and m are as defined and preferably defined for formula I herein. In specific embodiments of compounds VII according to the present invention, the substituents R, $R^4$, $R^3$, m and n are as defined in tables 1 to 72, 73 to 237 and/or 73a to 237a for compounds I, wherein the substituents are specific embodiments independently of each other or in any combination.

A further embodiment of the present invention are compounds of formula IX:

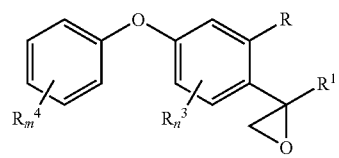

Wherein the variables R, $R^1$, $R^3$, $R^4$, n and m are as defined and preferably defined for formula I herein. According to one embodiment, in compounds IX $R^1$ is not hydrogen, but selected from $C_1$-$C_6$-alkyl, $C_2$-$C_6$-alkenyl, $C_2$-$C_6$- alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl and phenyl-$C_2$-$C_4$-alkynyl.

In specific embodiments of compounds IX according to the present invention, the substituents R, $R^1$, $R^4$, $R^3$, m and n are as defined in tables 1 to 72, 73 to 237 and/or 73a to 237a for compounds I, wherein the substituents are specific embodiments independently of each other or in any combination.

A further embodiment of the present invention are compounds of formula X:

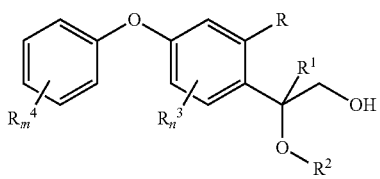

X

Wherein the variables R, $R^1$, $R^2$, $R^3$, $R^4$, n and m are as defined and preferably defined for formula I herein. According to one specific embodiment, in compounds X $R^1$ is not hydrogen, but selected from $C_1$-$C_6$-alkyl, $C_2$-$C_6$-alkenyl, $C_2$-$C_6$-alkynyl, $C_3$-$C_8$-cycloalkyl, phenyl, phenyl-$C_1$-$C_4$-alkyl, phenyl-$C_2$-$C_4$-alkenyl and phenyl-$C_2$-$C_4$-alkynyl.

In specific embodiments of compounds X according to the present invention, the substituents R, $R^1$, $R^2$, $R^4$, $R^3$, m and n are as defined in tables 1 to 72, 73 to 237 and/or 73a to 237a for compounds I, wherein the substituents are specific embodiments independently of each other or in any combination.

A further embodiment of the present invention are compounds of formula XI:

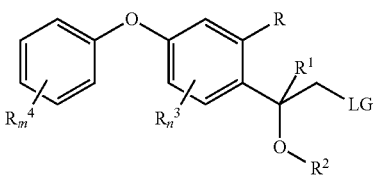

XI

Wherein the variables R, $R^1$, $R^2$, $R^3$, $R^4$, n and m are as defined and preferably defined for formula I herein, wherein LG stands for a leaving group as defined above. According to one embodiment, in compounds XI $R^1$ is not hydrogen, but selected from $C_1$-$C_6$-alkyl, $C_2$-$C_6$-alkenyl, $C_2$-$C_6$-alkynyl, $C_3$-$C_8$-cycloalkyl, phenyl, phenyl-$C_1$-$C_4$-alkyl, phenyl-$C_2$-$C_4$-alkenyl and phenyl-$C_2$-$C_4$-alkynyl.

In specific embodiments of compounds XI according to the present invention, the substituents R, $R^1$, $R^2$, $R^4$, $R^3$, m and n are as defined in tables 1 to 72, 73 to 237 and/or 73a to 237a for compounds I, wherein the substituents are specific embodiments independently of each other or in any combination.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_2$-haloalkyl" refers to an alkyl group having 1 or 2 carbon atoms, wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_1$-$C_6$-alkyl" refers to a straight-chained or branched saturated hydrocarbon group having 1 to 6 carbon atoms, e.g. methy, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_2$-$C_4$-alkenyl" refers to a straight-chain or branched unsaturated hydrocarbon radical having 2 to 4 carbon atoms and a double bond in any position, e.g. ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, prop-1-ynyl, prop-2-ynyl (propargyl), but-1-ynyl, but-2-ynyl, but-3-ynyl, 1-methyl-prop-2-ynyl. Likewise, the term "$C_2$-$C_6$-alkynyl" refers to a straight-chain or branched unsaturated hydrocarbon radical having 2 to 6 carbon atoms and at least one triple bond.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_4$-alkoxy" refers to a straight-chain or branched alkyl group having 1 to 4 carbon atoms which is bonded via an oxygen, at any position in the alkyl group, e.g. methoxy, ethoxy, n-propoxy, 1-methylethoxy, butoxy, 1-methyl propoxy, 2-methyl-propoxy or 1,1-dimethylethoxy.

The term "$C_1$-$C_4$-haloalkoxy" refers to a $C_1$-$C_4$-alkoxy radical as defined above, wherein some or all of the hydrogen atoms in these groups may be replaced by halogen atoms as mentioned above, e.g., $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-tri-fluoroethoxy, 2-chloro-2-fluoroethoxy, 2-chloro-2,2-difluoroethoxy, 2,2-dichloro-2-fluoroethoxy, 2,2,2-trichloro¬ethoxy, $OC_2F_5$, 2-fluoropropoxy, 3-fluoropropoxy, 2,2-difluoro-propoxy, 2,3-difluoro¬propoxy, 2 chloropropoxy, 3-chloropropoxy, 2,3-dichloropropoxy, 2-bromo¬propoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromo¬ethoxy, 4-fluorobutoxy, 4-chlorobutoxy, 4-bromobutoxy or nonafluorobutoxy.

The term "phenyl-$C_1$-$C_4$-alkyl" refers to alkyl having 1 to 4 carbon atoms (as defined above), wherein one hydrogen atom of the alkyl radical is replaced by a phenyl radical. Likewise, the terms "phenyl-$C_2$-$C_4$-alkenyl" and "phenyl-$C_2$-$C_4$-alkynyl" refer to alkenyl and alkynyl, respectively, wherein one hydrogen atom of the aforementioned radicals is replaced by a phenyl radical.

Agriculturally acceptable salts of compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl) sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

The compounds of formula I can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds I.

Preference is given to those compounds I and where applicable also to compounds of all sub-formulae such as I.1, I.A, I.B, I.C, I.A1, I.B1, I.C1 etc., provided herein and to the intermediates such as compounds IV, V, Va, VII, IX or XI, wherein the substituents (such as R, $R^1$, $R^2$, $R^3$, $R^4$, $R^a$, $R^b$, n and m) have independently of each other or more preferably in combination the following meanings:

One embodiment relates to compounds I, wherein R is $C_1$-halogenalkyl, more preferably selected from $CF_3$ and $CHF_2$, in particular $CF_3$.

According to one embodiment, $R^1$ is H.

According to a further embodiment of the invention, $R^1$ is selected from $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_2$-$C_4$-alkenyl and phenyl-$C_2$-$C_4$-alkynyl, wherein the aliphatic groups of $R^1$ are in each case unsubstituted or carry 1, 2, 3 or up to the maximum possible number of identical or different groups $R^a$, and the cycloalkyl and/or phenyl moieties of $R^1$ are in each case unsubstituted or carry 1, 2, 3, 4, 5 or up to the maximum number of identical or different groups $R^b$.

According to one embodiment, $R^1$ is $C_1$-$C_6$-alkyl. According to another embodiment, $R^1$ is $C_2$-$C_6$-alkenyl. According to still another embodiment, $R^1$ is $C_2$-$C_6$-alkynyl. According to a specific embodiment thereof, $R^1$ is C≡C—$CH_3$. According to still another embodiment, $R^1$ is $C_3$-$C_8$-cycloalkyl. According to still another embodiment, $R^1$ is $C_3$-$C_8$-cycloalkyl-$C_1$-$C_4$-alkyl. According to still another embodiment, $R^1$ is phenyl. According to still another embodiment, $R^1$ is phenyl-$C_1$-$C_4$-alkyl. In everyone of these embodiments, $R^1$ is unsubstituted or substituted by 1 to 3 $R^a$ selected from halogen, in particular F and Cl, $C_1$-$C_4$-alkoxy and CN and/or 1 to 3 $R^b$ selected from halogen, in particular Cl and F, $C_1$-$C_4$-alkoxy, $C_1$-$C_4$-alkyl and CN.

Another embodiment relates to compounds I, wherein $R^1$ is selected from hydrogen, $C_1$-$C_4$-alkyl, allyl, $C_2$-$C_6$-alkynyl, Cyclopropyl, phenyl, benzyl, phenylethenyl and phenylethinyl.

A further embodiment relates to compounds I, wherein $R^1$ is selected from $C_1$-$C_4$-alkyl, allyl, $C_2$-$C_6$-alkynyl, phenyl, benzyl, phenylethenyl and phenylethinyl, wherein the aforementioned groups carry 1, 2 or 3 halogen substituents, more preferably $R^1$ is $C_1$-$C_2$-haloalkyl, in particular $R^1$ is $CF_3$.

Particularly preferred embodiments of the invention relate to compounds I, wherein the $R^1$ is as defined in Table P below.

TABLE P

| line | $R^1$ |
|---|---|
| P-1 | H |
| P-2 | $CH_3$ |
| P-3 | $CH_2CH_3$ |
| P-4 | $CH_2CH_2CH_3$ |
| P-5 | $CH(CH_3)_2$ |
| P-6 | $C_3H_5$ (cyclopropyl) |
| P-7 | $C_6H_5$ |
| P-8 | $CH_2$—$C_6H_5$ |
| P-9 | $CF_3$ |
| P-10 | $CHF_2$ |
| P-11 | C≡CH |
| P-12 | C≡CCH$_3$ |
| P-13 | $CH_2CH_2CH_2CH_3$ |
| P-14 | $C(CH_3)_3$ |
| P-15 | $CH_2$—CH═$CH_2$ |
| P-16 | $CH_2$—CH═CH—$CH_3$ |
| P-17 | $CH_2$—C($CH_3$)═$CH_2$ |
| P-18 | CH═CHCH$_3$ |
| P-19 | C($CH_3$)═$CH_2$ |
| P-20 | CH═$CH_2$ |
| P-21 | cyclohexyl |
| P-22 | $C_5H_9$ (cyclopentyl) |
| P-23 | 4-Cl—$C_6H_4$ |
| P-24 | 4-$OCH_3$—$C_6H_4$ |
| P-25 | 4-$CH_3$—$C_6H_4$ |
| P-26 | 4-F—$C_6H_4$ |
| P-27 | 2,4-$F_2$—$C_6H_3$ |
| P-28 | 2,4-$Cl_2$—$C_6H_3$ |
| P-29 | $CH_2$—(4-Cl)—$C_6H_4$ |
| P-30 | $CH_2$—(4-$CH_3$)—$C_6H_4$ |
| P-31 | $CH_2$—(4-$OCH_3$)—$C_6H_4$ |

TABLE P-continued

| line | R$^1$ |
|---|---|
| P-32 | CH$_2$—(4-F)—C$_6$H$_4$ |
| P-33 | CH$_2$—(2,4-Cl$_2$)—C$_6$H$_3$ |
| P-34 | CH$_2$—(2,4-F$_2$)—C$_6$H$_3$ |
| P-35 | CH(CH$_3$)CH$_2$CH$_3$ |
| P-36 | CH$_2$—CH(CH$_3$)$_2$ |
| P-37 | CH$_2$—C≡C—CH$_3$ |
| P-38 | CH$_2$—C≡C—H |
| P-39 | CH$_2$—C≡C—CH$_2$CH$_3$ |
| P-40 | CH(CH$_3$)—C$_3$H$_5$ (CH(CH$_3$)-Cyclopropyl) |
| P-41 | CH$_2$—C$_3$H$_5$ (CH$_2$-cyclopropyl) |
| P-42 | 1-(Cl)-cyclopropyl |
| P-43 | 1-(CH$_3$)-cyclopropyl |
| P-44 | 1-(CN)-cyclopropyl |
| P-45 | CH(CH$_3$)—CN |
| P-46 | CH$_2$—CH$_2$—CN |
| P-47 | CH$_2$—OCH$_3$ |
| P-48 | CH$_2$—OCH$_2$CH$_3$ |
| P-49 | CH(CH$_3$)—OCH$_3$ |
| P-50 | CH(CH$_3$)—OCH$_2$CH$_3$ |

According to one embodiment, R$^2$ is hydrogen.

According to a further embodiment, R$^2$ is selected from C$_1$-C$_6$-alkyl, C$_2$-C$_6$-alkenyl, C$_2$-C$_6$-alkynyl, phenyl and phenyl-C$_1$-C$_4$-alkyl, wherein the aliphatic groups of R$^2$ are in each case unsubstituted or carry 1, 2, 3 or up to the maximum possible number of identical or different groups R$^a$, and the cycloalkyl and/or phenyl moieties of R$^2$ are in each case unsubstituted or carry 1, 2, 3, 4, 5 or up to the maximum number of identical or different groups R$^b$.

According to one specific embodiment, R$^2$ is C$_1$-C$_6$-alkyl. According to one further specific embodiment, R$^2$ is C$_2$-C$_6$-alkenyl, in particular allyl. According to one further specific embodiment, R$^2$ is C$_2$-C$_6$-alkynyl, in particular —CH$_2$—C≡CH or —CH$_2$—C≡C—CH$_3$. According to one further specific embodiment, R$^2$ is phenyl. According to one further specific embodiment, R$^2$ is phenyl-C$_1$-C$_4$-alkyl, in particular benzyl. In everyone of these embodiments, R$^2$ is unsubstituted or substituted by 1 to 3 R$^a$ selected from halogen, in particular F and Cl, C$_1$-C$_4$-alkoxy and/or 1 to 3 R$^b$ selected from halogen, in particular Cl and F, C$_1$-C$_4$-alkoxy and C$_1$-C$_4$-alkyl. One specific embodiment further relates to compounds wherein R$^2$ is C$_1$-C$_4$-alkoxy-C$_1$-C$_6$-alkyl.

A further embodiment relates to compounds I, wherein R$^2$ is selected from hydrogen, C$_1$-C$_4$-alkyl, allyl, propargyl (—CH$_2$—C≡C—H) and benzyl, in particular R$^2$ is hydrogen, which compounds are of formula I.A.

A further embodiment relates to compounds I, wherein R$^2$ is methyl which compounds are of formula I.B:

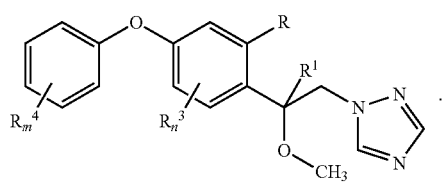

I.B

A further embodiment relates to compounds I, wherein R$^2$ is ethyl which compounds are of formula I.C:

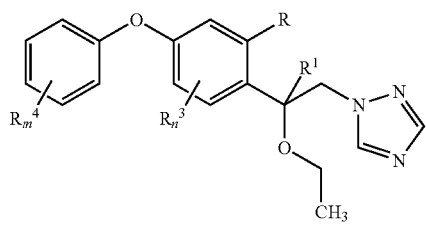

I.C

A further embodiment relates to compounds I, wherein R$^2$ is isopropyl which compounds are of formula I.D and still a further embodiment relates to compounds I, wherein R$^2$ is benzyl which compounds are of formula I.E:

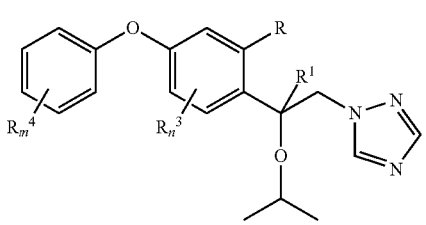

I.D

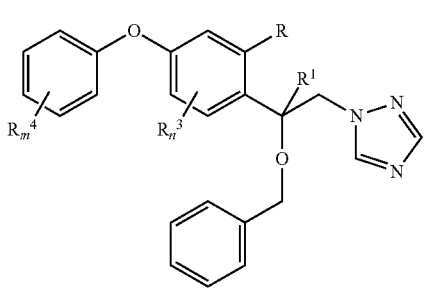

I.E

A further embodiment relates to compounds I, wherein R$^2$ is 4-Cl-benzyl which compounds are of formula I.F and still a further embodiment relates to compounds I, wherein R$^2$ is 4-F-benzyl which compounds are of formula I.G:

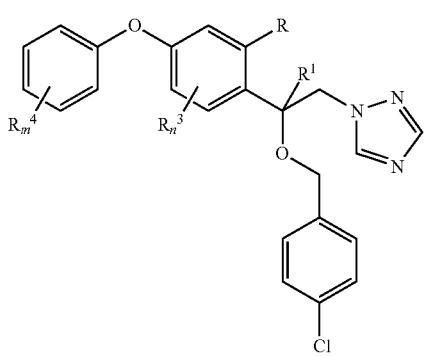

I.F

I.G

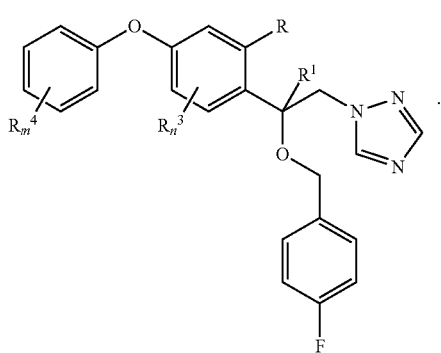

A further embodiment relates to compounds I, wherein $R^2$ is 4-$CH_3$-benzyl which compounds are of formula I.H, and still a further embodiment relates to compounds I, wherein $R^2$ is 4-$OCH_3$-benzyl which compounds are of formula I.J:

I.H

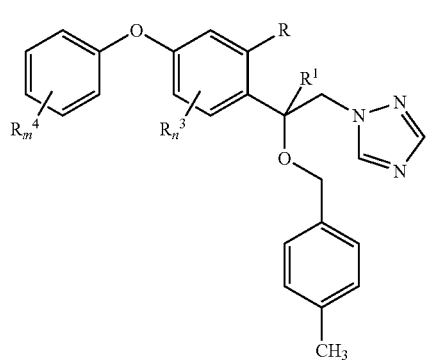

I.J

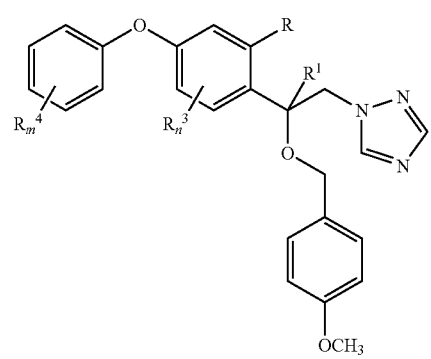

A further embodiment relates to compounds I, wherein $R^2$ is $CH_2$—$OCH_3$ which compounds are of formula I.K, and still a further embodiment relates to compounds I, wherein $R^2$ is allyl which compounds are of formula I.L:

I.K

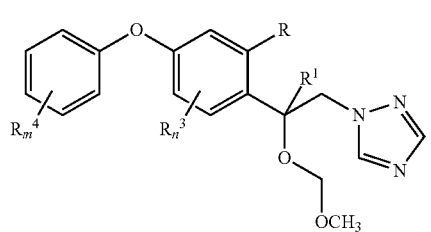

I.L

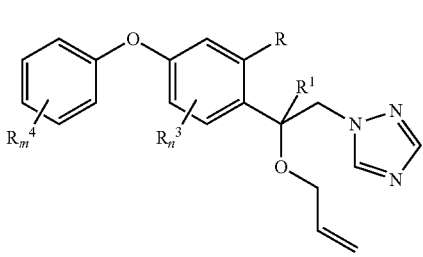

A further embodiment relates to compounds I, wherein $R^2$ is n-propyl which compounds are of formula I.M, and still a further embodiment relates to compounds I, wherein $R^2$ is propargyl which compounds are of formula I.N:

I.M

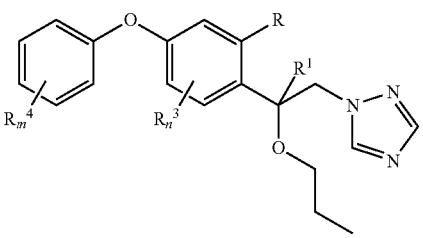

I.N

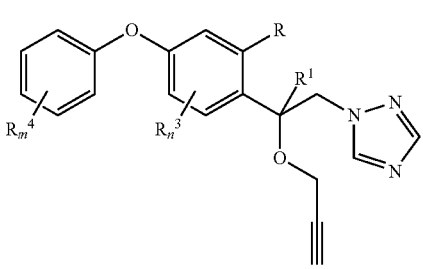

A further embodiment relates to compounds I, wherein $R^2$ is $CH_3$-propargyl which compounds are of formula I.O, and still a further embodiment relates to compounds I, wherein $R^2$ is $CH_2C(CH_3)$=$CH_2$ which compounds are of formula I.P:

I.O

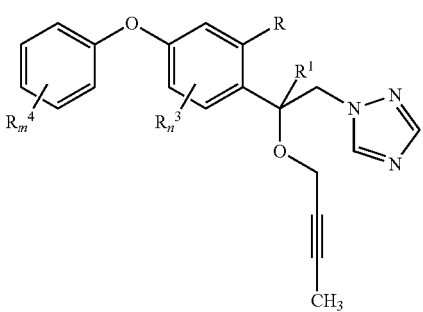

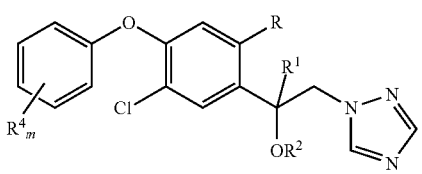

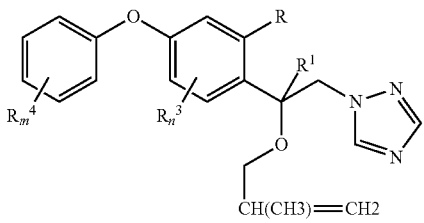

A further embodiment relates to compounds I, wherein n is 0, which compounds are of formula I.1:

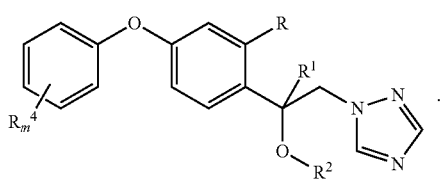

A further embodiment relates to compounds I, wherein $R^3{}_n$ is ortho-Br (ortho in relation to the linkage of the alcohol group to the phenyl ring), which compounds are of formula I.6. Still a further embodiment relates to compounds I, wherein $R^3{}_n$ is meta-Br (meta in relation to the linkage of the alcohol group to the phenyl ring), which compounds are of formula I.7:

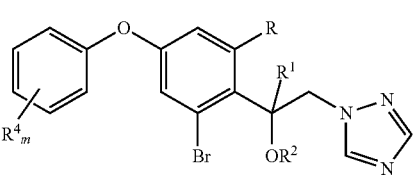

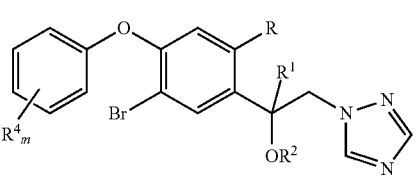

A further embodiment relates to compounds I, wherein $R^3{}_n$ is ortho-CH$_3$ (ortho in relation to the linkage of the alcohol group to the phenyl ring), which compounds are of formula I.2. Still a further embodiment relates to compounds I, wherein $R^3{}_n$ is meta-CH$_3$ (meta in relation to the linkage of the alcohol group to the phenyl ring), which compounds are of formula I.3:

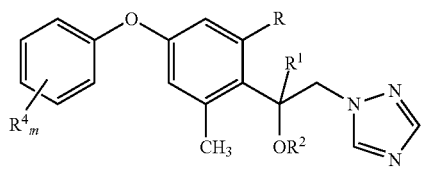

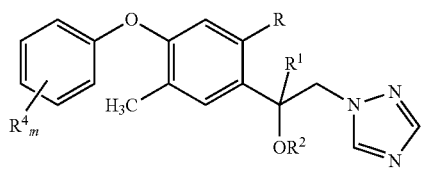

A further embodiment relates to compounds I, wherein $R^3{}_n$ is ortho-F (ortho in relation to the linkage of the alcohol group to the phenyl ring), which compounds are of formula I.8. Still a further embodiment relates to compounds I, wherein $R^3{}_n$ is meta-F (meta in relation to the linkage of the alcohol group to the phenyl ring), which compounds are of formula I.9:

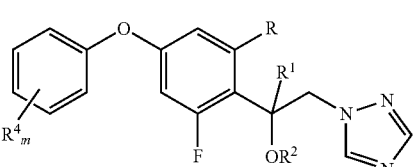

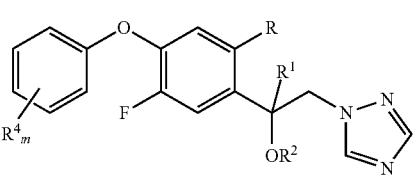

A further embodiment relates to compounds I, wherein $R^3{}_n$ is ortho-Cl (ortho in relation to the linkage of the alcohol group to the phenyl ring), which compounds are of formula I.4. Still a further embodiment relates to compounds I, wherein $R^3{}_n$ is meta-Cl (meta in relation to the linkage of the alcohol group to the phenyl ring), which compounds are of formula I.5:

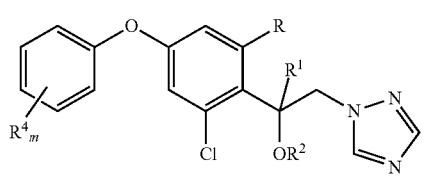

A further embodiment relates to compounds I, wherein $R^3{}_n$ is ortho-OCH$_3$ (ortho in relation to the linkage of the alcohol group to the phenyl ring), which compounds are of formula I.10. Still a further embodiment relates to compounds I, wherein $R^3{}_n$ is meta-OCH$_3$ (meta in relation to the linkage of the alcohol group to the phenyl ring), which compounds are of formula I.11:

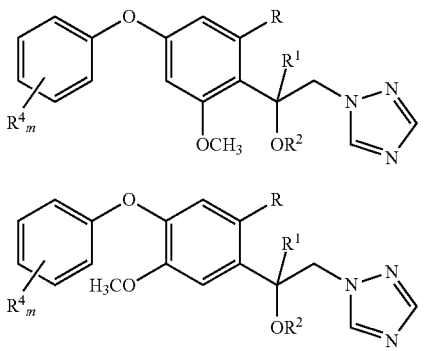

Further embodiment relates to compounds I, wherein n is 0 and $R^2$ is hydrogen, methyl or ethyl, which compounds are of formulae I.A1, I.B1 and I.C1, respectively:

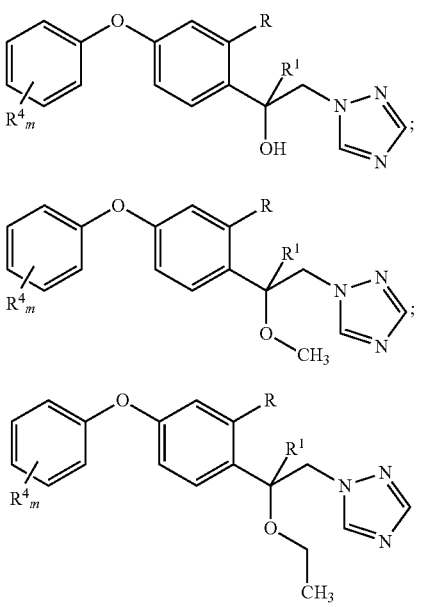

A further embodiment relates to compounds I, wherein n is 1, 2, or 3.

A further embodiment relates to compounds I, wherein $R^3$ is halogen, in particular selected from F and Cl. According to a further embodiment, $R^3$ is $C_1$-$C_4$-alkyl, in particular $CH_3$. According to a further embodiment, $R^3$ is $C_1$-$C_4$-alkoxy, in particular $OCH_3$. According to still a further embodiment, $R^3$ is independently selected from halogen, $C_1$-$C_4$-alkyl and $C_1$-$C_4$-alkoxy.

A further embodiment relates to compounds I, wherein m is 0 or 1. According to one embodiment, m is 1. According to one specific embodiment thereof, said $R^4$ is in the 4-position of the phenyl ring.

According to a further embodiment, $R^4$ is $C_1$-$C_4$-alkyl.

According to still a further embodiment, $R^4$ is $C_1$-$C_4$-haloalkyl.

According to a further embodiment, $R^4$ is $C_1$-$C_4$-alkoxy.

According to a further embodiment, $R^4$ is $C_1$-$C_4$-haloalkoxy.

A further embodiment relates to compounds I, wherein m is 1, 2 or 3.

A further embodiment relates to compounds I, wherein $R^4$ is halogen, in particular selected from F and Cl. A further embodiment relates to compounds I, wherein $R^4_m$ is selected from 4-Cl, 2-F, 4-F, 2,4-$Cl_2$, 2,4-$F_2$, 2-F-4-Cl, 2,4,6-$Cl_3$ and 2,6-$F_2$-4-Cl.

A skilled person will readily understand that the preferences given in connection with compounds I apply for the intermediates accordingly, in particular for formulae IV, IVa, V, Va, VI, VII, IX, and XI as defined above.

With respect to their use, according to one embodiment of the invention, particular preference is given to the compounds of formulae I.A1, I.B1 and I.C1 compiled in tables 1 to 72 below. Here, the groups mentioned in the Tables for a substituent are furthermore, independently of the combination wherein they are mentioned, a particularly preferred embodiment of the substituent in question.

Table 1: Compounds 1 to 125 of formula I.A1, wherein $R^1$ is defined as in line P-1 of table P, R is $CF_3$ and the meaning of $R^4_m$ for each individual compound corresponds in each case to one line of table A.

Table 2: Compounds 126 to 250 of formula I.A1, wherein $R^1$ is defined as in line P-2 of table P, R is $CF_3$ and the meaning of $R^4_m$ for each individual compound corresponds in each case to one line of table A.

Table 3: Compounds 251 to 375 of formula I.A1, wherein $R^1$ is defined as in line P-3 of table P, R is $CF_3$ and the meaning of $R^4_m$ for each individual compound corresponds in each case to one line of table A.

Table 4: Compounds 376 to 500 of formula I.A1, wherein $R^1$ is defined as in line P-4 of table P, R is $CF_3$ and the meaning of $R^4_m$ for each individual compound corresponds in each case to one line of table A.

Table 5: Compounds 501 to 625 of formula I.A1, wherein $R^1$ is defined as in line P-5 of table P, R is $CF_3$ and the meaning of $R^4_m$ for each individual compound corresponds in each case to one line of table A.

Table 6: Compounds 626 to 750 of formula I.A1, wherein $R^1$ is defined as in line P-6 of table P, R is $CF_3$ and the meaning of $R^4_m$ for each individual compound corresponds in each case to one line of table A.

Table 7: Compounds 751 to 875 of formula I.A1, wherein $R^1$ is defined as in line P-7 of table P, R is $CF_3$ and the meaning of $R^4_m$ for each individual compound corresponds in each case to one line of table A.

Table 8: Compounds 876 to 1000 of formula I.A1, wherein $R^1$ is defined as in line P-8 of table P, R is $CF_3$ and the meaning of $R^4_m$ for each individual compound corresponds in each case to one line of table A.

Table 9: Compounds 1001 to 1125 of formula I.A1, wherein $R^1$ is defined as in line P-9 of table P, R is $CF_3$ and the meaning of $R^4_m$ for each individual compound corresponds in each case to one line of table A.

Table 10: Compounds 1126 to 1250 of formula I.A1, wherein $R^1$ is defined as in line P-10 of table P, R is $CF_3$ and the meaning of $R^4_m$ for each individual compound corresponds in each case to one line of table A.

Table 11: Compounds 1251 to 1375 of formula I.A1, wherein $R^1$ is defined as in line P-11 of table P, R is $CF_3$ and the meaning of $R^4_m$ for each individual compound corresponds in each case to one line of table A.

Table 12: Compounds 1376 to 1500 of formula I.A1, wherein $R^1$ is defined as in line P-12 of table P, R is $CF_3$ and the meaning of $R^4_m$ for each individual compound corresponds in each case to one line of table A.

Tables 13 to 24: Compounds 1501 to 3000 of formula I.A1, wherein $R^1$ is defined as in Tables 1 to 12 and R is $CHF_2$ instead of $CF_3$ and the meaning of $R^4{}_m$ for each individual compound corresponds in each case to one line of table A. Consequently, this corresponds to:

Table 13 Compounds 1501 to 1625 of formula I.A1, wherein $R^1$ is defined as in line P-1 of table P, R is $CHF_2$ and the meaning of $R^4{}_m$ for each individual compound corresponds in each case to one line of table A Table 14 Compounds 1626 to 1750 of formula I.A1, wherein $R^1$ is defined as in line P-2 of table P, R is $CHF_2$ and the meaning of $R^4{}_m$ for each individual compound corresponds in each case to one line of table A Table 15 Compounds 1751 to 1875 of formula I.A1, wherein $R^1$ is defined as in line P-3 of table P, R is $CHF_2$ and the meaning of $R^4{}_m$ for each individual compound corresponds in each case to one line of table A Table 16 Compounds 1876 to 2000 of formula I.A1, wherein $R^1$ is defined as in line P-4 of table P, R is $CHF_2$ and the meaning of $R^4{}_m$ for each individual compound corresponds in each case to one line of table A Table 17 Compounds 2001 to 2125 of formula I.A1, wherein $R^1$ is defined as in line P-5 of table P, R is $CHF_2$ and the meaning of $R^4{}_m$ for each individual compound corresponds in each case to one line of table A Table 18 Compounds 2126 to 2250 of formula I.A1, wherein $R^1$ is defined as in line P-6 of table P, R is $CHF_2$ and the meaning of $R^4{}_m$ for each individual compound corresponds in each case to one line of table A Table 19 Compounds 2251 to 2375 of formula I.A1, wherein $R^1$ is defined as in line P-7 of table P, R is $CHF_2$ and the meaning of $R^4{}_m$ for each individual compound corresponds in each case to one line of table A Table 20 Compounds 2376 to 2500 of formula I.A1, wherein $R^1$ is defined as in line P-8 of table P, R is $CHF_2$ and the meaning of $R^4{}_m$ for each individual compound corresponds in each case to one line of table A Table 21 Compounds 2501 to 2625 of formula I.A1, wherein $R^1$ is defined as in line P-9 of table P, R is $CHF_2$ and the meaning of $R^4{}_m$ for each individual compound corresponds in each case to one line of table A Table 22 Compounds 2626 to 2750 of formula I.A1, wherein $R^1$ is defined as in line P-10 of table P, R is $CHF_2$ and the meaning of $R^4{}_m$ for each individual compound corresponds in each case to one line of table A Table 23 Compounds 2751 to 2875 of formula I.A1, wherein $R^1$ is defined as in line P-11 of table P, R is $CHF_2$ and the meaning of $R^4{}_m$ for each individual compound corresponds in each case to one line of table A Table 24 Compounds 2876 to 3000 of formula I.A1, wherein $R^1$ is defined as in line P-12 of table P, R is $CHF_2$ and the meaning of $R^4{}_m$ for each individual compound corresponds in each case to one line of table A Tables 25 to 48: Compounds 3001 to 6000 of formula I.B1, wherein R and $R^1$ are defined as in Tables 1 to 24 and the meaning of $R^4{}_m$ for each individual compound corresponds in each case to one line of table A. Consequently, this corresponds to:

Table 25 Compounds 3001 to 3125 of formula I.B1, wherein $R^1$ is defined as in line P-1 of table P, R is $CF_3$ and the meaning of $R^4{}_m$ for each individual compound corresponds in each case to one line of table A Table 26 Compounds 3126 to 3250 of formula I.B1, wherein $R^1$ is defined as in line P-2 of table P, R is $CF_3$ and the meaning of $R^4{}_m$ for each individual compound corresponds in each case to one line of table A Table 27 Compounds 3251 to 3375 of formula I.B1, wherein $R^1$ is defined as in line P-3 of table P, R is $CF_3$ and the meaning of $R^4{}_m$ for each individual compound corresponds in each case to one line of table A Table 28 Compounds 3376 to 3500 of formula I.B1, wherein $R^1$ is defined as in line P-4 of table P, R is $CF_3$ and the meaning of $R^4{}_m$ for each individual compound corresponds in each case to one line of table A Table 29 Compounds 3501 to 3625 of formula I.B1, wherein $R^1$ is defined as in line P-5 of table P, R is $CF_3$ and the meaning of $R^4{}_m$ for each individual compound corresponds in each case to one line of table A Table 30 Compounds 3626 to 3750 of formula I.B1, wherein $R^1$ is defined as in line P-6 of table P, R is $CF_3$ and the meaning of $R^4{}_m$ for each individual compound corresponds in each case to one line of table A Table 31 Compounds 3751 to 3875 of formula I.B1, wherein $R^1$ is defined as in line P-7 of table P, R is $CF_3$ and the meaning of $R^4{}_m$ for each individual compound corresponds in each case to one line of table A Table 32 Compounds 3876 to 4000 of formula I.B1, wherein $R^1$ is defined as in line P-8 of table P, R is $CF_3$ and the meaning of $R^4{}_m$ for each individual compound corresponds in each case to one line of table A Table 33 Compounds 4001 to 4125 of formula I.B1, wherein $R^1$ is defined as in line P-9 of table P, R is $CF_3$ and the meaning of $R^4{}_m$ for each individual compound corresponds in each case to one line of table A Table 34 Compounds 4126 to 4250 of formula I.B1, wherein $R^1$ is defined as in line P-10 of table P, R is $CF_3$ and the meaning of $R^4{}_m$ for each individual compound corresponds in each case to one line of table A Table 35 Compounds 4251 to 4375 of formula I.B1, wherein $R^1$ is defined as in line P-11 of table P, R is $CF_3$ and the meaning of $R^4{}_m$ for each individual compound corresponds in each case to one line of table A Table 36 Compounds 4376 to 4500 of formula I.B1, wherein $R^1$ is defined as in line P-12 of table P, R is $CF_3$ and the meaning of $R^4{}_m$ for each individual compound corresponds in each case to one line of table A Table 37 Compounds 4501 to 4625 of formula I.B1, wherein $R^1$ is defined as in line P-1 of table P, R is $CHF_2$ and the meaning of $R^4{}_m$ for each individual compound corresponds in each case to one line of table A Table 38 Compounds 4626 to 4750 of formula I.B1, wherein $R^1$ is defined as in line P-2 of table P, R is $CHF_2$ and the meaning of $R^4{}_m$ for each individual compound corresponds in each case to one line of table A Table 39 Compounds 4751 to 4875 of formula I.B1, wherein $R^1$ is defined as in line P-3 of table P, R is $CHF_2$ and the meaning of $R^4{}_m$ for each individual compound corresponds in each case to one line of table A Table 40 Compounds 4876 to 5000 of formula I.B1, wherein $R^1$ is defined as in line P-4 of table P, R is $CHF_2$ and the meaning of $R^4{}_m$ for each individual compound corresponds in each case to one line of table A Table 41 Compounds 5001 to 5125 of formula I.B1, wherein $R^1$ is defined as in line P-5 of table P, R is $CHF_2$ and the meaning of $R^4{}_m$ for each individual compound corresponds in each case to one line of table A Table 42 Compounds 5126 to 5250 of formula I.B1, wherein $R^1$ is defined as in line P-6 of table P, R is $CHF_2$ and the meaning of $R^4{}_m$ for each individual compound corresponds in each case to one line of table A Table 43 Compounds 5251 to 5375 of formula I.B1, wherein $R^1$ is defined as in line P-7 of table P, R is $CHF_2$ and the meaning of $R^4{}_m$ for each individual compound corresponds in each case to one line of table A Table 44 Compounds 5376 to 5500 of formula I.B1, wherein $R^1$ is defined as in line P-8 of table P, R is $CHF_2$ and the meaning of $R^4_m$ for each individual compound corresponds in each case to one line of table A Table 45 Compounds 5501 to 5625 of formula I.B1, wherein $R^1$ is defined as in line P-9 of table P, R is $CHF_2$ and the meaning of $R^4_m$ for each individual compound corresponds in each case to one line of table A Table 46 Compounds 5626 to 5750 of formula I.B1, wherein $R^1$ is defined as in line P-10 of table P, R is $CHF_2$ and the meaning of $R^4_m$ for each individual compound corresponds in each case to one line of table A Table 47 Compounds 5751 to 5875 of formula I.B1, wherein $R^1$ is defined as in line P-11 of table P, R is $CHF_2$ and the meaning of $R^4_m$ for each individual compound corresponds in each case to one line of table A Table 48 Compounds 5876 to 6000 of formula I.B1, wherein $R^1$ is defined as in line P-12 of table P, R is $CHF_2$ and the meaning of $R^4_m$ for each individual compound corresponds in each case to one line of table A Tables 49 to 72: Compounds 6001 to 9000 of formula I.C1, wherein R and $R^1$ are defined as in Tables 1 to 24 and the meaning of $R^4_m$ for each individual compound corresponds in each case to one line of table A.

Consequently, this corresponds to:

Table 49 Compounds 6001 to 6125 of formula I.C1, wherein $R^1$ is defined as in line P-1 of table P, R is $CF_3$ and the meaning of $R^4_m$ for each individual compound corresponds in each case to one line of table A Table 50 Compounds 6126 to 6250 of formula I.C1, wherein $R^1$ is defined as in line P-2 of table P, R is $CF_3$ and the meaning of $R^4_m$ for each individual compound corresponds in each case to one line of table A Table 51 Compounds 6251 to 6375 of formula I.C1, wherein $R^1$ is defined as in line P-3 of table P, R is $CF_3$ and the meaning of $R^4_m$ for each individual compound corresponds in each case to one line of table A Table 52 Compounds 6376 to 6500 of formula I.C1, wherein $R^1$ is defined as in line P-4 of table P, R is $CF_3$ and the meaning of $R^4_m$ for each individual compound corresponds in each case to one line of table A Table 53 Compounds 6501 to 6625 of formula I.C1, wherein $R^1$ is defined as in line P-5 of table P, R is $CF_3$ and the meaning of $R^4_m$ for each individual compound corresponds in each case to one line of table A Table 54 Compounds 6626 to 6750 of formula I.C1, wherein $R^1$ is defined as in line P-6 of table P, R is $CF_3$ and the meaning of $R^4_m$ for each individual compound corresponds in each case to one line of table A Table 55 Compounds 6751 to 6875 of formula I.C1, wherein $R^1$ is defined as in line P-7 of table P, R is $CF_3$ and the meaning of $R^4_m$ for each individual compound corresponds in each case to one line of table A Table 56 Compounds 6876 to 7000 of formula I.C1, wherein $R^1$ is defined as in line P-8 of table P, R is $CF_3$ and the meaning of $R^4_m$ for each individual compound corresponds in each case to one line of table A Table 57 Compounds 7001 to 7125 of formula I.C1, wherein $R^1$ is defined as in line P-9 of table P, R is $CF_3$ and the meaning of $R^4_m$ for each individual compound corresponds in each case to one line of table A Table 58 Compounds 7126 to 7250 of formula I.C1, wherein $R^1$ is defined as in line P-10 of table P, R is $CF_3$ and the meaning of $R^4_m$ for each individual compound corresponds in each case to one line of table A Table 59 Compounds 7251 to 7375 of formula I.C1, wherein $R^1$ is defined as in line P-11 of table P, R is $CF_3$ and the meaning of $R^4_m$ for each individual compound corresponds in each case to one line of table A Table 60 Compounds 7376 to 7500 of formula I.C1, wherein $R^1$ is defined as in line P-12 of table P, R is $CF_3$ and the meaning of $R^4_m$ for each individual compound corresponds in each case to one line of table A Table 61 Compounds 7501 to 7625 of formula I.C1, wherein $R^1$ is defined as in line P-1 of table P, R is $CHF_2$ and the meaning of $R^4_m$ for each individual compound corresponds in each case to one line of table A Table 62 Compounds 7626 to 7750 of formula I.C1, wherein $R^1$ is defined as in line P-2 of table P, R is $CHF_2$ and the meaning of $R^4_m$ for each individual compound corresponds in each case to one line of table A Table 63 Compounds 7751 to 7875 of formula I.C1, wherein $R^1$ is defined as in line P-3 of table P, R is $CHF_2$ and the meaning of $R^4_m$ for each individual compound corresponds in each case to one line of table A Table 64 Compounds 7876 to 8000 of formula I.C1, wherein $R^1$ is defined as in line P-4 of table P, R is $CHF_2$ and the meaning of $R^4_m$ for each individual compound corresponds in each case to one line of table A Table 65 Compounds 8001 to 8125 of formula I.C1, wherein $R^1$ is defined as in line P-5 of table P, R is $CHF_2$ and the meaning of $R^4_m$ for each individual compound corresponds in each case to one line of table A Table 66 Compounds 8126 to 8250 of formula I.C1, wherein $R^1$ is defined as in line P-6 of table P, R is $CHF_2$ and the meaning of $R^4_m$ for each individual compound corresponds in each case to one line of table A Table 67 Compounds 8251 to 8375 of formula I.C1, wherein $R^1$ is defined as in line P-7 of table P, R is $CHF_2$ and the meaning of $R^4_m$ for each individual compound corresponds in each case to one line of table A Table 68 Compounds 8376 to 8500 of formula I.C1, wherein $R^1$ is defined as in line P-8 of table P, R is $CHF_2$ and the meaning of $R^4_m$ for each individual compound corresponds in each case to one line of table A Table 69 Compounds 8501 to 8625 of formula I.C1, wherein $R^1$ is defined as in line P-9 of table P, R is $CHF_2$ and the meaning of $R^4_m$ for each individual compound corresponds in each case to one line of table A Table 70 Compounds 8626 to 8750 of formula I.C1, wherein $R^1$ is defined as in line P-10 of table P, R is $CHF_2$ and the meaning of $R^4_m$ for each individual compound corresponds in each case to one line of table A Table 71 Compounds 8751 to 8875 of formula I.C1, wherein $R^1$ is defined as in line P-11 of table P, R is $CHF_2$ and the meaning of $R^4_m$ for each individual compound corresponds in each case to one line of table A Table 72 Compounds 8876 to 9000 of formula I.C1, wherein $R^1$ is defined as in line P-12 of table P, R is $CHF_2$ and the meaning of $R^4_m$ for each individual compound corresponds in each case to one line of table A Consequently, for example compound 130 of the invention as disclosed in Table 2, has the structure of formula I.A1 (see above), $R^1$ is methyl (line P-2 of table P), R is $CF_3$ and $R^4_m$ for compound 130 corresponds to the fifth line of table A and is, thus 2-F.

TABLE A

| No. | $R^4_m$ |
|---|---|
| 1 | —* |
| 2 | 2-Cl |
| 3 | 3-Cl |

TABLE A-continued

| No. | $R^4_m$ |
|---|---|
| 4 | 4-Cl |
| 5 | 2-F |
| 6 | 3-F |
| 7 | 4-F |
| 8 | 2,3-Cl$_2$ |
| 9 | 2,4-Cl$_2$ |
| 10 | 3,4-Cl$_2$ |
| 11 | 2,6-Cl$_2$ |
| 12 | 2,3-F$_2$ |
| 13 | 2,4-F$_2$ |
| 14 | 3,4-F$_2$ |
| 15 | 2,6-F$_2$ |
| 16 | 2-F-3-Cl |
| 17 | 2-F-4-Cl |
| 18 | 3-F-4-Cl |
| 19 | 2-F-6-Cl |
| 20 | 2-Cl-3-F |
| 21 | 2-Cl-4-F |
| 22 | 3-Cl-4-F |
| 23 | 2,3,4-Cl$_3$ |
| 24 | 2,4,5-Cl$_3$ |
| 25 | 3,4,5-Cl$_3$ |
| 26 | 2,4,6-Cl$_3$ |
| 27 | 2,3,4-F$_3$ |
| 28 | 2,4,5-F$_3$ |
| 29 | 3,4,5-F$_3$ |
| 30 | 2,4,6-F$_3$ |
| 31 | 2,3-4-F$_3$ |
| 32 | 2,4-F$_2$-3-Cl |
| 33 | 2,6-F$_2$-4-Cl |
| 34 | 2,5-F$_2$-4-Cl |
| 35 | 2,4-Cl$_2$-3-F |
| 36 | 2,6-Cl$_2$-4-F |
| 37 | 2,5-Cl$_2$-4-F |
| 38 | 2-CH$_3$ |
| 39 | 3-CH$_3$ |
| 40 | 4-CH$_3$ |
| 41 | 2-CH$_2$CH$_3$ |
| 42 | 3-CH$_2$CH$_3$ |
| 43 | 4-CH$_2$CH$_3$ |
| 44 | 2-CF$_3$ |
| 45 | 3-CF$_3$ |
| 46 | 4-CF$_3$ |
| 47 | 2-CHF$_2$ |
| 48 | 3-CHF$_2$ |
| 49 | 4-CHF$_2$ |
| 50 | 2-OCH$_3$ |
| 51 | 3-OCH$_3$ |
| 52 | 4-OCH$_3$ |
| 53 | 2-OCH$_2$CH$_3$ |
| 54 | 3-OCH$_2$CH$_3$ |
| 55 | 4-OCH$_2$CH$_3$ |
| 56 | 2-OCF$_3$ |
| 57 | 3-OCF$_3$ |
| 58 | 4-OCF$_3$ |
| 59 | 2-OCHF$_2$ |
| 60 | 3-OCHF$_2$ |
| 61 | 4-OCHF$_2$ |
| 62 | 2,3-(CH$_3$)$_2$ |
| 63 | 2,4-(CH$_3$)$_2$ |
| 64 | 3,4-(CH$_3$)$_2$ |
| 65 | 2,6-(CH$_3$)$_2$ |
| 66 | 2,3-(CH$_2$CH$_3$)$_2$ |
| 67 | 2,4-(CH$_2$CH$_3$)$_2$ |
| 68 | 3,4-(CH$_2$CH$_3$)$_2$ |
| 69 | 2,6-(CH$_2$CH$_3$)$_2$ |
| 70 | 2,3-(CF$_3$)$_2$ |
| 71 | 2,4-(CF$_3$)$_2$ |
| 72 | 3,4-(CF$_3$)$_2$ |
| 73 | 2,6-(CF$_3$)$_2$ |
| 74 | 2,3-(CHF$_2$)$_2$ |
| 75 | 2,4-(CHF$_2$)$_2$ |
| 76 | 3,4-(CHF$_2$)$_2$ |
| 77 | 2,6-(CHF$_2$)$_2$ |
| 78 | 2,3-(OCH$_3$)$_2$ |
| 79 | 2,4-(OCH$_3$)$_2$ |
| 80 | 3,4-(OCH$_3$)$_2$ |
| 81 | 2,6-(OCH$_3$)$_2$ |
| 82 | 2,3-(OCH$_2$CH$_3$)$_2$ |
| 83 | 2,4-(OCH$_2$CH$_3$)$_2$ |
| 84 | 3,4-(OCH$_2$CH$_3$)$_2$ |
| 85 | 2,6-(OCH$_2$CH$_3$)$_2$ |
| 86 | 2,3-(OCF$_3$)$_2$ |
| 87 | 2,4-(OCF$_3$)$_2$ |
| 88 | 3,4-(OCF$_3$)$_2$ |
| 89 | 2,6-(OCF$_3$)$_2$ |
| 90 | 2,3-(OCHF$_2$)$_2$ |
| 91 | 2,4-(OCHF$_2$)$_2$ |
| 92 | 3,4-(OCHF$_2$)$_2$ |
| 93 | 2,6-(OCHF$_2$)$_2$ |
| 94 | 2,3,4-(CH$_3$)$_3$ |
| 95 | 2,4,5-(CH$_3$)$_3$ |
| 96 | 3,4,5-(CH$_3$)$_3$ |
| 97 | 2,4,6-(CH$_3$)$_3$ |
| 98 | 2,3,4-(CH$_2$CH$_3$)$_3$ |
| 99 | 2,4,5-(CH$_2$CH$_3$)$_3$ |
| 100 | 3,4,5-(CH$_2$CH$_3$)$_3$ |
| 101 | 2,4,6-(CH$_2$CH$_3$)$_3$ |
| 102 | 2,3,4-(CF$_3$)$_3$ |
| 103 | 2,4,5-(CF$_3$)$_3$ |
| 104 | 3,4,5-(CF$_3$)$_3$ |
| 105 | 2,4,6-(CF$_3$)$_3$ |
| 106 | 2,3,4-(CHF$_2$)$_3$ |
| 107 | 2,4,5-(CHF$_2$)$_3$ |
| 108 | 3,4,5-(CHF$_2$)$_3$ |
| 109 | 2,4,6-(CHF$_2$)$_3$ |
| 110 | 2,3,4-(OCH$_3$)$_3$ |
| 111 | 2,4,5-(OCH$_3$)$_3$ |
| 112 | 3,4,5-(OCH$_3$)$_3$ |
| 113 | 2,4,6-(OCH$_3$)$_3$ |
| 114 | 2,3,4-(OCH$_2$CH$_3$)$_3$ |
| 115 | 2,4,5-(OCH$_2$CH$_3$)$_3$ |
| 116 | 3,4,5-(OCH$_2$CH$_3$)$_3$ |
| 117 | 2,4,6-(OCH$_2$CH$_3$)$_3$ |
| 118 | 2,3,4-(OCF$_3$)$_3$ |
| 119 | 2,4,5-(OCF$_3$)$_3$ |
| 120 | 3,4,5-(OCF$_3$)$_3$ |
| 121 | 2,4,6-(OCF$_3$)$_3$ |
| 122 | 2,3,4-(OCHF$_2$)$_3$ |
| 123 | 2,4,5-(OCHF$_2$)$_3$ |
| 124 | 3,4,5-(OCHF$_2$)$_3$ |
| 125 | 2,4,6-(OCHF$_2$)$_3$ |

*this means that m = 0

Further embodiments of the present invention are compounds I, wherein n is 0 and $R^2$ is isopropyl, CH$_2$-phenyl, CH$_2$-(4-Cl-phenyl), CH$_2$-(4-F-phenyl), CH$_2$-(4-CH$_3$-phenyl), CH$_2$-(4-OCH$_3$-phenyl), CH$_2$—OCH$_3$, CH$_2$—CH=CH$_2$, n-propyl, CH$_2$—C≡C—H, CH$_2$—C≡C—CH$_3$ or CH$_2$C(CH$_3$)=CH$_2$, which compounds are of formulae I.D1, I.E1, I.F1, I.G1, I.H1, I.J1, I.K1, I.L1, I.M1, I.N1, I.O1 and I.P1, respectively:

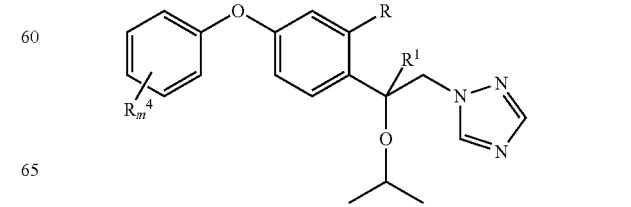

I.D1

-continued
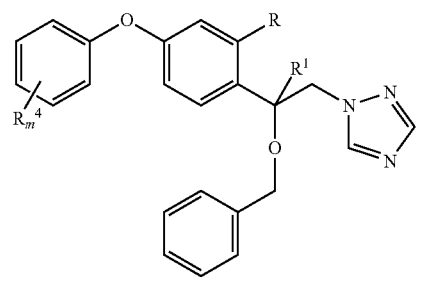
I.E1
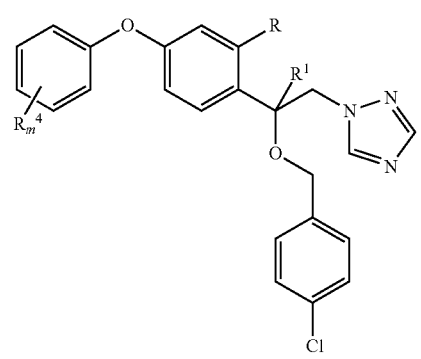
I.F1
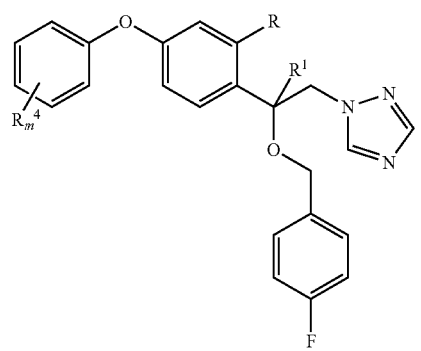
I.G1
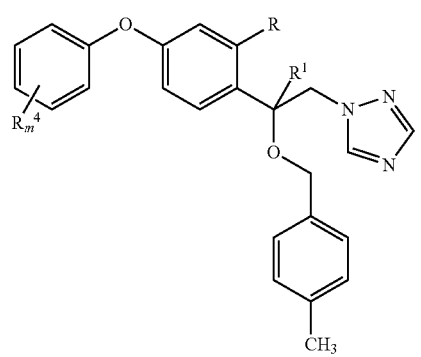
I.H1
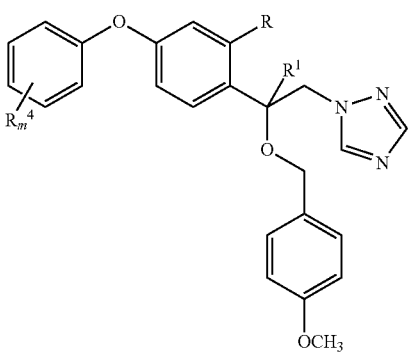
I.J1
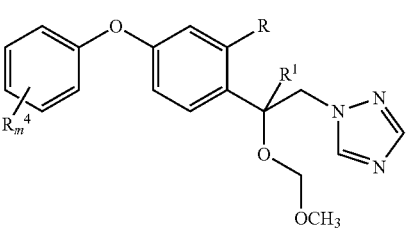
I.K1
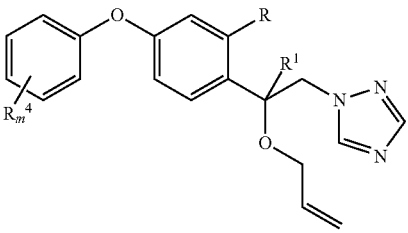
I.L1
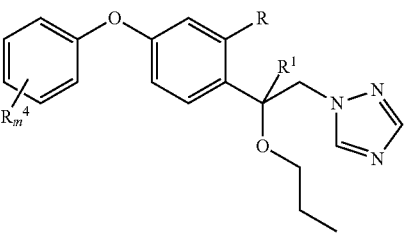
I.M1
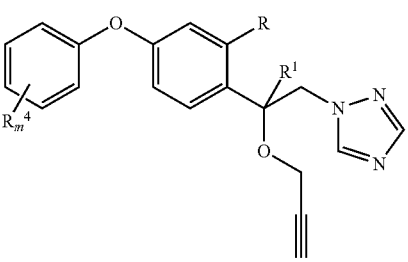
I.N1
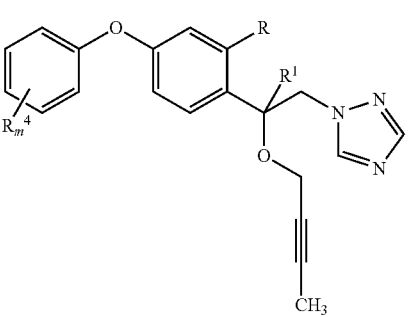
I.O1

-continued

I.P1

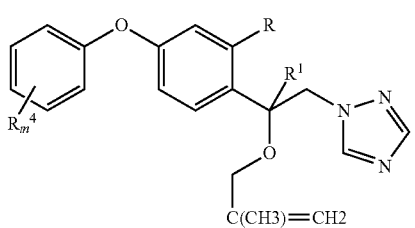

C(CH3)=CH2

Further embodiments of the present invention are compounds I, wherein $R^3_n$ is ortho-$CH_3$ (ortho in relation to the linkage of the alcohol group to the phenyl ring) and $R^2$ is hydrogen, methyl, ethyl, isopropyl, $CH_2$-phenyl, $CH_2$-(4-Cl-phenyl), $CH_2$-(4-F-phenyl), $CH_2$-(4-$CH_3$-phenyl), $CH_2$-(4-$OCH_3$-phenyl), $CH_2$—$OCH_3$, $CH_2$—CH=$CH_2$, n-propyl, $CH_2$—C≡C—H, $CH_2$—C≡C—$CH_3$ or $CH_2C(CH_3)$=$CH_2$, which compounds are of formulae I.A2, I.B2, I.C2, I.D2, I.E2, I.F2, I.G2, I.H2, I.J2, I.K2, I.L2, I.M2, I.N2, I.O2 and I.P2 respectively:

I.A2

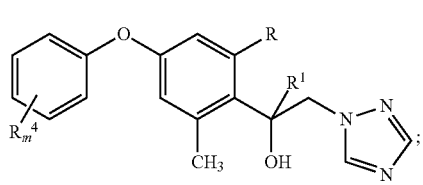

I.B2

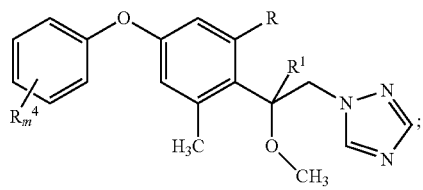

I.C2

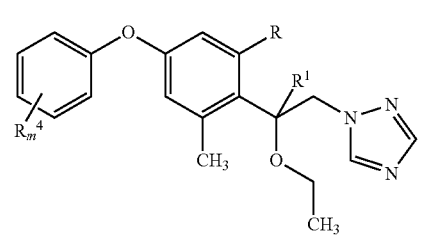

I.D2

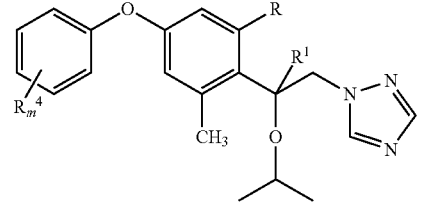

I.E2

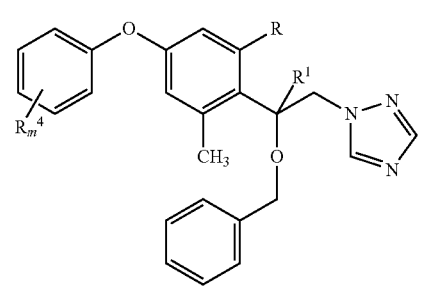

I.F2

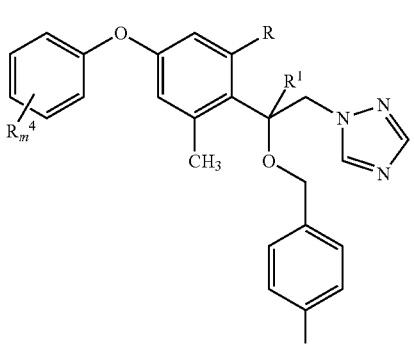

I.G2

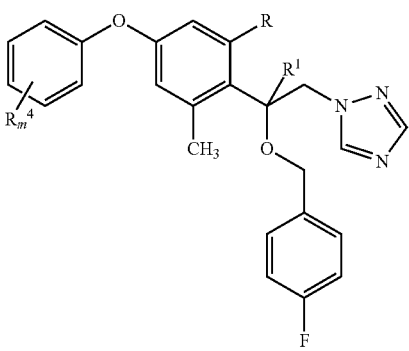

I.H2

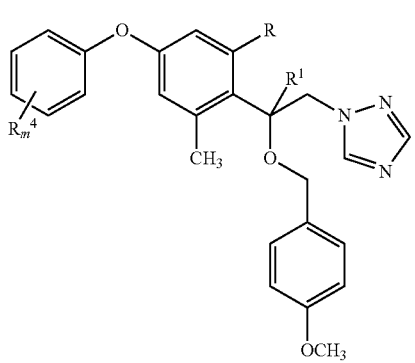

I.J2

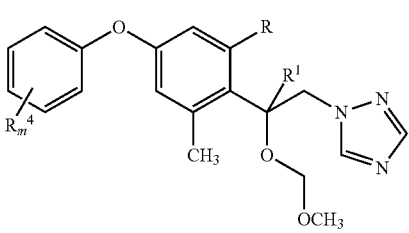

I.K2

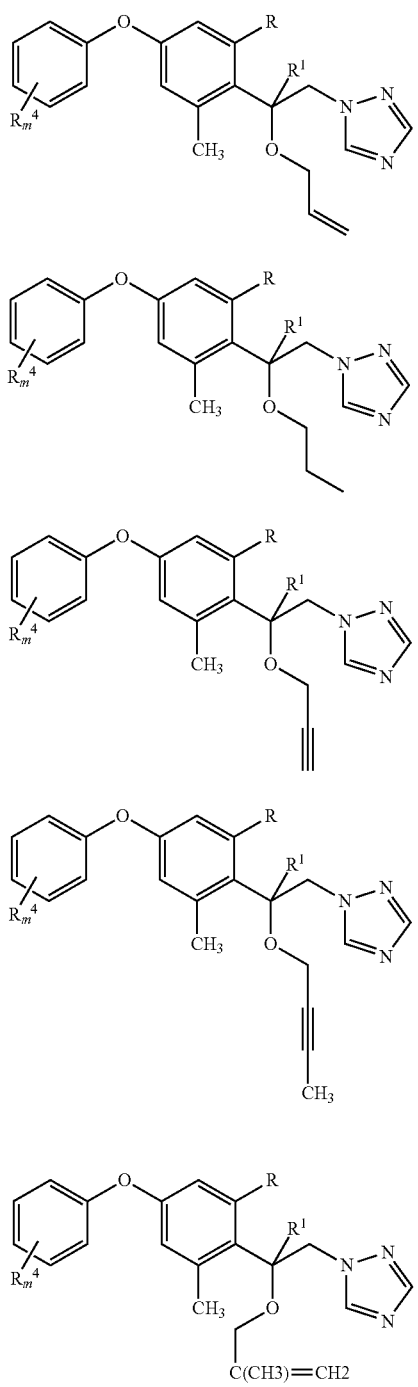

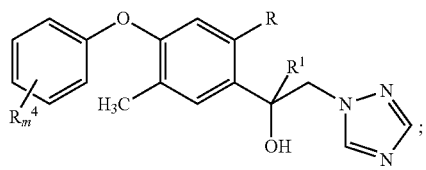

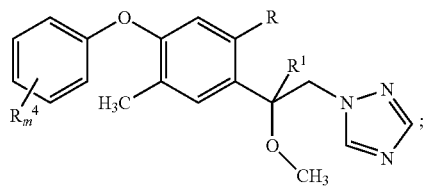

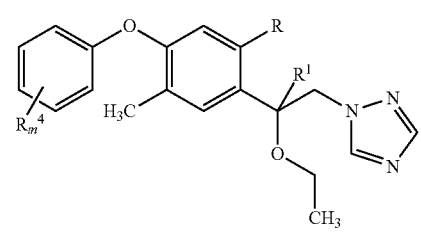

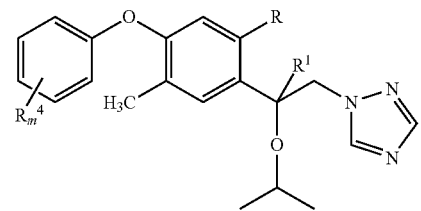

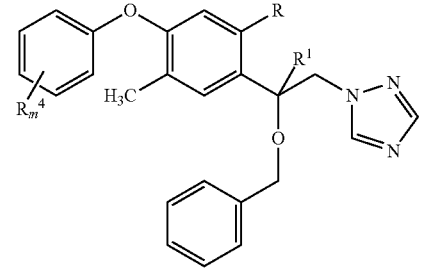

Further embodiments of the present invention are compounds I, wherein $R^3_n$ is meta-$CH_3$ (meta in relation to the linkage of the alcohol group to the phenyl ring) and $R^2$ is hydrogen, methyl, ethyl, isopropyl, $CH_2$-phenyl, $CH_2$-(4-Cl-phenyl), $CH_2$-(4-F-phenyl), $CH_2$-(4-$CH_3$-phenyl), $CH_2$-(4-$OCH_3$-phenyl), $CH_2$—$OCH_3$, $CH_2$—CH=$CH_2$, n-propyl, $CH_2$—C≡C—H, $CH_2$—C≡C—$CH_3$ or $CH_2C(CH_3)$=$CH_2$, which compounds are of formulae I.A3, I.B3, I.C3, I.D3, I.E3, I.F3, I.G3, I.H3, I.J3, I.K3, I.L3, I.M3, I.N3, I.O3 and I.P3 respectively:

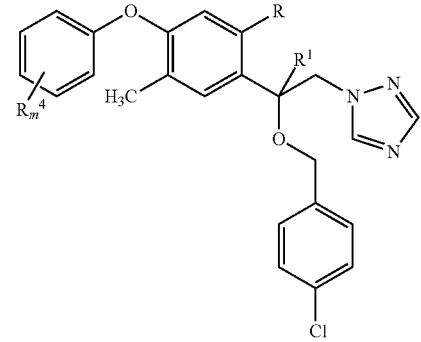

I.G3
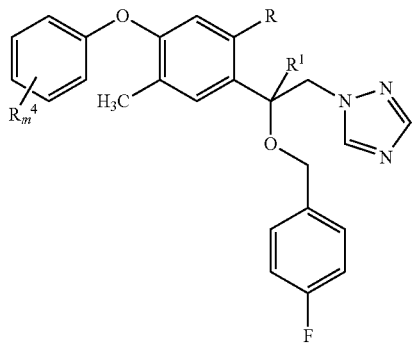

I.H3
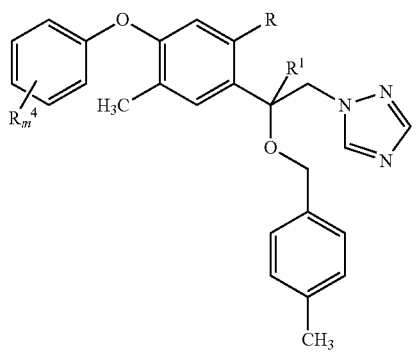

I.J3
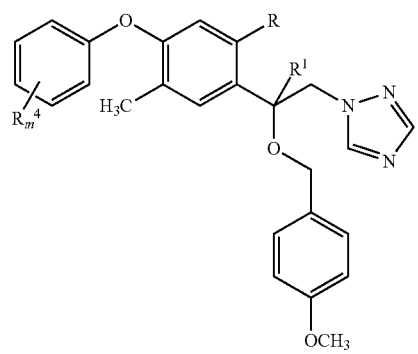

I.K3
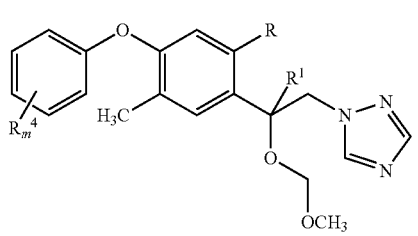

I.L3
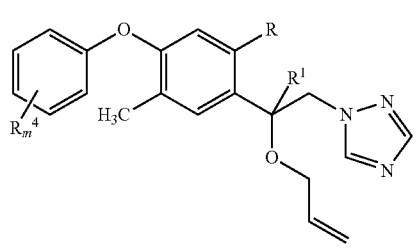

I.M3
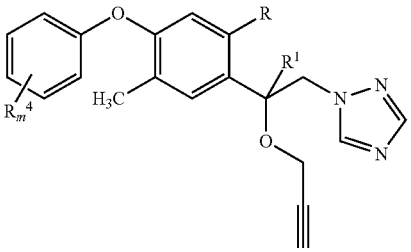

I.N3
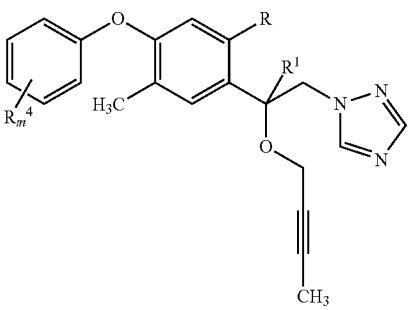

I.O3
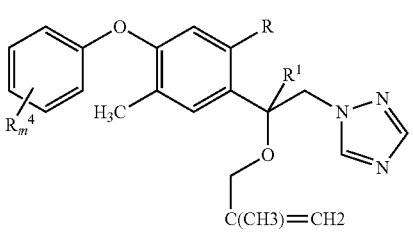

I.P3
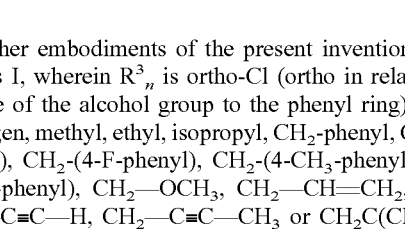

Further embodiments of the present invention are compounds I, wherein $R^3_n$ is ortho-Cl (ortho in relation to the linkage of the alcohol group to the phenyl ring) and $R^2$ is hydrogen, methyl, ethyl, isopropyl, $CH_2$-phenyl, $CH_2$-(4-Cl-phenyl), $CH_2$-(4-F-phenyl), $CH_2$-(4-$CH_3$-phenyl), $CH_2$-(4-$OCH_3$-phenyl), $CH_2$—$OCH_3$, $CH_2$—CH=$CH_2$, n-propyl, $CH_2$—C≡C—H, $CH_2$—C≡C—$CH_3$ or $CH_2C(CH_3)$=$CH_2$, which compounds are of formulae I.A4, I.B4, I.C4, I.D4, I.E4, I.F4, I.G4, I.H4, I.J4, I.K4, I.L4, I.M4, I.N4, I.O4 and I.P4 respectively:

I.A4
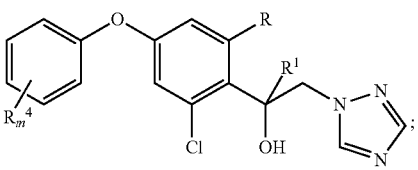

-continued
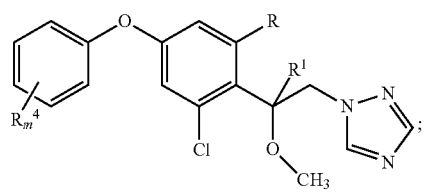
I.B4
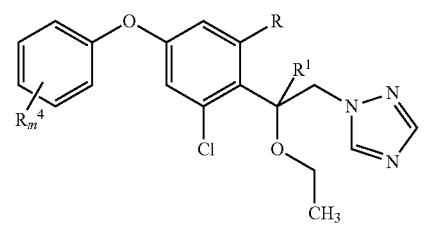
I.C4
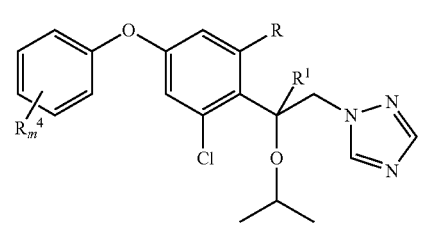
I.D4
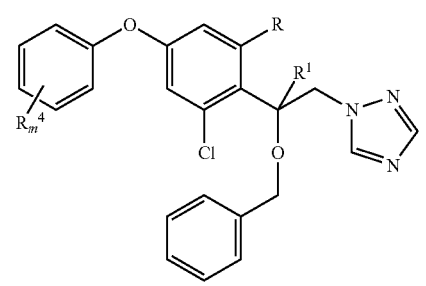
I.E4
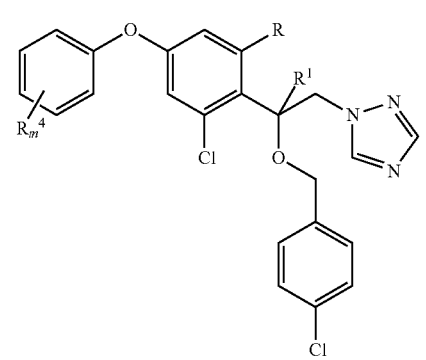
I.F4
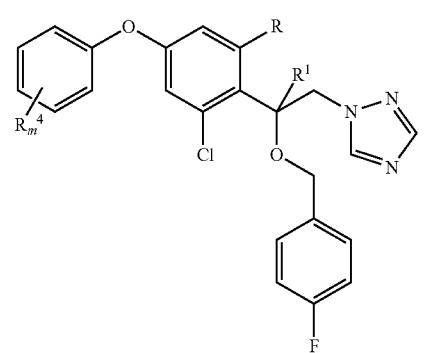
I.G4
-continued
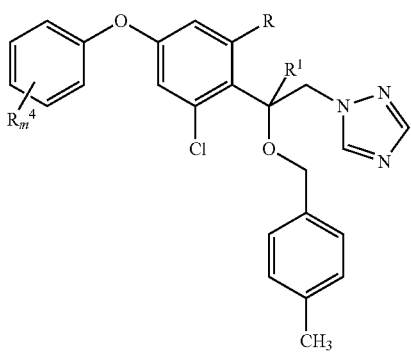
I.H4
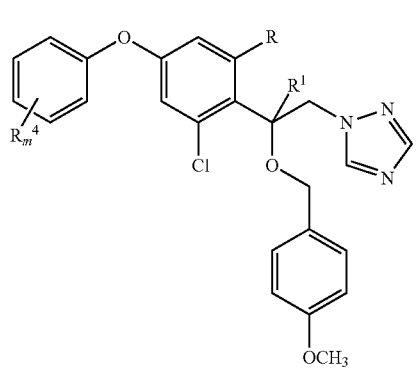
I.J4
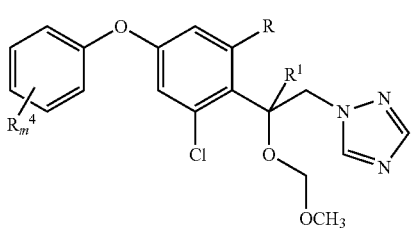
I.K4
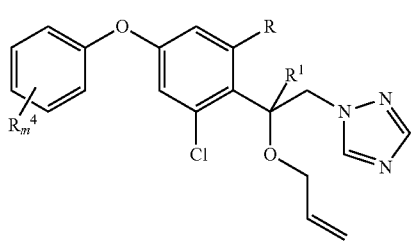
I.L4
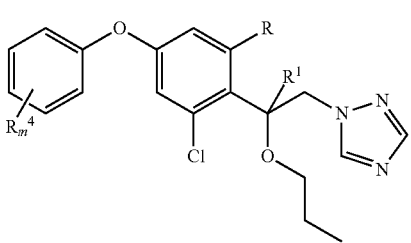
I.M4

-continued

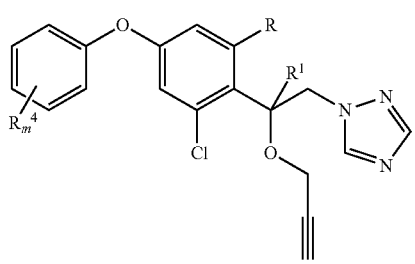
I.N4

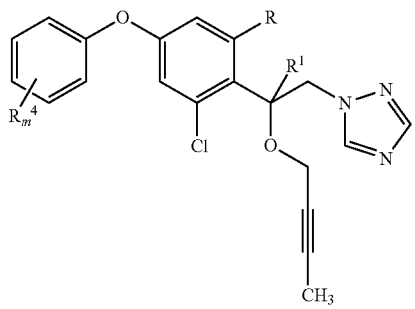
I.O4

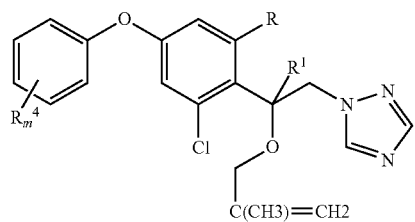
I.P4

Further embodiments of the present invention are compounds I, wherein $R^3_n$ is meta-Cl (meta in relation to the linkage of the alcohol group to the phenyl ring) and $R^2$ is hydrogen, methyl, ethyl, isopropyl, CH$_2$-phenyl, CH$_2$-(4-Cl-phenyl), CH$_2$-(4-F-phenyl), CH$_2$-(4-CH$_3$-phenyl), CH$_2$-(4-OCH$_3$-phenyl), CH$_2$—OCH$_3$, CH$_2$—CH═CH$_2$, n-propyl, CH$_2$—C≡C—H, CH$_2$—C≡C—CH$_3$ or CH$_2$C(CH$_3$)═CH$_2$, which compounds are of formulae I.A5, I.B5, I.C5, I.D5, I.E5, I.F5, I.G5, I.H5, I.J5, I.K5, I.L5, I.M5, I.N5, I.O5 and I.P5 respectively:

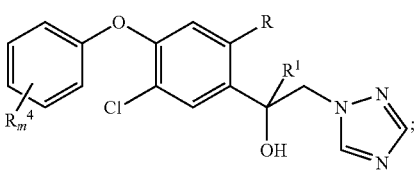
I.A5

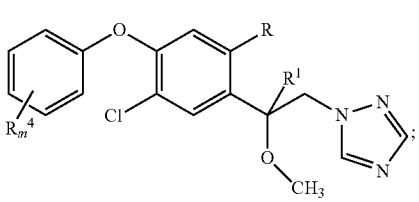
I.B5

-continued

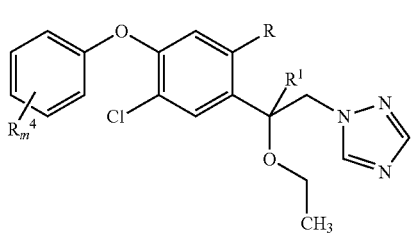
I.C5

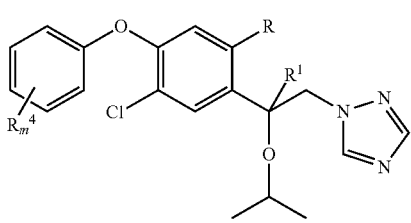
I.D5

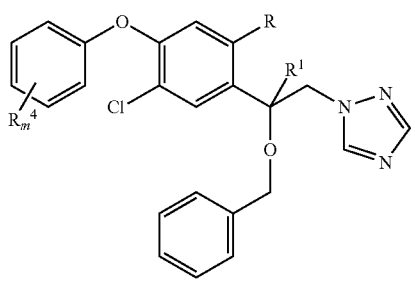
I.E5

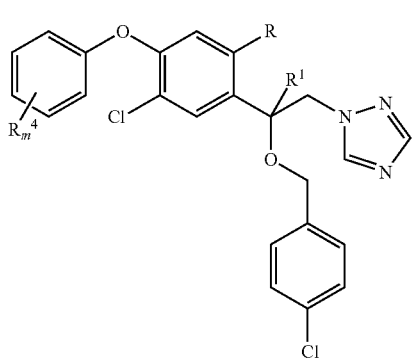
I.F5

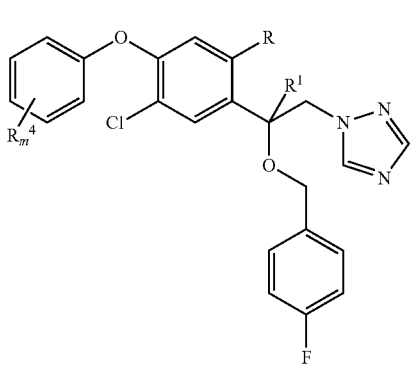
I.G5

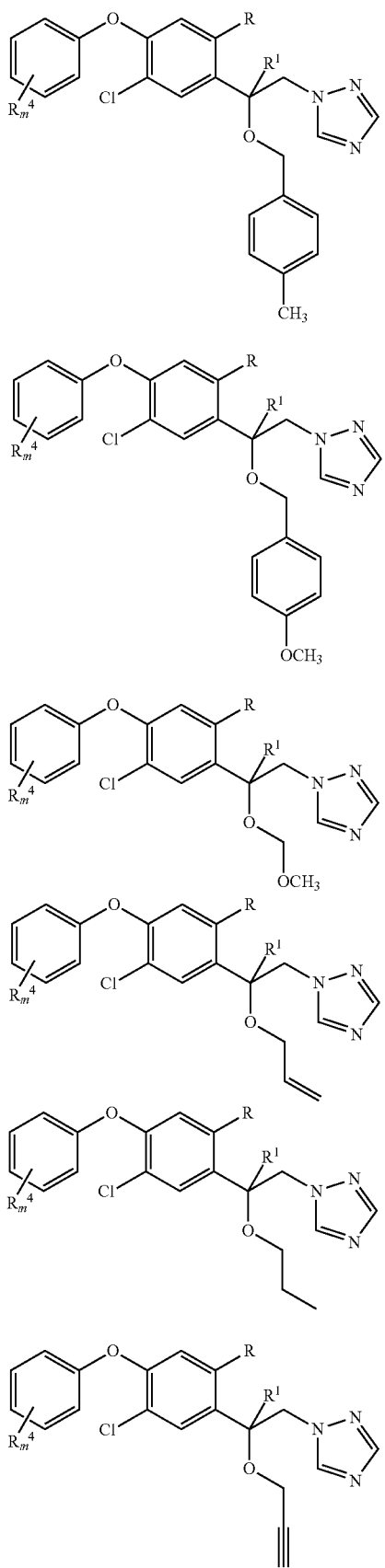

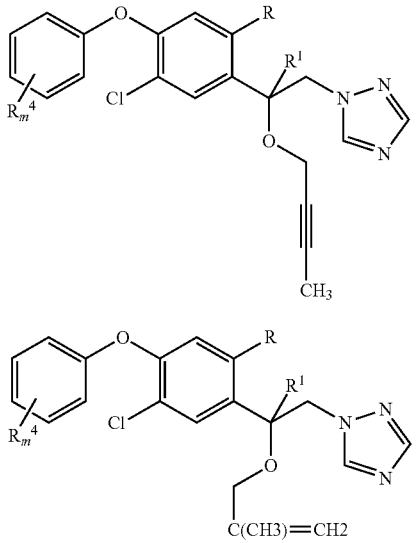

Further embodiments of the present invention are compounds I, wherein $R^3_n$ is ortho-Br (ortho in relation to the linkage of the alcohol group to the phenyl ring) and $R^2$ is hydrogen, methyl, ethyl, isopropyl, $CH_2$-phenyl, $CH_2$-(4-Cl-phenyl), $CH_2$-(4-F-phenyl), $CH_2$-(4-$CH_3$-phenyl), $CH_2$-(4-$OCH_3$-phenyl), $CH_2$—$OCH_3$, $CH_2$—CH=$CH_2$, n-propyl, $CH_2$—C≡C—H, $CH_2$—C≡C—$CH_3$ or $CH_2C(CH_3)$=$CH_2$, which compounds are of formulae I.A6, I.B6, I.C6, I.D6, I.E6, I.F6, I.G6, I.H6, I.J6, I.K6, I.L6, I.M6, I.N6, I.O6 and I.P6 respectively:

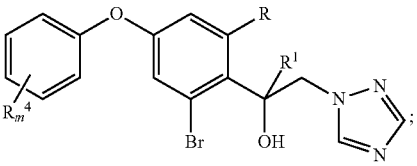

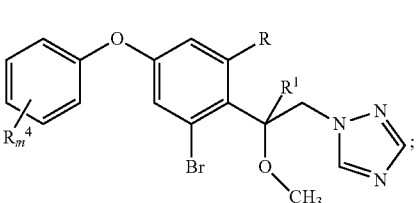

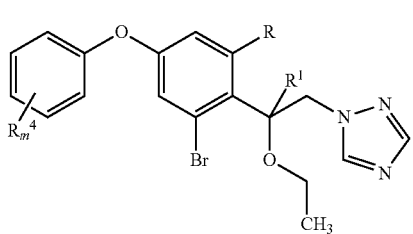

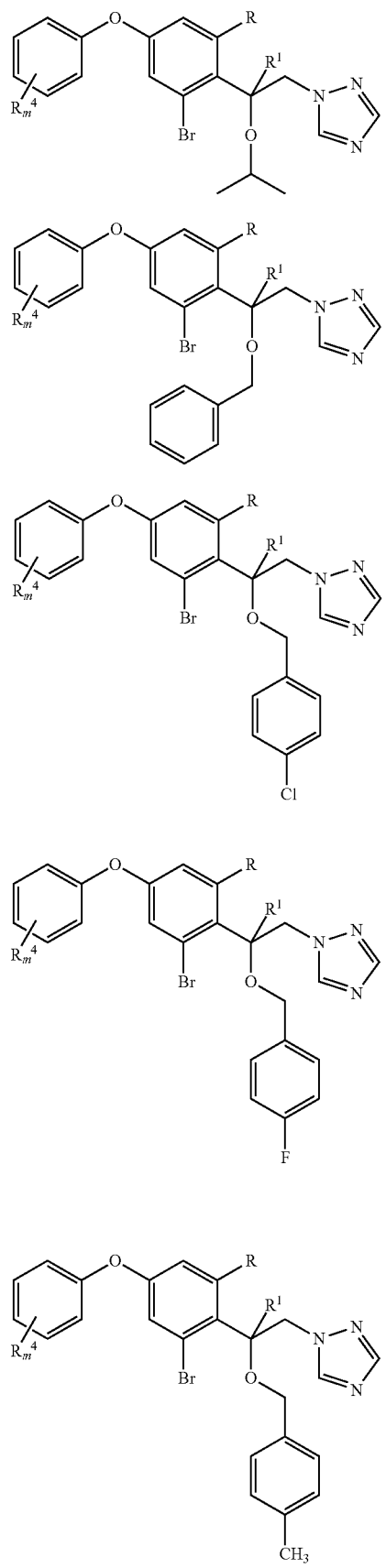
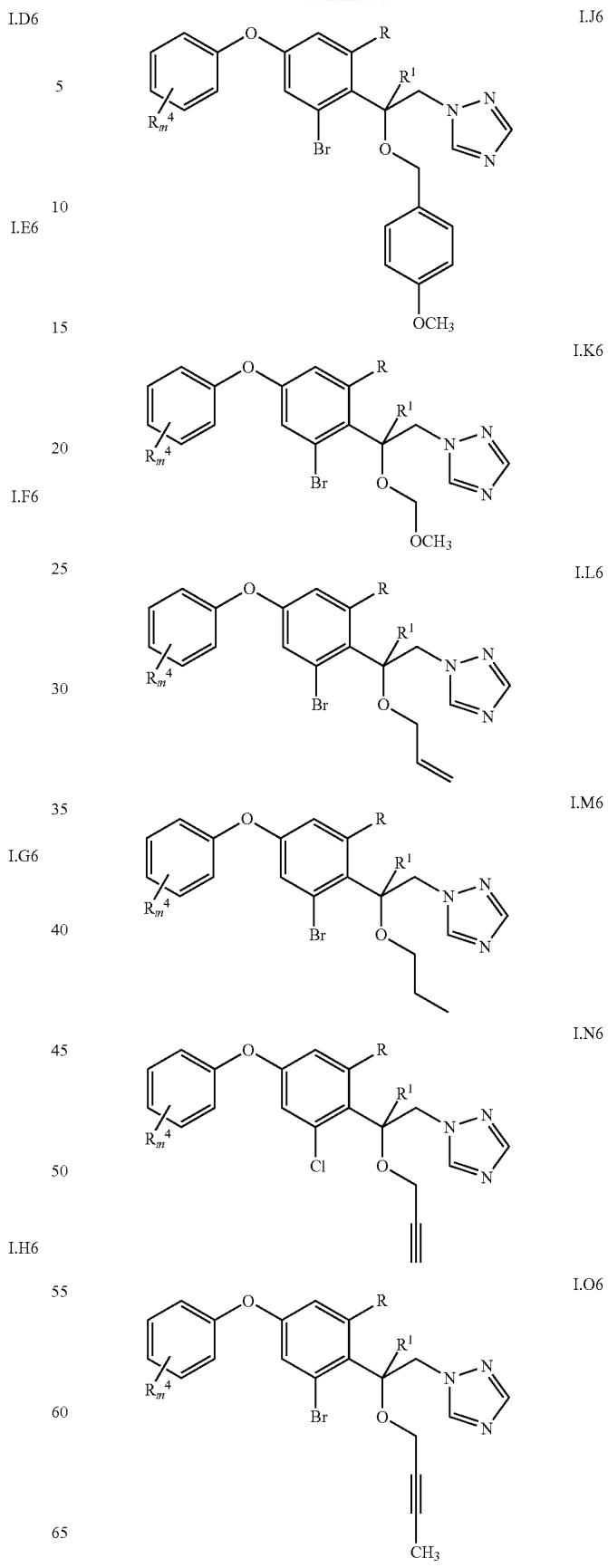

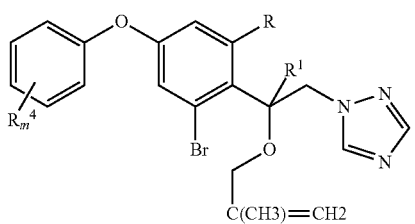
I.P6

Further embodiments of the present invention are compounds I, wherein $R^3_n$ is meta-Br (meta in relation to the linkage of the alcohol group to the phenyl ring) and $R^2$ is hydrogen, methyl, ethyl, isopropyl, $CH_2$-phenyl, $CH_2$-(4-Cl-phenyl), $CH_2$-(4-F-phenyl), $CH_2$-(4-$CH_3$-phenyl), $CH_2$-(4-$OCH_3$-phenyl), $CH_2$—$OCH_3$, $CH_2$—CH=$CH_2$, n-propyl, $CH_2$—C≡C—H, $CH_2$—C≡C—$CH_3$ or $CH_2C(CH_3)$=$CH_2$, which compounds are of formulae I.A7, I.B7, I.C7, I.D7, I.E7, I.F7, I.G7, I.H7, I.J7, I.K7, I.L7, I.M7, I.N7, I.O7 and I.P7 respectively:

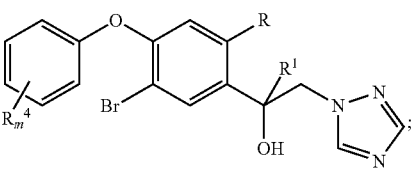
I.A7

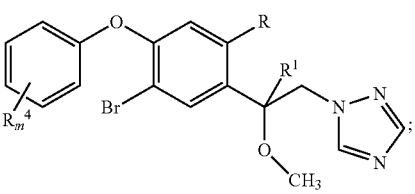
I.B7

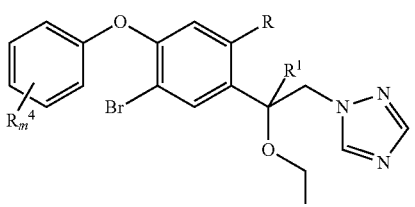
I.C7

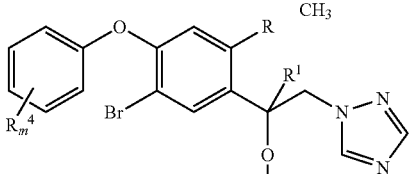
I.D7

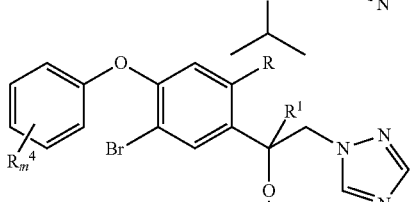
I.E7

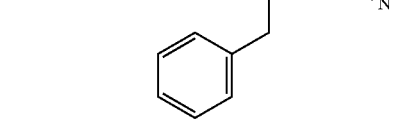
I.F7

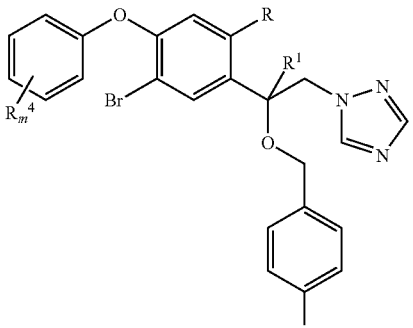
I.F7

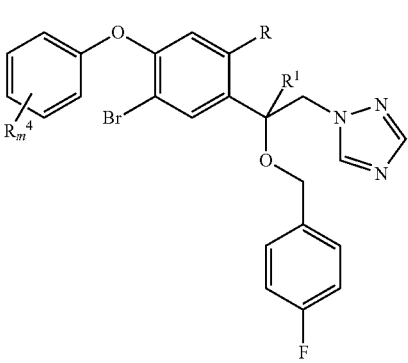
I.G7

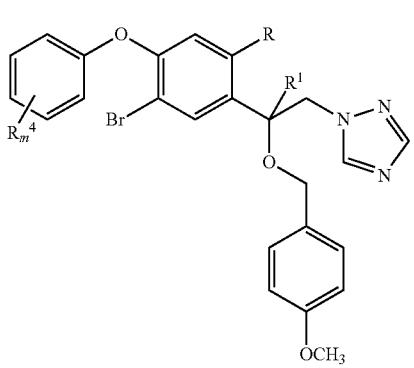
I.H7

I.J7

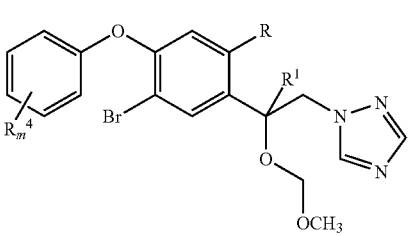
I.K7

-continued

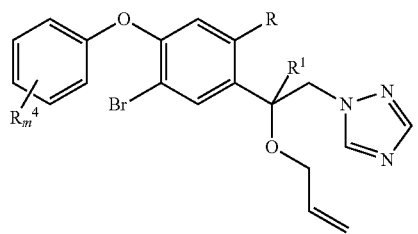

I.L7

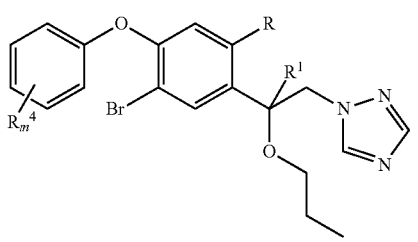

I.M7

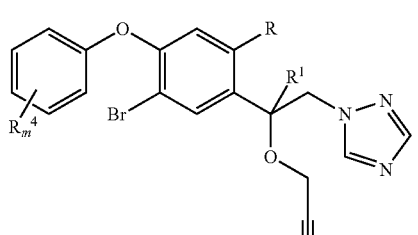

I.N7

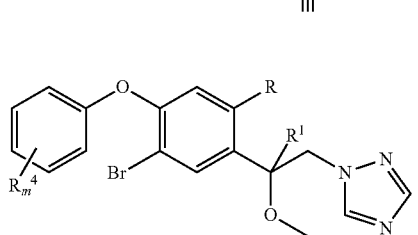

I.O7

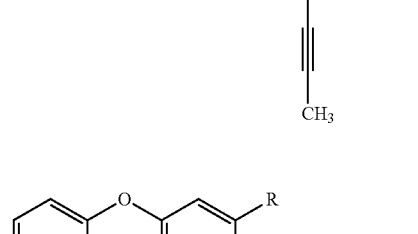

I.P7

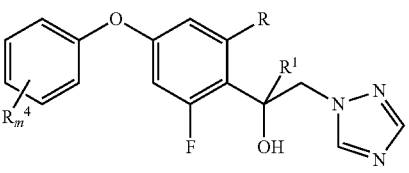

I.A8

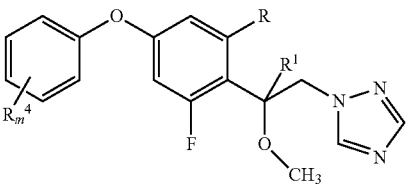

I.B8

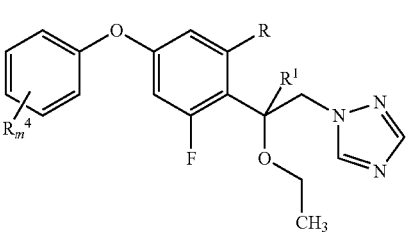

I.C8

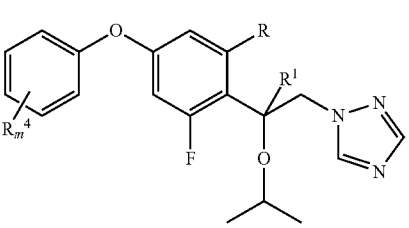

I.D8

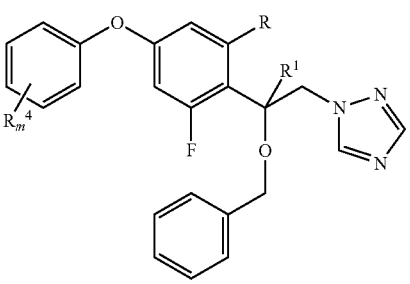

I.E8

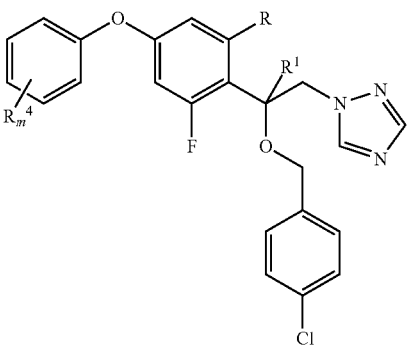

I.F8

Further embodiments of the present invention are compounds I, wherein $R^3{}_n$ is ortho-F (ortho in relation to the linkage of the alcohol group to the phenyl ring) and $R^2$ is hydrogen, methyl, ethyl, isopropyl, $CH_2$-phenyl, $CH_2$-(4-Cl-phenyl), $CH_2$-(4-F-phenyl), $CH_2$-(4-$CH_3$-phenyl), $CH_2$-(4-$OCH_3$-phenyl), $CH_2$—$OCH_3$, $CH_2$—CH=$CH_2$, n-propyl, $CH_2$—C≡C—H, $CH_2$—C≡C—$CH_3$ or $CH_2C(CH_3)$=$CH_2$, which compounds are of formulae I.A8, I.B8, I.C8, I.D8, I.E8, I.F8, I.G8, I.H8, I.J8, I.K8, I.L8, I.M8, I.N8, I.O8 and I.P8 respectively:

I.G8

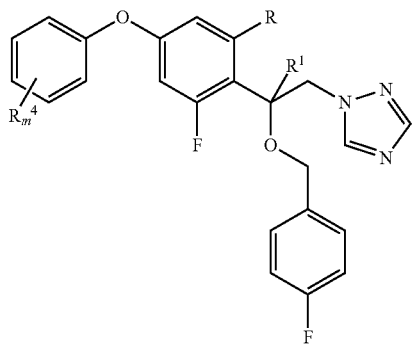

I.H8

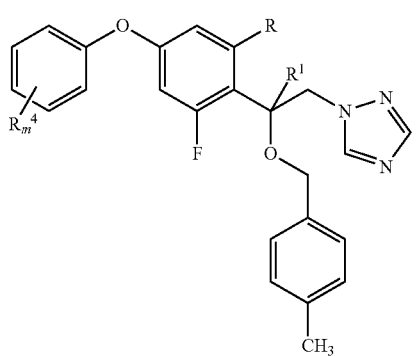

I.J8

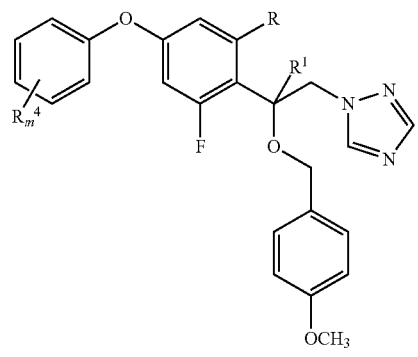

I.K8

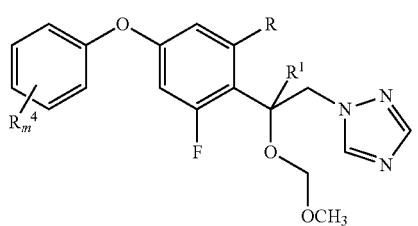

I.L8

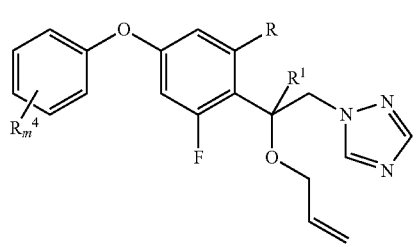

I.M8

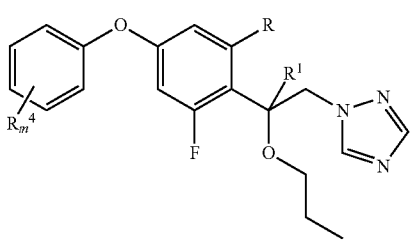

I.N8

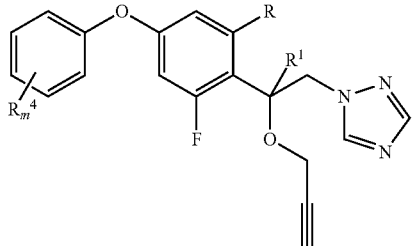

I.O8

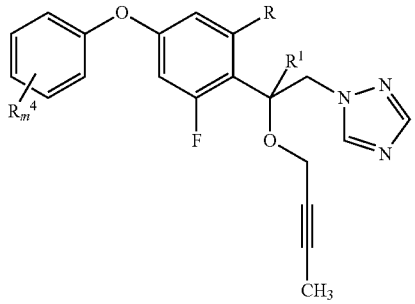

I.P8

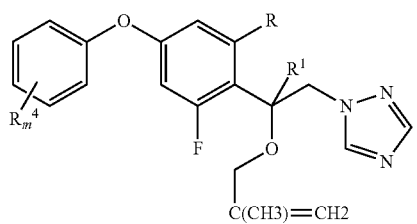

Further embodiments of the present invention are compounds I, wherein $R^3_n$ is meta-F (meta in relation to the linkage of the alcohol group to the phenyl ring) and $R^2$ is hydrogen, methyl, ethyl, isopropyl, CH$_2$-phenyl, CH$_2$-(4-Cl-phenyl), CH$_2$-(4-F-phenyl), CH$_2$-(4-CH$_3$-phenyl), CH$_2$-(4-OCH$_3$-phenyl), CH$_2$—OCH$_3$, CH$_2$—CH═CH$_2$, n-propyl, CH$_2$—C≡C—H, CH$_2$—C≡C—CH$_3$ or CH$_2$C(CH$_3$)═CH$_2$, which compounds are of formulae I.A9, I.B9, I.C9, I.D9, I.E9, I.F9, I.G9, I.H9, I.J9, I.K9, I.L9, I.M9, I.N9, I.O9 and I.P9 respectively:

I.A9

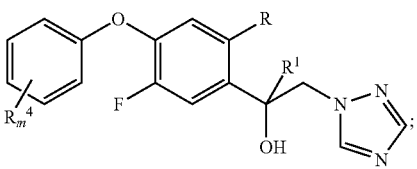

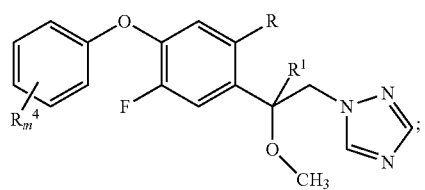 I.B9
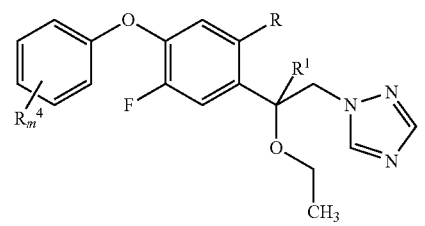 I.C9
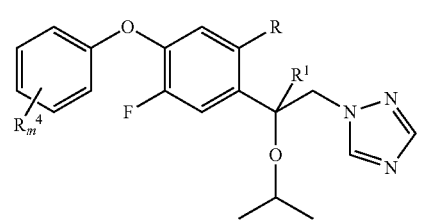 I.D9
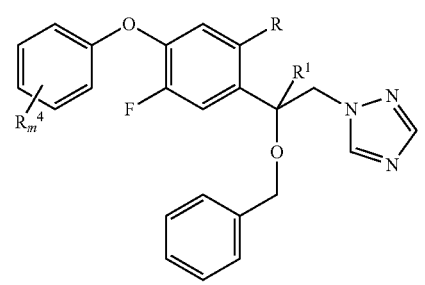 I.E9
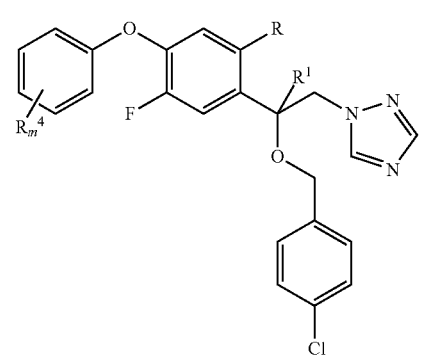 I.F9
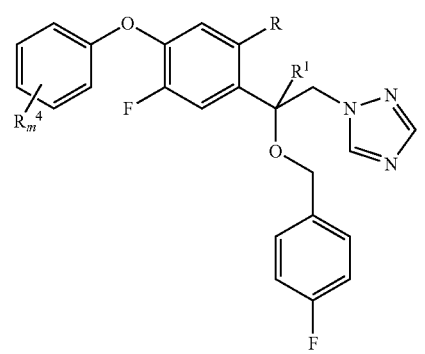 I.G9
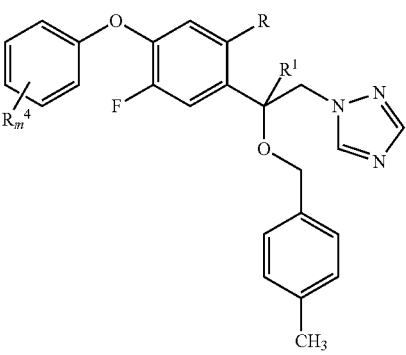 I.H9
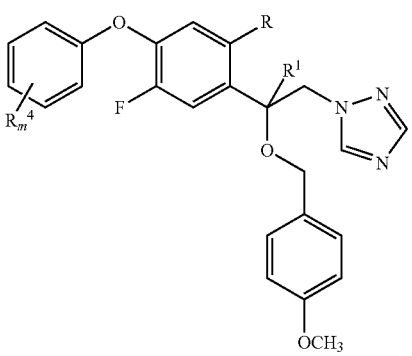 I.J9
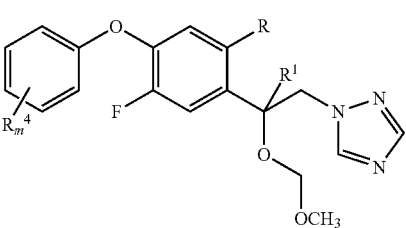 I.K9
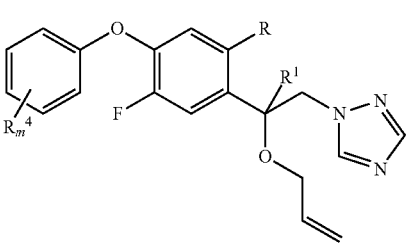 I.L9
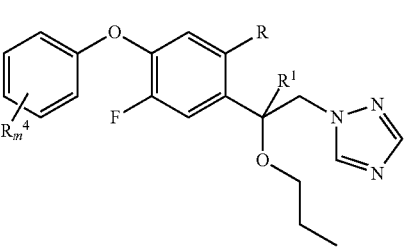 I.M9

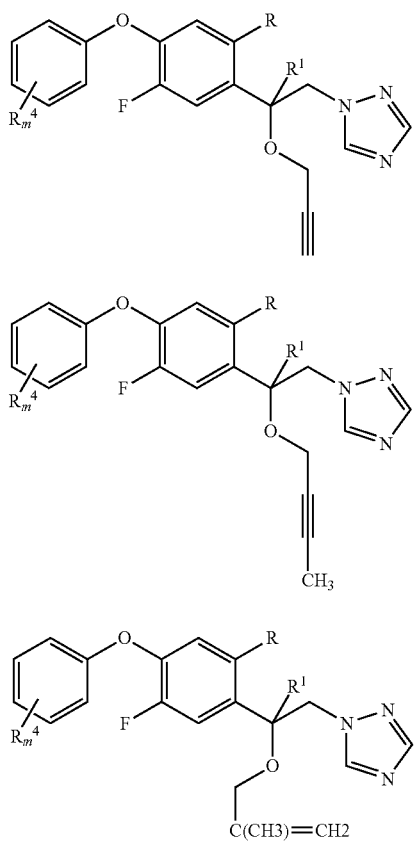

I.N9

I.O9

I.P9

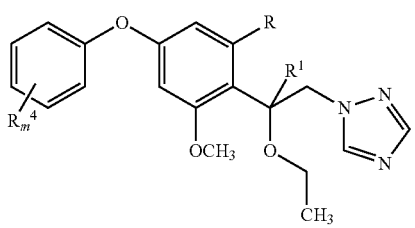

I.C10

I.D10

I.E10

Further embodiments of the present invention are compounds I, wherein $R^3{}_n$ is ortho-OCH$_3$ (ortho in relation to the linkage of the alcohol group to the phenyl ring) and $R^2$ is hydrogen, methyl, ethyl, isopropyl, CH$_2$-phenyl, CH$_2$-(4-Cl-phenyl), CH$_2$-(4-F-phenyl), CH$_2$-(4-CH$_3$-phenyl), CH$_2$-(4-OCH$_3$-phenyl), CH$_2$—OCH$_3$, CH$_2$—CH═CH$_2$, n-propyl, CH$_2$—C≡C—H, CH$_2$—C≡C—CH$_3$ or CH$_2$C(CH$_3$)═CH$_2$, which compounds are of formulae I.A10, I.B10, I.C10, I.D10, I.E10, I.F10, I.G10, I.H10, I.J10, I.K10, I.L10, I.M10, I.N10, I.O10 and I.P10 respectively:

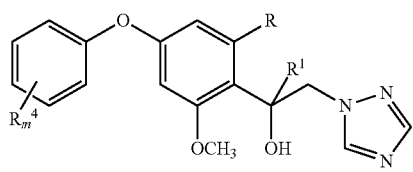

I.A10

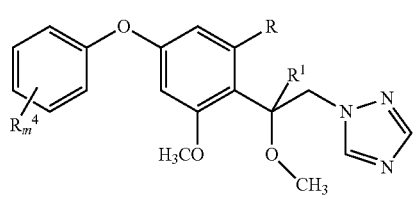

I.B10

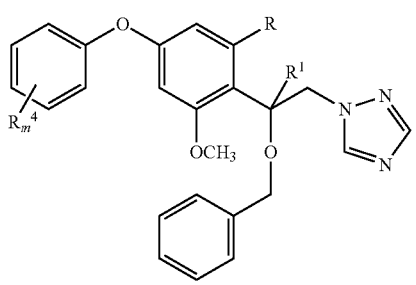

I.F10

I.G10

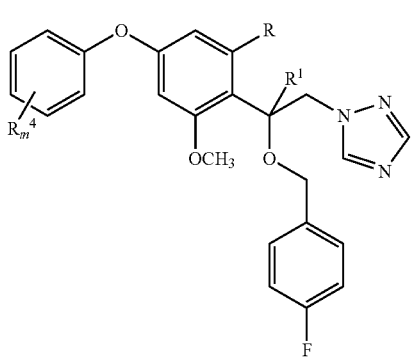

-continued

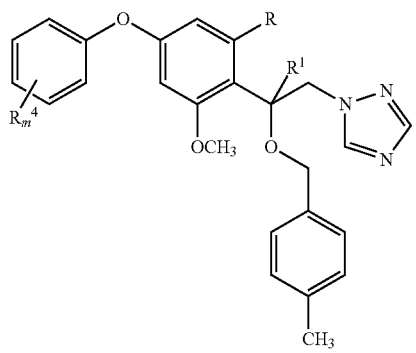
I.H10

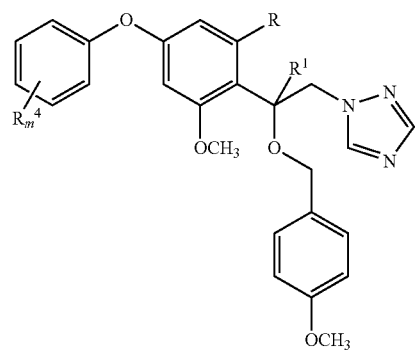
I.J10

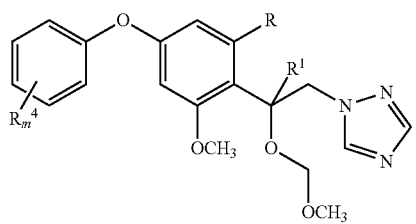
I.K10

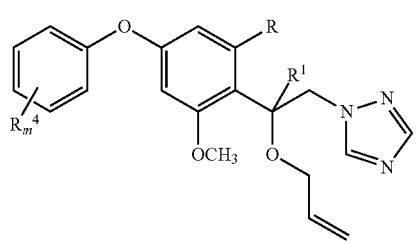
I.L10

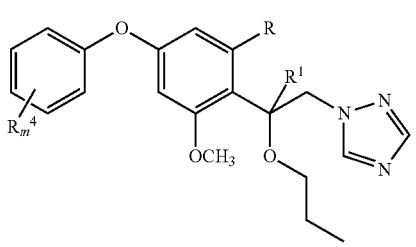
I.M10

-continued

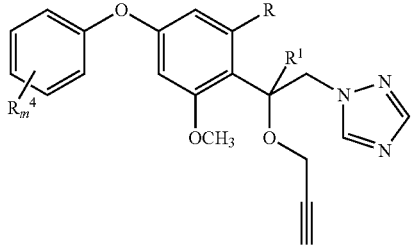
I.N10

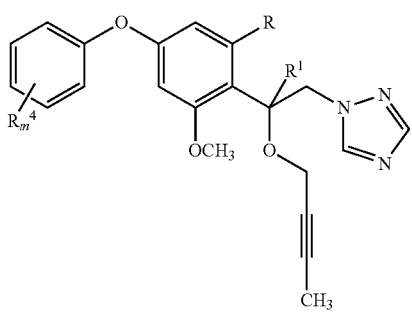
I.O10

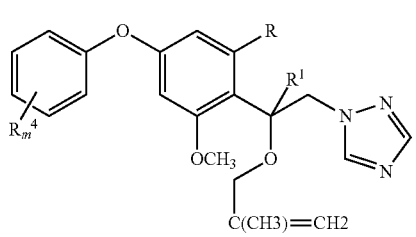
I.P10

Further embodiments of the present invention are compounds I, wherein $R^3{}_n$ is meta-OCH$_3$ (meta in relation to the linkage of the alcohol group to the phenyl ring) and $R^2$ is hydrogen, methyl, ethyl, isopropyl, CH$_2$-phenyl, CH$_2$-(4-Cl-phenyl), CH$_2$-(4-F-phenyl), CH$_2$-(4-CH$_3$-phenyl), CH$_2$-(4-OCH$_3$-phenyl), CH$_2$—OCH$_3$, CH$_2$—CH=CH$_2$, n-propyl, CH$_2$—C≡C—H, CH$_2$—C≡C—CH$_3$ or CH$_2$C(CH$_3$)=CH$_2$, which compounds are of formulae I.A11, I.B11, I.C11, I.D11, I.E11, I.F11, I.G11, I.H11, I.J11, I.K11, I.L11, I.M11, I.N11, I.O11 and I.P11 respectively:

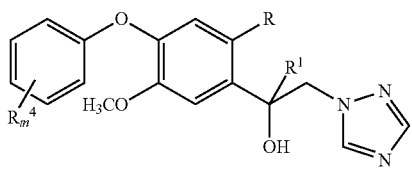
I.A11

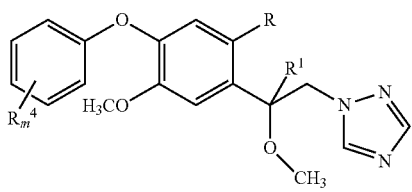
I.B11

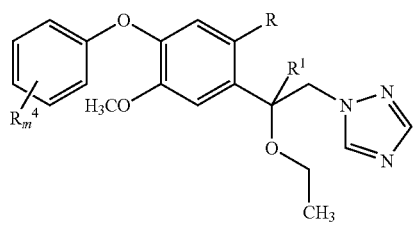
I.C10
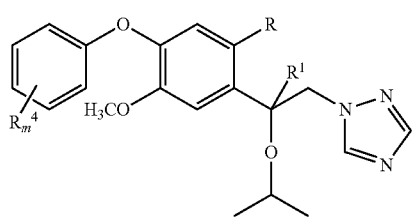
I.D11
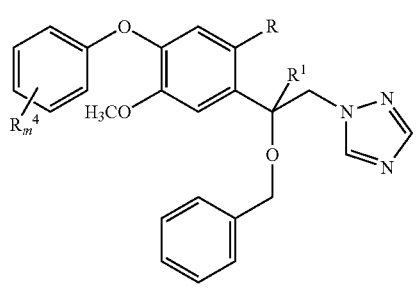
I.E11
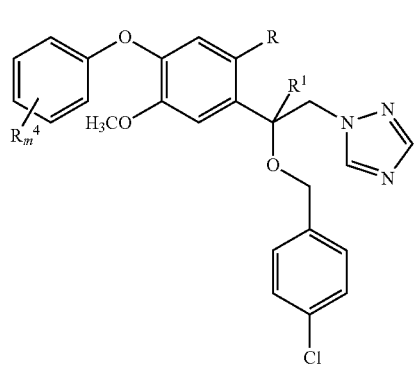
I.F11
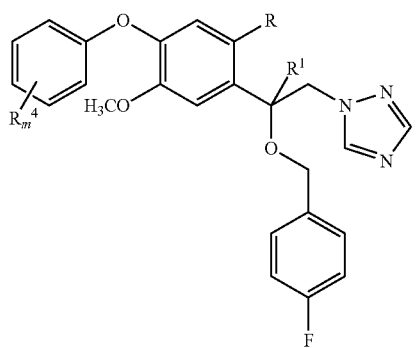
I.G11
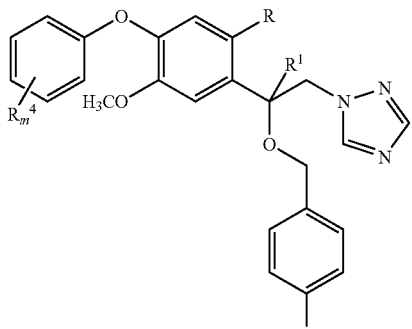
I.H11
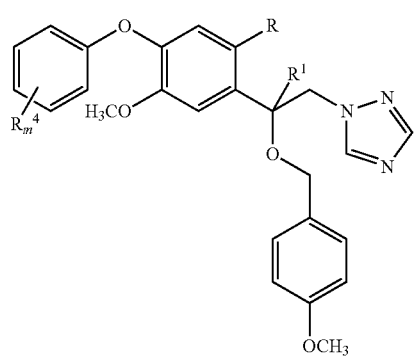
I.J11
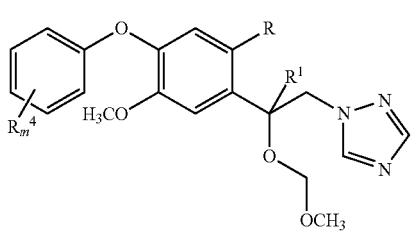
I.K11
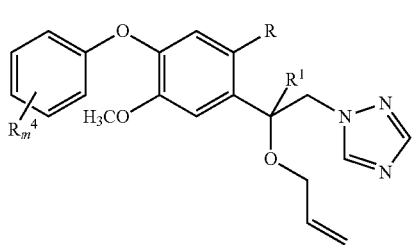
I.L11
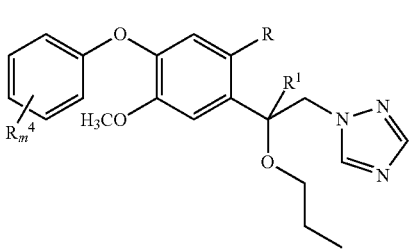
I.M11

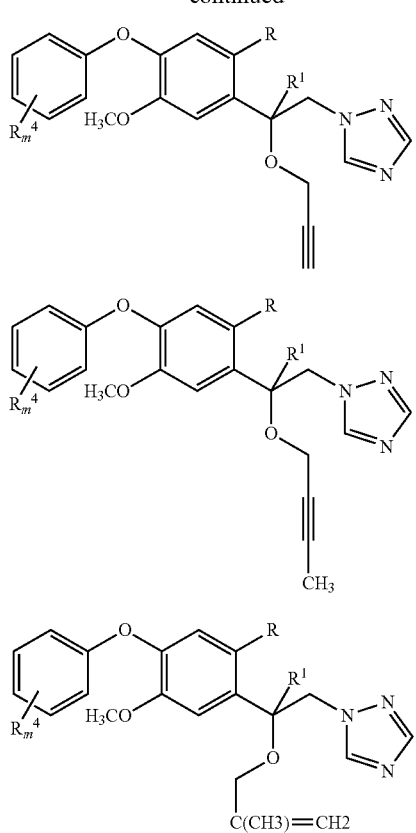

Further preferred embodiments of the present are, in particular with respect to their use, compounds of formulae I.A1, I.B1, I.C1, I.D1, I.E1, I.F1, I.G1, I.H1, I.J1, I.K1, I.L1, I.M1, I.N1, I.O1, I.P1; I.A2, I.B2, I.C2, I.D2, I.E2, I.F2, I.G2, I.H2, I.J2, I.K2, I.L2, I.M2, I.N2, I.O2, I.P2; I.A3, I.B3, I.C3, I.D3, I.E3, I.F3, I.G3, I.H3, I.J3, I.K3, I.L3, I.M3, I.N3, I.O3, I.P3; I.A4, I.B4, I.C4, I.D4, I.E4, I.F4, I.G4, I.H4, I.J4, I.K4, I.L4, I.M4, I.N4, I.O4, I.P4; I.A5, I.B5, I.C5, I.D5, I.E5, I.F5, I.G5, I.H5, I.J5, I.K5, I.L5, I.M5, I.N5, I.O5, I.P5; I.A6, I.B6, I.C6, I.D6, I.E6, I.F6, I.G6, I.H6, I.J6, I.K6, I.L6, I.M6, I.N6, I.O6, I.P6; I.A7, I.B7, I.C7, I.D7, I.E7, I.F7, I.G7, I.H7, I.J7, I.K7, I.L7, I.M7, I.N7, I.O7, I.P7; I.A8, I.B8, I.C8, I.D8, I.E8, I.F8, I.G8, I.H8, I.J8, I.K8, I.L8, I.M8, I.N8, I.O8, I.P8; I.A9, I.B9, I.C9, I.D9, I.E9, I.F9, I.G9, I.H9, I.J9, I.K9, I.L9, I.M9, I.N9, I.O9, I.P9; I.A10, I.B10, I.C10, I.D10, I.E10, I.F10, I.G10, I.H10, I.J10, I.K10, I.L10, I.M10, I.N10, I.O10, I.P10 and I.A11, I.B11, I.C11, I.D11, I.E11, I.F11, I.G11, I.H11, I.J11, I.K11, I.L11, I.M11, I.N11, I.O11, I.P11 compiled in tables 73 to 237 and tables 73a to 237a below. Here, the groups mentioned in the Tables for a substituent are furthermore, independently of the combination wherein they are mentioned, a particularly preferred embodiment of the substituent in question for the compounds 1 and any intermediate, respectively.

The compound names of the respective individual compounds disclosed in said tables can be derived as follows: For example, compound I.C1-75A1-375 is the inventive compound I.C1 (formula see above), wherein the substituent R is $CF_3$ (as defined in Table75) and wherein the meaning of $R^4_m$ and $R^1$ is given in line 375 of A1 $R^4_m$ is 3-Cl and $R^1$ is n-butyl.

Table 73 Compounds I.A1, wherein R is $CF_3$, and wherein the combination of $R^4_n$ and $R^1$ for each compound corresponds to one line of lines 373 to 1085 of Table A1 (Compounds I.A1-73A1-373 to I.A1-73A1-1085)

Table 74 Compounds I.B1, wherein R is $CF_3$, and wherein the combination of $R^4_n$ and $R^1$ for each compound corresponds to one line of lines 373 to 1085 of Table A1 (Compounds I.B1-74A1-373 to I.B1-74A1-1085)

Table 75 Compounds I.C1, wherein R is $CF_3$, and wherein the combination of $R^4_n$ and $R^1$ for each compound corresponds to one line of lines 373 to 1085 of Table A1 (Compounds I.C1-75A1-373 to I.C1-75A1-1085)

Table 76 Compounds I.D1, wherein R is $CF_3$, and wherein the combination of $R^4_n$ and $R^1$ for each compound corresponds to one line of lines 1 to 1085 of Table A1 (Compounds I.D1-76A1-1 to I.D1-76A1-1085)

Table 77 Compounds I.E1, wherein R is $CF_3$, and wherein the combination of $R^4_n$ and $R^1$ for each compound corresponds to one line of lines 1 to 1085 of Table A1 (Compounds I.E1-77-1 to I.E1-77A1-1085)

Table 78 Compounds I.F1, wherein R is $CF_3$, and wherein the combination of $R^4_n$ and $R^1$ for each compound corresponds to one line of lines 1 to 1085 of Table A1 (Compounds I.F1-78A1-1 to I.F1-78A1-1085)

Table 79 Compounds I.G1, wherein R is $CF_3$, and wherein the combination of $R^4_n$ and $R^1$ for each compound corresponds to one line of lines 1 to 1085 of Table A1 (Compounds I.G1-79A1-1 to I.G1-79A1-1085)

Table 80 Compounds I.H1, wherein R is $CF_3$, and wherein the combination of $R^4_n$ and $R^1$ for each compound corresponds to one line of lines 1 to 1085 of Table A1 (Compounds I.H1-80A1-1 to I.H1-80A1-1085)

Table 81 Compounds I.J1, wherein R is $CF_3$, and wherein the combination of $R^4_n$ and $R^1$ for each compound corresponds to one line of lines 1 to 1085 of Table A1 (Compounds I.J1-81A1-1 to I.J1-81A1-1085)

Table 82 Compounds I.K1, wherein R is $CF_3$, and wherein the combination of $R^4_n$ and $R^1$ for each compound corresponds to one line of lines 1 to 1085 of Table A1 (Compounds I.K1-82A1-1 to I.K1-82A1-1085)

Table 83 Compounds I.L1, wherein R is $CF_3$, and wherein the combination of $R^4_n$ and $R^1$ for each compound corresponds to one line of lines 1 to 1085 of Table A1 (Compounds I.L1-83A1-1 to I.L1-83A1-1085)

Table 84 Compounds I.M1, wherein R is $CF_3$, and wherein the combination of $R^4_n$ and $R^1$ for each compound corresponds to one line of lines 1 to 1085 of Table A1 (Compounds I.M1-84A1-1 to I.M1-84A1-1085)

Table 85 Compounds I.N1, wherein R is $CF_3$, and wherein the combination of $R^4_n$ and $R^1$ for each compound corresponds to one line of lines 1 to 1085 of Table A1 (Compounds I.N1-85A1-1 to I.N1-85A1-1085)

Table 86 Compounds I.O1, wherein R is $CF_3$, and wherein the combination of $R^4_n$ and $R^1$ for each compound corresponds to one line of lines 1 to 1085 of Table A1 (Compounds I.O1-86A1-1 to I.O1-86A1-1085)

Table 87 Compounds I.P1, wherein R is $CF_3$, and wherein the combination of $R^4_n$ and $R^1$ for each compound corresponds to one line of lines 1 to 1085 of Table A1 (Compounds I.P1-87A1-1 to I.P1-87A1-1085)

Table 88 Compounds I.A2, wherein R is $CF_3$, and wherein the combination of $R^4_n$ and $R^1$ for each compound corresponds to one line of lines 1 to 1085 of Table A1 (Compounds I.A2-88A1-1 to I.A2-88A1-1085)

Table 89 Compounds I.B2, wherein R is $CF_3$, and wherein the combination of $R^4_n$ and $R^1$ for each compound corresponds to one line of lines 1 to 1085 of Table A1 (Compounds I.B2-89A1-1 to I.B2-89A1-1085)

Table 90 Compounds I.C2, wherein R is $CF_3$, and wherein the combination of $R^4_n$ and $R^1$ for each compound corresponds to one line of lines 1 to 1085 of Table A1 (Compounds I.C2-90A1-1 to I.C2-90A1-1085)

Table 91 Compounds I.D2, wherein R is $CF_3$, and wherein the combination of $R^4_n$ and $R^1$ for each compound corresponds to one line of lines 1 to 1085 of Table A1 (Compounds I.D2-91A1-1 to I.D2-91-1085)

Table 92 Compounds I.E2, wherein R is $CF_3$, and wherein the combination of $R^4_n$ and $R^1$ for each compound corresponds to one line of lines 1 to 1085 of Table A1 (Compounds I.E2-92A1-1 to I.E2-92A1-1085)

Table 93 Compounds I.F2, wherein R is $CF_3$, and wherein the combination of $R^4_n$ and $R^1$ for each compound corresponds to one line of lines 1 to 1085 of Table A1 (Compounds I.F2-93A1-1 to I.F2-93A1-1085)

Table 94 Compounds I.G2, wherein R is $CF_3$, and wherein the combination of $R^4_n$ and $R^1$ for each compound corresponds to one line of lines 1 to 1085 of Table A1 (Compounds I.G2-94A1-1 to I.G2-94A1-1085)

Table 95 Compounds I.H2, wherein R is $CF_3$, and wherein the combination of $R^4_n$ and $R^1$ for each compound corresponds to one line of lines 1 to 1085 of Table A1 (Compounds I.H2-95A1-1 to I.H2-95A1-1085)

Table 96 Compounds I.J2, wherein R is $CF_3$, and wherein the combination of $R^4_n$ and $R^1$ for each compound corresponds to one line of lines 1 to 1085 of Table A1 (Compounds I.J2-96A1-1 to I.J2-96A1-1085)

Table 97 Compounds I.K2, wherein R is $CF_3$, and wherein the combination of $R^4_n$ and $R^1$ for each compound corresponds to one line of lines 1 to 1085 of Table A1 (Compounds I.K2-97A1-1 to I.K2-97A1-1085)

Table 98 Compounds I.L2, wherein R is $CF_3$, and wherein the combination of $R^4_n$ and $R^1$ for each compound corresponds to one line of lines 1 to 1085 of Table A1 (Compounds I.L2-98A1-1 to I.L2-98A1-1085)

Table 99 Compounds I.M2, wherein R is $CF_3$, and wherein the combination of $R^4_n$ and $R^1$ for each compound corresponds to one line of lines 1 to 1085 of Table A1 (Compounds I.M2-99A1-1 to I.M2-99A1-1085)

Table 100 Compounds I.N2, wherein R is $CF_3$, and wherein the combination of $R^4_n$ and $R^1$ for each compound corresponds to one line of lines 1 to 1085 of Table A1 (Compounds I.N2-100A1-1 to I.N2-100A1-1085)

Table 101 Compounds I.O2, wherein R is $CF_3$, and wherein the combination of $R^4_n$ and $R^1$ for each compound corresponds to one line of lines 1 to 1085 of Table A1 (Compounds I.O2-101A1-1 to I.O2-101A1-1085)

Table 102 Compounds I.P2, wherein R is $CF_3$, and wherein the combination of $R^4_n$ and $R^1$ for each compound corresponds to one line of lines 1 to 1085 of Table A1 (Compounds I.O2-102A1-1 to I.O2-102A1-1085)

Table 103 Compounds I.A3, wherein R is $CF_3$, and wherein the combination of $R^4_n$ and $R^1$ for each compound corresponds to one line of lines 1 to 1085 of Table A1 (Compounds I.A3-103A1-1 to I.A3-103A1-1085)

Table 104 Compounds I.B3, wherein R is $CF_3$, and wherein the combination of $R^4_n$ and $R^1$ for each compound corresponds to one line of lines 1 to 1085 of Table A1 (Compounds I.B3-104A1-1 to I.B3-104A1-1085)

Table 105 Compounds I.C3, wherein R is $CF_3$, and wherein the combination of $R^4_n$ and $R^1$ for each compound corresponds to one line of lines 1 to 1085 of Table A1 (Compounds I.C3-105A1-1 to I.C3-105A1-1085)

Table 106 Compounds I.D3, wherein R is $CF_3$, and wherein the combination of $R^4_n$ and $R^1$ for each compound corresponds to one line of lines 1 to 1085 of Table A1 (Compounds I.D3-106A1-1 to I.D3-106A1-1085)

Table 107 Compounds I.E3, wherein R is $CF_3$, and wherein the combination of $R^4_n$ and $R^1$ for each compound corresponds to one line of lines 1 to 1085 of Table A1 (Compounds I.E3-107A1-1 to I.E3-107A1-1085)

Table 108 Compounds I.F3, wherein R is $CF_3$, and wherein the combination of $R^4_n$ and $R^1$ for each compound corresponds to one line of lines 1 to 1085 of Table A1 (Compounds I.F3-108A1-1 to I.F3-108A1-1085)

Table 109 Compounds I.G3, wherein R is $CF_3$, and wherein the combination of $R^4_n$ and $R^1$ for each compound corresponds to one line of lines 1 to 1085 of Table A1 (Compounds I.G3-109A1-1 to I.G3-109A1-1085)

Table 110 Compounds I.H3, wherein R is $CF_3$, and wherein the combination of $R^4_n$ and $R^1$ for each compound corresponds to one line of lines 1 to 1085 of Table A1 (Compounds I.H3-110A1-1 to I.H3-110A1-1085)

Table 111 Compounds I.J3, wherein R is $CF_3$, and wherein the combination of $R^4_n$ and $R^1$ for each compound corresponds to one line of lines 1 to 1085 of Table A1 (Compounds I.J3-111A1-1 to I.J3-111A1-1085)

Table 112 Compounds I.K3, wherein R is $CF_3$, and wherein the combination of $R^4_n$ and $R^1$ for each compound corresponds to one line of lines 1 to 1085 of Table A1 (Compounds I.K3-112A1-1 to I.K3-112A1-1085)

Table 113 Compounds I.L3, wherein R is $CF_3$, and wherein the combination of $R^4_n$ and $R^1$ for each compound corresponds to one line of lines 1 to 1085 of Table A1 (Compounds I.L3-113A1-1 to I.L3-113A1-1085)

Table 114 Compounds I.M3, wherein R is $CF_3$, and wherein the combination of $R^4_n$ and $R^1$ for each compound corresponds to one line of lines 1 to 1085 of Table A1 (Compounds I.M3-114A1-1 to I.M3-114A1-1085)

Table 115 Compounds I.N3, wherein R is $CF_3$, and wherein the combination of $R^4_n$ and $R^1$ for each compound corresponds to one line of lines 1 to 1085 of Table A1 (Compounds I.N3-115A1-1 to I.N3-115A1-1085)

Table 116 Compounds I.O3, wherein R is $CF_3$, and wherein the combination of $R^4_n$ and $R^1$ for each compound corresponds to one line of lines 1 to 1085 of Table A1 (Compounds I.O3-116A1-1 to I.O3-116A1-1085)

Table 117 Compounds I.P3, wherein R is $CF_3$, and wherein the combination of $R^4_n$ and $R^1$ for each compound corresponds to one line of lines 1 to 1085 of Table A1 (Compounds I.P3-117A1-1 to I.P3-117A1-1085)

Table 118 Compounds I.A4, wherein R is $CF_3$, and wherein the combination of $R^4_n$ and $R^1$ for each compound corresponds to one line of lines 1 to 1085 of Table A1 (Compounds I.A4-118A1-1 to I.A4-118A1-1085)

Table 119 Compounds I.B4, wherein R is $CF_3$, and wherein the combination of $R^4_n$ and $R^1$ for each compound corresponds to one line of lines 1 to 1085 of Table A1 (Compounds I.B4-119A1-1 to I.B4-119A1-1085)

Table 120 Compounds I.C4, wherein R is $CF_3$, and wherein the combination of $R^4_n$ and $R^1$ for each compound corresponds to one line of lines 1 to 1085 of Table A1 (Compounds I.C4-120A1-1 to I.C4-120A1-1085)

Table 121 Compounds I.D4, wherein R is $CF_3$, and wherein the combination of $R^4_n$ and $R^1$ for each compound corresponds to one line of lines 1 to 1085 of Table A1 (Compounds I.D4-121A1-1 to I.D4-121A1-1085)

Table 122 Compounds I.E4, wherein R is $CF_3$, and wherein the combination of $R^4_n$ and $R^1$ for each compound corresponds to one line of lines 1 to 1085 of Table A1 (Compounds I.E4-122A1-1 to I.E4-122A1-1085)

Table 123 Compounds I.F4, wherein R is $CF_3$, and wherein the combination of $R^4_n$ and $R^1$ for each compound corresponds to one line of lines 1 to 1085 of Table A1 (Compounds I.F4-123A1-1 to I.F4-123A1-1085)

Table 124 Compounds I.G4, wherein R is $CF_3$, and wherein the combination of $R^4_n$ and $R^1$ for each compound corresponds to one line of lines 1 to 1085 of Table A1 (Compounds I.G4-124A1-1 to I.G4-124A1-1085)

Table 125 Compounds I.H4, wherein R is $CF_3$, and wherein the combination of $R^4_n$ and $R^1$ for each compound corresponds to one line of lines 1 to 1085 of Table A1 (Compounds I.H4-125A1-1 to I.H4-125A1-1085)

Table 126 Compounds I.J4, wherein R is $CF_3$, and wherein the combination of $R^4_n$ and $R^1$ for each compound corresponds to one line of lines 1 to 1085 of Table A1 (Compounds I.J4-126A1-1 to I.J4-126A1-1085)

Table 127 Compounds I.K4, wherein R is $CF_3$, and wherein the combination of $R^4_n$ and $R^1$ for each compound corresponds to one line of lines 1 to 1085 of Table A1 (Compounds I.K4-127A1-1 to I.K4-127A1-1085)

Table 128 Compounds I.L4, wherein R is $CF_3$, and wherein the combination of $R^4_n$ and $R^1$ for each compound corresponds to one line of lines 1 to 1085 of Table A1 (Compounds I.L4-128A1-1 to I.L4-128A1-1085)

Table 129 Compounds I.M4, wherein R is $CF_3$, and wherein the combination of $R^4_n$ and $R^1$ for each compound corresponds to one line of lines 1 to 1085 of Table A1 (Compounds I.M4-129A1-1 to I.M4-129A1-1085)

Table 130 Compounds I.N4, wherein R is $CF_3$, and wherein the combination of $R^4_n$ and $R^1$ for each compound corresponds to one line of lines 1 to 1085 of Table A1 (Compounds I.N4-130A1-1 to I.N4-130A1-1085)

Table 131 Compounds I.O4, wherein R is $CF_3$, and wherein the combination of $R^4_n$ and $R^1$ for each compound corresponds to one line of lines 1 to 1085 of Table A1 (Compounds I.O4-131A1-1 to I.O4-131A1-1085)

Table 132 Compounds I.P4, wherein R is $CF_3$, and wherein the combination of $R^4_n$ and $R^1$ for each compound corresponds to one line of lines 1 to 1085 of Table A1 (Compounds I.P4-132A1-1 to I.P4-132A1-1085)

Table 133 Compounds I.A5, wherein R is $CF_3$, and wherein the combination of $R^4_n$ and $R^1$ for each compound corresponds to one line of lines 1 to 1085 of Table A1 (Compounds I.A5-133A1-1 to I.A5-133A1-1085)

Table 134 Compounds I.B5, wherein R is $CF_3$, and wherein the combination of $R^4_n$ and $R^1$ for each compound corresponds to one line of lines 1 to 1085 of Table A1 (Compounds I.B5-134A1-1 to I.B5-134A1-1085)

Table 135 Compounds I.C5, wherein R is $CF_3$, and wherein the combination of $R^4_n$ and $R^1$ for each compound corresponds to one line of lines 1 to 1085 of Table A1 (Compounds I.C5-135A1-1 to I.C5-135A1-1085)

Table 136 Compounds I.D5, wherein R is $CF_3$, and wherein the combination of $R^4_n$ and $R^1$ for each compound corresponds to one line of lines 1 to 1085 of Table A1 (Compounds I.D5-136A1-1 to I.D5-136A1-1085)

Table 137 Compounds I.E5, wherein R is $CF_3$, and wherein the combination of $R^4_n$ and $R^1$ for each compound corresponds to one line of lines 1 to 1085 of Table A1 (Compounds I.E5-137A1-1 to I.E5-137A1-1085)

Table 138 Compounds I.F5, wherein R is $CF_3$, and wherein the combination of $R^4_n$ and $R^1$ for each compound corresponds to one line of lines 1 to 1085 of Table A1 (Compounds I.F5-138A1-1 to I.F5-138A1-1085)

Table 139 Compounds I.G5, wherein R is $CF_3$, and wherein the combination of $R^4_n$ and $R^1$ for each compound corresponds to one line of lines 1 to 1085 of Table A1 (Compounds I.G5-139A1-1 to I.G5-139A1-1085)

Table 140 Compounds I.H5, wherein R is $CF_3$, and wherein the combination of $R^4_n$ and $R^1$ for each compound corresponds to one line of lines 1 to 1085 of Table A1 (Compounds I.H5-140A1-1 to I.H5-140A1-1085)

Table 141 Compounds I.J5, wherein R is $CF_3$, and wherein the combination of $R^4_n$ and $R^1$ for each compound corresponds to one line of lines 1 to 1085 of Table A1 (Compounds I.J5-141A1-1 to I.J5-141A1-1085)

Table 142 Compounds I.K5, wherein R is $CF_3$, and wherein the combination of $R^4_n$ and $R^1$ for each compound corresponds to one line of lines 1 to 1085 of Table A1 (Compounds I.K5-142A1-1 to I.K5-142A1-1085)

Table 143 Compounds I.L5, wherein R is $CF_3$, and wherein the combination of $R^4_n$ and $R^1$ for each compound corresponds to one line of lines 1 to 1085 of Table A1 (Compounds I.L5-143A1-1 to I.L5-143A1-1085)

Table 144 Compounds I.M5, wherein R is $CF_3$, and wherein the combination of $R^4_n$ and $R^1$ for each compound corresponds to one line of lines 1 to 1085 of Table A1 (Compounds I.M5-144A1-1 to I.M5-144A1-1085)

Table 145 Compounds I.N5, wherein R is $CF_3$, and wherein the combination of $R^4_n$ and $R^1$ for each compound corresponds to one line of lines 1 to 1085 of Table A1 (Compounds I.N5-145A1-1 to I.N5-145A1-1085)

Table 146 Compounds I.O5, wherein R is $CF_3$, and wherein the combination of $R^4_n$ and $R^1$ for each compound corresponds to one line of lines 1 to 1085 of Table A1 (Compounds I.O5-146A1-1 to I.O5-146A1-1085)

Table 147 Compounds I.P5, wherein R is $CF_3$, and wherein the combination of $R^4_n$ and $R^1$ for each compound corresponds to one line of lines 1 to 1085 of Table A1 (Compounds I.P5-147A1-1 to I.P5-147A1-1085)

Table 148 Compounds I.A6, wherein R is $CF_3$, and wherein the combination of $R^4_n$ and $R^1$ for each compound corresponds to one line of lines 1 to 1085 of Table A1 (Compounds I.A6-148A1-1 to I.A6-148A1-1085)

Table 149 Compounds I.B6, wherein R is $CF_3$, and wherein the combination of $R^4_n$ and $R^1$ for each compound corresponds to one line of lines 1 to 1085 of Table A1 (Compounds I.B6-149A1-1 to I.B6-149A1-1085)

Table 150 Compounds I.C6, wherein R is $CF_3$, and wherein the combination of $R^4_n$ and $R^1$ for each compound corresponds to one line of lines 1 to 1085 of Table A1 (Compounds I.C6-150A1-1 to I.C6-150A1-1085)

Table 151 Compounds I.D6, wherein R is $CF_3$, and wherein the combination of $R^4_n$ and $R^1$ for each compound corresponds to one line of lines 1 to 1085 of Table A1 (Compounds I.D6-151A1-1 to I.D6-151A1-1085)

Table 152 Compounds I.E6, wherein R is $CF_3$, and wherein the combination of $R^4_n$ and $R^1$ for each compound corresponds to one line of lines 1 to 1085 of Table A1 (Compounds I.E6-152A1-1 to I.E6-152A1-1085)

Table 153 Compounds I.F6, wherein R is $CF_3$, and wherein the combination of $R^4_n$ and $R^1$ for each compound corresponds to one line of lines 1 to 1085 of Table A1 (Compounds I.F6-153A1-1 to I.F6-153A1-1085)

Table 154 Compounds I.G6, wherein R is $CF_3$, and wherein the combination of $R^4_n$ and $R^1$ for each compound corresponds to one line of lines 1 to 1085 of Table A1 (Compounds I.G6-154A1-1 to I.G6-154A1-1085)

Table 155 Compounds I.H6, wherein R is $CF_3$, and wherein the combination of $R^4_n$ and $R^1$ for each compound corresponds to one line of lines 1 to 1085 of Table A1 (Compounds I.H6-155A1-1 to I.H6-155A1-1085)

Table 156 Compounds I.J6, wherein R is $CF_3$, and wherein the combination of $R^4_n$ and $R^1$ for each compound corresponds to one line of lines 1 to 1085 of Table A1 (Compounds I.J6-156A1-1 to I.J6-156A1-1085)

Table 157 Compounds I.K6, wherein R is $CF_3$, and wherein the combination of $R^4_n$ and $R^1$ for each compound corresponds to one line of lines 1 to 1085 of Table A1 (Compounds I.K6-157A1-1 to I.K6-157A1-1085)

Table 158 Compounds I.L6, wherein R is $CF_3$, and wherein the combination of $R^4_n$ and $R^1$ for each compound corresponds to one line of lines 1 to 1085 of Table A1 (Compounds I.L6-158A1-1 to I.L6-158A1-1085)

Table 159 Compounds I.M6, wherein R is $CF_3$, and wherein the combination of $R^4_n$ and $R^1$ for each compound corresponds to one line of lines 1 to 1085 of Table A1 (Compounds I.M6-159A1-1 to I.M6-159A1-1085)

Table 160 Compounds I.N6, wherein R is $CF_3$, and wherein the combination of $R^4_n$ and $R^1$ for each compound corresponds to one line of lines 1 to 1085 of Table A1 (Compounds I.N6-160A1-1 to I.N6-160A1-1085)

Table 161 Compounds I.O6, wherein R is $CF_3$, and wherein the combination of $R^4_n$ and $R^1$ for each compound corresponds to one line of lines 1 to 1085 of Table A1 (Compounds I.O6-161A1-1 to I.O6-161A1-1085)

Table 162 Compounds I.P6, wherein R is $CF_3$, and wherein the combination of $R^4_n$ and $R^1$ for each compound corresponds to one line of lines 1 to 1085 of Table A1 (Compounds I.P6-162A1-1 to I.P6-162A1-1085)

Table 163 Compounds I.A7, wherein R is $CF_3$, and wherein the combination of $R^4_n$ and $R^1$ for each compound corresponds to one line of lines 1 to 1085 of Table A1 (Compounds I.A7-163A1-1 to I.A7-163A1-1085)

Table 164 Compounds I.B7, wherein R is $CF_3$, and wherein the combination of $R^4_n$ and $R^1$ for each compound corresponds to one line of lines 1 to 1085 of Table A1 (Compounds I.B7-164A1-1 to I.B7-164A1-1085)

Table 165 Compounds I.C7, wherein R is $CF_3$, and wherein the combination of $R^4_n$ and $R^1$ for each compound corresponds to one line of lines 1 to 1085 of Table A1 (Compounds I.C7-165A1-1 to I.C7-165A1-1085)

Table 166 Compounds I.D7, wherein R is $CF_3$, and wherein the combination of $R^4_n$ and $R^1$ for each compound corresponds to one line of lines 1 to 1085 of Table A1 (Compounds I.D7-166A1-1 to I.D7-166A1-1085)

Table 167 Compounds I.E7, wherein R is $CF_3$, and wherein the combination of $R^4_n$ and $R^1$ for each compound corresponds to one line of lines 1 to 1085 of Table A1 (Compounds I.E7-167A1-1 to I.E7-167A1-1085)

Table 168 Compounds I.F7, wherein R is $CF_3$, and wherein the combination of $R^4_n$ and $R^1$ for each compound corresponds to one line of lines 1 to 1085 of Table A1 (Compounds I.F7-168A1-1 to I.F7-168A1-1085)

Table 169 Compounds I.G7, wherein R is $CF_3$, and wherein the combination of $R^4_n$ and $R^1$ for each compound corresponds to one line of lines 1 to 1085 of Table A1 (Compounds I.G7-169A1-1 to I.G7-169A1-1085)

Table 170 Compounds I.H7, wherein R is $CF_3$, and wherein the combination of $R^4_n$ and $R^1$ for each compound corresponds to one line of lines 1 to 1085 of Table A1 (Compounds I.H7-170A1-1 to I.H7-170A1-1085)

Table 171 Compounds I.J7, wherein R is $CF_3$, and wherein the combination of $R^4_n$ and $R^1$ for each compound corresponds to one line of lines 1 to 1085 of Table A1 (Compounds I.J7-171A1-1 to I.J7-171A1-1085)

Table 172 Compounds I.K7, wherein R is $CF_3$, and wherein the combination of $R^4_n$ and $R^1$ for each compound corresponds to one line of lines 1 to 1085 of Table A1 (Compounds I.K7-172A1-1 to I.K7-172A1-1085)

Table 173 Compounds I.L7, wherein R is $CF_3$, and wherein the combination of $R^4_n$ and $R^1$ for each compound corresponds to one line of lines 1 to 1085 of Table A1 (Compounds I.L7-173A1-1 to I.L7-173A1-1085)

Table 174 Compounds I.M7, wherein R is $CF_3$, and wherein the combination of $R^4_n$ and $R^1$ for each compound corresponds to one line of lines 1 to 1085 of Table A1 (Compounds I.M7-174A1-1 to I.M7-174A1-1085)

Table 175 Compounds I.N7, wherein R is $CF_3$, and wherein the combination of $R^4_n$ and $R^1$ for each compound corresponds to one line of lines 1 to 1085 of Table A1 (Compounds I.N7-175A1-1 to I.N7-175A1-1085)

Table 176 Compounds I.O7, wherein R is $CF_3$, and wherein the combination of $R^4_n$ and $R^1$ for each compound corresponds to one line of lines 1 to 1085 of Table A1 (Compounds I.O7-176A1-1 to I.O7-176A1-1085)

Table 177 Compounds I.P7, wherein R is $CF_3$, and wherein the combination of $R^4_n$ and $R^1$ for each compound corresponds to one line of lines 1 to 1085 of Table A1 (Compounds I.P7-177A1-1 to I.P7-177A1-1085)

Table 178 Compounds I.A8, wherein R is $CF_3$, and wherein the combination of $R^4_n$ and $R^1$ for each compound corresponds to one line of lines 1 to 1085 of Table A1 (Compounds I.A8-178A1-1 to I.A8-178A1-1085)

Table 179 Compounds I.B8, wherein R is $CF_3$, and wherein the combination of $R^4_n$ and $R^1$ for each compound corresponds to one line of lines 1 to 1085 of Table A1 (Compounds I.B8-179A1-1 to I.B8-179A1-1085)

Table 180 Compounds I.C8, wherein R is $CF_3$, and wherein the combination of $R^4_n$ and $R^1$ for each compound corresponds to one line of lines 1 to 1085 of Table A1 (Compounds I.C8-180A1-1 to I.C8-180A1-1085)

Table 181 Compounds I.D8, wherein R is $CF_3$, and wherein the combination of $R^4_n$ and $R^1$ for each compound corresponds to one line of lines 1 to 1085 of Table A1 (Compounds I.D8-181A1-1 to I.D8-181A1-1085)

Table 182 Compounds I.E8, wherein R is $CF_3$, and wherein the combination of $R^4_n$ and $R^1$ for each compound corresponds to one line of lines 1 to 1085 of Table A1 (Compounds I.E8-182A1-1 to I.E8-182A1-1085)

Table 183 Compounds I.F8, wherein R is $CF_3$, and wherein the combination of $R^4_n$ and $R^1$ for each compound corresponds to one line of lines 1 to 1085 of Table A1 (Compounds I.F8-183A1-1 to I.F8-183A1-1085)

Table 184 Compounds I.G8, wherein R is $CF_3$, and wherein the combination of $R^4_n$ and $R^1$ for each compound corresponds to one line of lines 1 to 1085 of Table A1 (Compounds I.G8-184A1-1 to I.G8-184A1-1085)

Table 185 Compounds I.H8, wherein R is $CF_3$, and wherein the combination of $R^4_n$ and $R^1$ for each compound corresponds to one line of lines 1 to 1085 of Table A1 (Compounds I.H8-185A1-1 to I.H8-185A1-1085)

Table 186 Compounds I.J8, wherein R is $CF_3$, and wherein the combination of $R^4_n$ and $R^1$ for each compound corresponds to one line of lines 1 to 1085 of Table A1 (Compounds I.J8-186A1-1 to I.J8-186A1-1085)

Table 187 Compounds I.K8, wherein R is $CF_3$, and wherein the combination of $R^4_n$ and $R^1$ for each compound corresponds to one line of lines 1 to 1085 of Table A1 (Compounds I.K8-187A1-1 to I.K8-187A1-1085)

Table 188 Compounds I.L8, wherein R is $CF_3$, and wherein the combination of $R^4_n$ and $R^1$ for each compound corresponds to one line of lines 1 to 1085 of Table A1 (Compounds I.L8-188A1-1 to I.L8-188A1-1085)

Table 189 Compounds I.M8, wherein R is $CF_3$, and wherein the combination of $R^4_n$ and $R^1$ for each compound corresponds to one line of lines 1 to 1085 of Table A1 (Compounds I.M8-189A1-1 to I.M8-189A1-1085)

Table 190 Compounds I.N8, wherein R is $CF_3$, and wherein the combination of $R^4_n$ and $R^1$ for each compound corresponds to one line of lines 1 to 1085 of Table A1 (Compounds I.N8-190A1-1 to I.N8-190A1-1085)

Table 191 Compounds I.O8, wherein R is $CF_3$, and wherein the combination of $R^4_n$ and $R^1$ for each compound corresponds to one line of lines 1 to 1085 of Table A1 (Compounds I.O8-191A1-1 to I.O8-191A1-1085)

Table 192 Compounds I.P8, wherein R is $CF_3$, and wherein the combination of $R^4_n$ and $R^1$ for each compound corresponds to one line of lines 1 to 1085 of Table A1 (Compounds I.P8-192A1-1 to I.P8-192A1-1085)

Table 193 Compounds I.A9, wherein R is $CF_3$, and wherein the combination of $R^4_n$ and $R^1$ for each compound corresponds to one line of lines 1 to 1085 of Table A1 (Compounds I.A9-193A1-1 to I.A9-193A1-1085)

Table 194 Compounds I.B9, wherein R is $CF_3$, and wherein the combination of $R^4_n$ and $R^1$ for each compound corresponds to one line of lines 1 to 1085 of Table A1 (Compounds I.B9-194A1-1 to I.B9-194A1-1085)

Table 195 Compounds I.C9, wherein R is $CF_3$, and wherein the combination of $R^4_n$ and $R^1$ for each compound corresponds to one line of lines 1 to 1085 of Table A1 (Compounds I.C9-195A1-1 to I.C9-195A1-1085)

Table 196 Compounds I.D9, wherein R is $CF_3$, and wherein the combination of $R^4_n$ and $R^1$ for each compound corresponds to one line of lines 1 to 1085 of Table A1 (Compounds I.D9-196A1-1 to I.D9-196A1-1085)

Table 197 Compounds I.E9, wherein R is $CF_3$, and wherein the combination of $R^4{}_n$ and $R^1$ for each compound corresponds to one line of lines 1 to 1085 of Table A1 (Compounds I.E9-197A1-1 to I.E9-197A1-1085)

Table 198 Compounds I.F9, wherein R is $CF_3$, and wherein the combination of $R^4{}_n$ and $R^1$ for each compound corresponds to one line of lines 1 to 1085 of Table A1 (Compounds I.F9-198A1-1 to I.F9-198A1-1085)

Table 199 Compounds I.G9, wherein R is $CF_3$, and wherein the combination of $R^4{}_n$ and $R^1$ for each compound corresponds to one line of lines 1 to 1085 of Table A1 (Compounds I.G9-199A1-1 to I.G9-199A1-1085)

Table 200 Compounds I.H9, wherein R is $CF_3$, and wherein the combination of $R^4{}_n$ and $R^1$ for each compound corresponds to one line of lines 1 to 1085 of Table A1 (Compounds I.H9-200A1-1 to I.H9-200A1-1085)

Table 201 Compounds I.J9, wherein R is $CF_3$, and wherein the combination of $R^4{}_n$ and $R^1$ for each compound corresponds to one line of lines 1 to 1085 of Table A1 (Compounds I.J9-201A1-1 to I.J9-201A1-1085)

Table 202 Compounds I.K9, wherein R is $CF_3$, and wherein the combination of $R^4{}_n$ and $R^1$ for each compound corresponds to one line of lines 1 to 1085 of Table A1 (Compounds I.K9-202A1-1 to I.K9-202A1-1085)

Table 203 Compounds I.L9, wherein R is $CF_3$, and wherein the combination of $R^4{}_n$ and $R^1$ for each compound corresponds to one line of lines 1 to 1085 of Table A1 (Compounds I.L9-203A1-1 to I.L9-203A1-1085)

Table 204 Compounds I.M9, wherein R is $CF_3$, and wherein the combination of $R^4{}_n$ and $R^1$ for each compound corresponds to one line of lines 1 to 1085 of Table A1 (Compounds I.M9-204A1-1 to I.M9-204A1-1085)

Table 205 Compounds I.N9, wherein R is $CF_3$, and wherein the combination of $R^4{}_n$ and $R^1$ for each compound corresponds to one line of lines 1 to 1085 of Table A1 (Compounds I.N9-205A1-1 to I.N9-205A1-1085)

Table 206 Compounds I.O9, wherein R is $CF_3$, and wherein the combination of $R^4{}_n$ and $R^1$ for each compound corresponds to one line of lines 1 to 1085 of Table A1 (Compounds I.O9-206A1-1 to I.O9-206A1-1085)

Table 207 Compounds I.P9, wherein R is $CF_3$, and wherein the combination of $R^4{}_n$ and $R^1$ for each compound corresponds to one line of lines 1 to 1085 of Table A1 (Compounds I.P9-207A1-1 to I.P9-207A1-1085)

Table 208 Compounds I.A10, wherein R is $CF_3$, and wherein the combination of $R^4{}_n$ and $R^1$ for each compound corresponds to one line of lines 1 to 1085 of Table A1 (Compounds I.A10-208A1-1 to I.A10-208A1-1085)

Table 209 Compounds I.B10, wherein R is $CF_3$, and wherein the combination of $R^4{}_n$ and $R^1$ for each compound corresponds to one line of lines 1 to 1085 of Table A1 (Compounds I.B10-209A1-1 to I.B10-209A1-1085)

Table 210 Compounds I.C10, wherein R is $CF_3$, and wherein the combination of $R^4{}_n$ and $R^1$ for each compound corresponds to one line of lines 1 to 1085 of Table A1 (Compounds I.B10-210A1-1 to I.C10-210A1-1085)

Table 211 Compounds I.D10, wherein R is $CF_3$, and wherein the combination of $R^4{}_n$ and $R^1$ for each compound corresponds to one line of lines 1 to 1085 of Table A1 (Compounds I.D10-211A1-1 to I.D10-211A1-1085)

Table 212 Compounds I.E10, wherein R is $CF_3$, and wherein the combination of $R^4{}_n$ and $R^1$ for each compound corresponds to one line of lines 1 to 1085 of Table A1 (Compounds I.E10-212A1-1 to I.E10-212A1-1085)

Table 213 Compounds I.F10, wherein R is $CF_3$, and wherein the combination of $R^4{}_n$ and $R^1$ for each compound corresponds to one line of lines 1 to 1085 of Table A1 (Compounds I.F10-213A1-1 to I.F10-213A1-1085)

Table 214 Compounds I.G10, wherein R is $CF_3$, and wherein the combination of $R^4{}_n$ and $R^1$ for each compound corresponds to one line of lines 1 to 1085 of Table A1 (Compounds I.G10-214A1-1 to I.G10-214A1-1085)

Table 215 Compounds I.H10, wherein R is $CF_3$, and wherein the combination of $R^4{}_n$ and $R^1$ for each compound corresponds to one line of lines 1 to 1085 of Table A1 (Compounds I.H10-215A1-1 to I.H10-215A1-1085)

Table 216 Compounds I.J10, wherein R is $CF_3$, and wherein the combination of $R^4{}_n$ and $R^1$ for each compound corresponds to one line of lines 1 to 1085 of Table A1 (Compounds I.J10-216A1-1 to I.J10-216A1-1085)

Table 217 Compounds I.K10, wherein R is $CF_3$, and wherein the combination of $R^4{}_n$ and $R^1$ for each compound corresponds to one line of lines 1 to 1085 of Table A1 (Compounds I.K10-217A1-1 to I.K10-217A1-1085)

Table 218 Compounds I.L10, wherein R is $CF_3$, and wherein the combination of $R^4{}_n$ and $R^1$ for each compound corresponds to one line of lines 1 to 1085 of Table A1 (Compounds I.L10-218A1-1 to I.L10-218A1-1085)

Table 219 Compounds I.M10, wherein R is $CF_3$, and wherein the combination of $R^4{}_n$ and $R^1$ for each compound corresponds to one line of lines 1 to 1085 of Table A1 (Compounds I.M10-219A1-1 to I.M10-219A1-1085)

Table 220 Compounds I.N10, wherein R is $CF_3$, and wherein the combination of $R^4{}_n$ and $R^1$ for each compound corresponds to one line of lines 1 to 1085 of Table A1 (Compounds I.N10-220A1-1 to I.N10-220A1-1085)

Table 221 Compounds I.O10, wherein R is $CF_3$, and wherein the combination of $R^4{}_n$ and $R^1$ for each compound corresponds to one line of lines 1 to 1085 of Table A1 (Compounds I.O10-221A1-1 to I.O10-221A1-1085)

Table 222 Compounds I.P10, wherein R is $CF_3$, and wherein the combination of $R^4{}_n$ and $R^1$ for each compound corresponds to one line of lines 1 to 1085 of Table A1 (Compounds I.P10-222A1-1 to I.P10-222A1-1085)

Table 223 Compounds I.A11, wherein R is CF$_3$, and wherein the combination of R$^4_n$ and R$^1$ for each compound corresponds to one line of lines 1 to 1085 of Table A1 (Compounds I.A11-223A1-1 to I.A11-223A1-1085)

Table 224 Compounds I.B11, wherein R is CF$_3$, and wherein the combination of R$^4_n$ and R$^1$ for each compound corresponds to one line of lines 1 to 1085 of Table A1 (Compounds I.B11-224A1-1 to I.B11-224A1-1085)

Table 225 Compounds I.C11, wherein R is CF$_3$, and wherein the combination of R$^4_n$ and R$^1$ for each compound corresponds to one line of lines 1 to 1085 of Table A1 (Compounds I.C11-225A1-1 to I.C11-225A1-1085)

Table 226 Compounds I.D11, wherein R is CF$_3$, and wherein the combination of R$^4_n$ and R$^1$ for each compound corresponds to one line of lines 1 to 1085 of Table A1 (Compounds I.D11-226A1-1 to I.D11-226A1-1085)

Table 227 Compounds I.E11, wherein R is CF$_3$, and wherein the combination of R$^4_n$ and R$^1$ for each compound corresponds to one line of lines 1 to 1085 of Table A1 (Compounds I.E11-227A1-1 to I.E11-227A1-1085)

Table 228 Compounds I.F11, wherein R is CF$_3$, and wherein the combination of R$^4_n$ and R$^1$ for each compound corresponds to one line of lines 1 to 1085 of Table A1 (Compounds I.F11-228A1-1 to I.F11-228A1-1085)

Table 229 Compounds I.G11, wherein R is CF$_3$, and wherein the combination of R$^4_n$ and R$^1$ for each compound corresponds to one line of lines 1 to 1085 of Table A1 (Compounds I.G11-229A1-1 to I.G11-229A1-1085)

Table 230 Compounds I.H11, wherein R is CF$_3$, and wherein the combination of R$^4_n$ and R$^1$ for each compound corresponds to one line of lines 1 to 1085 of Table A1 (Compounds I.H11-230A1-1 to I.H11-230A1-1085)

Table 231 Compounds I.J11, wherein R is CF$_3$, and wherein the combination of R$^4_n$ and R$^1$ for each compound corresponds to one line of lines 1 to 1085 of Table A1 (Compounds I.J11-231A1-1 to I.J11-231A1-1085)

Table 232 Compounds I.K11, wherein R is CF$_3$, and wherein the combination of R$^4_n$ and R$^1$ for each compound corresponds to one line of lines 1 to 1085 of Table A1 (Compounds I.K11-232A1-1 to I.K11-232A1-1085)

Table 233 Compounds I.L11, wherein R is CF$_3$, and wherein the combination of R$^4_n$ and R$^1$ for each compound corresponds to one line of lines 1 to 1085 of Table A1 (Compounds I.L11-233A1-1 to I.L11-233A1-1085)

Table 234 Compounds I.M11, wherein R is CF$_3$, and wherein the combination of R$^4_n$ and R$^1$ for each compound corresponds to one line of lines 1 to 1085 of Table A1 (Compounds I.M11-234A1-1 to I.M11-234A1-1085)

Table 235 Compounds I.N11, wherein R is CF$_3$, and wherein the combination of R$^4_n$ and R$^1$ for each compound corresponds to one line of lines 1 to 1085 of Table A1 (Compounds I.N11-235A1-1 to I.N11-235A1-1085)

Table 236 Compounds I.O11, wherein R is CF$_3$, and wherein the combination of R$^4_n$ and R$^1$ for each compound corresponds to one line of lines 1 to 1085 of Table A1 (Compounds I.O11-236A1-1 to I.O11-236A1-1085)

Table 237 Compounds I.P11, wherein R is CF$_3$, and wherein the combination of R$^4_n$ and R$^1$ for each compound corresponds to one line of lines 1 to 1085 of Table A1 (Compounds I.P11-237A1-1 to I.P11-237A1-1085)

Table 73a Compounds I.A1, wherein R is CF$_3$, and wherein the combination of R$^4_n$ and R$^1$ for each compound corresponds to one line of lines 373 to 1085 of Table A1 (Compounds I.A1-73aA1-373 to I.A1-73aA1-1085)

Table 74a Compounds I.B1, wherein R is CF$_3$, and wherein the combination of R$^4_n$ and R$^1$ for each compound corresponds to one line of lines 373 to 1085 of Table A1 (Compounds I.B1-74aA1-373 to I.B1-74aA1-1085)

Table 75a Compounds I.C1, wherein R is CF$_3$, and wherein the combination of R$^4_n$ and R$^1$ for each compound corresponds to one line of lines 373 to 1085 of Table A1 (Compounds I.C1-75aA1-373 to I.C1-75aA1-1085)

Table 76a Compounds I.D1, wherein R is CF$_3$, and wherein the combination of R$^4_n$ and R$^1$ for each compound corresponds to one line of lines 1 to 1085 of Table A1 (Compounds I.D1-76aA1-1 to I.D1-76aA1-1085)

Table 77a Compounds I.E1, wherein R is CF$_3$, and wherein the combination of R$^4_n$ and R$^1$ for each compound corresponds to one line of lines 1 to 1085 of Table A1 (Compounds I.E1-77-1 to I.E1-77aA1-1085)

Table 78a Compounds I.F1, wherein R is CF$_3$, and wherein the combination of R$^4_n$ and R$^1$ for each compound corresponds to one line of lines 1 to 1085 of Table A1 (Compounds I.F1-78aA1-1 to I.F1-78aA1-1085)

Table 79a Compounds I.G1, wherein R is CF$_3$, and wherein the combination of R$^4_n$ and R$^1$ for each compound corresponds to one line of lines 1 to 1085 of Table A1 (Compounds I.G1-79aA1-1 to I.G1-79aA1-1085)

Table 80a Compounds I.H1, wherein R is CF$_3$, and wherein the combination of R$^4_n$ and R$^1$ for each compound corresponds to one line of lines 1 to 1085 of Table A1 (Compounds I.H1-80aA1-1 to I.H1-80aA1-1085)

Table 81a Compounds I.J1, wherein R is CF$_3$, and wherein the combination of R$^4_n$ and R$^1$ for each compound corresponds to one line of lines 1 to 1085 of Table A1 (Compounds I.J1-81aA1-1 to I.J1-81aA1-1085)

Table 82a Compounds I.K1, wherein R is CF$_3$, and wherein the combination of R$^4_n$ and R$^1$ for each compound corresponds to one line of lines 1 to 1085 of Table A1 (Compounds I.K1-82aA1-1 to I.K1-82aA1-1085)

Table 83a Compounds I.L1, wherein R is CF$_3$, and wherein the combination of R$^4_n$ and R$^1$ for each compound corresponds to one line of lines 1 to 1085 of Table A1 (Compounds I.L1-83aA1-1 to I.L1-83aA1-1085)

Table 84a Compounds I.M1, wherein R is $CF_3$, and wherein the combination of $R^4_n$ and $R^1$ for each compound corresponds to one line of lines 1 to 1085 of Table A1 (Compounds I.M1-84aA1-1 to I.M1-84aA1-1085)

Table 85a Compounds I.N1, wherein R is $CF_3$, and wherein the combination of $R^4_n$ and $R^1$ for each compound corresponds to one line of lines 1 to 1085 of Table A1 (Compounds I.N1-85aA1-1 to I.N1-85aA1-1085)

Table 86a Compounds I.O1, wherein R is $CF_3$, and wherein the combination of $R^4_n$ and $R^1$ for each compound corresponds to one line of lines 1 to 1085 of Table A1 (Compounds I.O1-86aA1-1 to I.O1-86aA1-1085)

Table 87a Compounds I.P1, wherein R is $CF_3$, and wherein the combination of $R^4_n$ and $R^1$ for each compound corresponds to one line of lines 1 to 1085 of Table A1 (Compounds I.P1-87aA1-1 to I.P1-87aA1-1085)

Table 88a Compounds I.A2, wherein R is $CF_3$, and wherein the combination of $R^4_n$ and $R^1$ for each compound corresponds to one line of lines 1 to 1085 of Table A1 (Compounds I.A2-88aA1-1 to I.A2-88aA1-1085)

Table 89a Compounds I.B2, wherein R is $CF_3$, and wherein the combination of $R^4_n$ and $R^1$ for each compound corresponds to one line of lines 1 to 1085 of Table A1 (Compounds I.B2-89aA1-1 to I.B2-89aA1-1085)

Table 90a Compounds I.C2, wherein R is $CF_3$, and wherein the combination of $R^4_n$ and $R^1$ for each compound corresponds to one line of lines 1 to 1085 of Table A1 (Compounds I.C2-90aA1-1 to I.C2-90aA1-1085)

Table 91a Compounds I.D2, wherein R is $CF_3$, and wherein the combination of $R^4_n$ and $R^1$ for each compound corresponds to one line of lines 1 to 1085 of Table A1 (Compounds I.D2-91aA1-1 to I.D2-91-1085)

Table 92a Compounds I.E2, wherein R is $CF_3$, and wherein the combination of $R^4_n$ and $R^1$ for each compound corresponds to one line of lines 1 to 1085 of Table A1 (Compounds I.E2-92aA1-1 to I.E2-92aA1-1085)

Table 93a Compounds I.F2, wherein R is $CF_3$, and wherein the combination of $R^4_n$ and $R^1$ for each compound corresponds to one line of lines 1 to 1085 of Table A1 (Compounds I.F2-93aA1-1 to I.F2-93aA1-1085)

Table 94a Compounds I.G2, wherein R is $CF_3$, and wherein the combination of $R^4_n$ and $R^1$ for each compound corresponds to one line of lines 1 to 1085 of Table A1 (Compounds I.G2-94aA1-1 to I.G2-94aA1-1085)

Table 95a Compounds I.H2, wherein R is $CF_3$, and wherein the combination of $R^4_n$ and $R^1$ for each compound corresponds to one line of lines 1 to 1085 of Table A1 (Compounds I.H2-95aA1-1 to I.H2-95aA1-1085)

Table 96a Compounds I.J2, wherein R is $CF_3$, and wherein the combination of $R^4_n$ and $R^1$ for each compound corresponds to one line of lines 1 to 1085 of Table A1 (Compounds I.J2-96aA1-1 to I.J2-96aA1-1085)

Table 97a Compounds I.K2, wherein R is $CF_3$, and wherein the combination of $R^4_n$ and $R^1$ for each compound corresponds to one line of lines 1 to 1085 of Table A1 (Compounds I.K2-97aA1-1 to I.K2-97aA1-1085)

Table 98a Compounds I.L2, wherein R is $CF_3$, and wherein the combination of $R^4_n$ and $R^1$ for each compound corresponds to one line of lines 1 to 1085 of Table A1 (Compounds I.L2-98aA1-1 to I.L2-98aA1-1085)

Table 99a Compounds I.M2, wherein R is $CF_3$, and wherein the combination of $R^4_n$ and $R^1$ for each compound corresponds to one line of lines 1 to 1085 of Table A1 (Compounds I.M2-99aA1-1 to I.M2-99aA1-1085)

Table 100a Compounds I.N2, wherein R is $CF_3$, and wherein the combination of $R^4_n$ and $R^1$ for each compound corresponds to one line of lines 1 to 1085 of Table A1 (Compounds I.N2-100aA1-1 to I.N2-100aA1-1085)

Table 101a Compounds I.O2, wherein R is $CF_3$, and wherein the combination of $R^4_n$ and $R^1$ for each compound corresponds to one line of lines 1 to 1085 of Table A1 (Compounds I.O2-101aA1-1 to I.O2-101aA1-1085)

Table 102a Compounds I.P2, wherein R is $CF_3$, and wherein the combination of $R^4_n$ and $R^1$ for each compound corresponds to one line of lines 1 to 1085 of Table A1 (Compounds I.O2-102aA1-1 to I.O2-102aA1-1085)

Table 103a Compounds I.A3, wherein R is $CF_3$, and wherein the combination of $R^4_n$ and $R^1$ for each compound corresponds to one line of lines 1 to 1085 of Table A1 (Compounds I.A3-103aA1-1 to I.A3-103aA1-1085)

Table 104a Compounds I.B3, wherein R is $CF_3$, and wherein the combination of $R^4_n$ and $R^1$ for each compound corresponds to one line of lines 1 to 1085 of Table A1 (Compounds I.B3-104aA1-1 to I.B3-104aA1-1085)

Table 105a Compounds I.C3, wherein R is $CF_3$, and wherein the combination of $R^4_n$ and $R^1$ for each compound corresponds to one line of lines 1 to 1085 of Table A1 (Compounds I.C3-105aA1-1 to I.C3-105aA1-1085)

Table 106a Compounds I.D3, wherein R is $CF_3$, and wherein the combination of $R^4_n$ and $R^1$ for each compound corresponds to one line of lines 1 to 1085 of Table A1 (Compounds I.D3-106aA1-1 to I.D3-106aA1-1085)

Table 107a Compounds I.E3, wherein R is $CF_3$, and wherein the combination of $R^4_n$ and $R^1$ for each compound corresponds to one line of lines 1 to 1085 of Table A1 (Compounds I.E3-107aA1-1 to I.E3-107aA1-1085)

Table 108a Compounds I.F3, wherein R is $CF_3$, and wherein the combination of $R^4_n$ and $R^1$ for each compound corresponds to one line of lines 1 to 1085 of Table A1 (Compounds I.F3-108aA1-1 to I.F3-108aA1-1085)

Table 109a Compounds I.G3, wherein R is $CF_3$, and wherein the combination of $R^4_n$ and $R^1$ for each compound corresponds to one line of lines 1 to 1085 of Table A1 (Compounds I.G3-109aA1-1 to I.G3-109aA1-1085)

Table 110a Compounds I.H3, wherein R is $CF_3$, and wherein the combination of $R^4_n$ and $R^1$ for each compound corresponds to one line of lines 1 to 1085 of Table A1 (Compounds I.H3-110aA1-1 to I.H3-110aA1-1085)

Table 111a Compounds I.J3, wherein R is CF$_3$, and wherein the combination of R$^4_n$ and R$^1$ for each compound corresponds to one line of lines 1 to 1085 of Table A1 (Compounds I.J3-111aA1-1 to I.J3-111aA1-1085)

Table 112a Compounds I.K3, wherein R is CF$_3$, and wherein the combination of R$^4_n$ and R$^1$ for each compound corresponds to one line of lines 1 to 1085 of Table A1 (Compounds I.K3-112aA1-1 to I.K3-112aA1-1085)

Table 113a Compounds I.L3, wherein R is CF$_3$, and wherein the combination of R$^4_n$ and R$^1$ for each compound corresponds to one line of lines 1 to 1085 of Table A1 (Compounds I.L3-113aA1-1 to I.L3-113aA1-1085)

Table 114a Compounds I.M3, wherein R is CF$_3$, and wherein the combination of R$^4_n$ and R$^1$ for each compound corresponds to one line of lines 1 to 1085 of Table A1 (Compounds I.M3-114aA1-1 to I.M3-114aA1-1085)

Table 115a Compounds I.N3, wherein R is CF$_3$, and wherein the combination of R$^4_n$ and R$^1$ for each compound corresponds to one line of lines 1 to 1085 of Table A1 (Compounds I.N3-115aA1-1 to I.N3-115aA1-1085)

Table 116a Compounds I.O3, wherein R is CF$_3$, and wherein the combination of R$^4_n$ and R$^1$ for each compound corresponds to one line of lines 1 to 1085 of Table A1 (Compounds I.O3-116aA1-1 to I.O3-116aA1-1085)

Table 117a Compounds I.P3, wherein R is CF$_3$, and wherein the combination of R$^4_n$ and R$^1$ for each compound corresponds to one line of lines 1 to 1085 of Table A1 (Compounds I.P3-117aA1-1 to I.P3-117aA1-1085)

Table 118a Compounds I.A4, wherein R is CF$_3$, and wherein the combination of R$^4_n$ and R$^1$ for each compound corresponds to one line of lines 1 to 1085 of Table A1 (Compounds I.A4-118aA1-1 to I.A4-118aA1-1085)

Table 119a Compounds I.B4, wherein R is CF$_3$, and wherein the combination of R$^4_n$ and R$^1$ for each compound corresponds to one line of lines 1 to 1085 of Table A1 (Compounds I.B4-119aA1-1 to I.B4-119aA1-1085)

Table 120a Compounds I.C4, wherein R is CF$_3$, and wherein the combination of R$^4_n$ and R$^1$ for each compound corresponds to one line of lines 1 to 1085 of Table A1 (Compounds I.C4-120aA1-1 to I.C4-120aA1-1085)

Table 121a Compounds I.D4, wherein R is CF$_3$, and wherein the combination of R$^4_n$ and R$^1$ for each compound corresponds to one line of lines 1 to 1085 of Table A1 (Compounds I.D4-121aA1-1 to I.D4-121aA1-1085)

Table 122a Compounds I.E4, wherein R is CF$_3$, and wherein the combination of R$^4_n$ and R$^1$ for each compound corresponds to one line of lines 1 to 1085 of Table A1 (Compounds I.E4-122aA1-1 to I.E4-122aA1-1085)

Table 123a Compounds I.F4, wherein R is CF$_3$, and wherein the combination of R$^4_n$ and R$^1$ for each compound corresponds to one line of lines 1 to 1085 of Table A1 (Compounds I.F4-123aA1-1 to I.F4-123aA1-1085)

Table 124a Compounds I.G4, wherein R is CF$_3$, and wherein the combination of R$^4_n$ and R$^1$ for each compound corresponds to one line of lines 1 to 1085 of Table A1 (Compounds I.G4-124aA1-1 to I.G4-124aA1-1085)

Table 125a Compounds I.H4, wherein R is CF$_3$, and wherein the combination of R$^4_n$ and R$^1$ for each compound corresponds to one line of lines 1 to 1085 of Table A1 (Compounds I.H4-125aA1-1 to I.H4-125aA1-1085)

Table 126a Compounds I.J4, wherein R is CF$_3$, and wherein the combination of R$^4_n$ and R$^1$ for each compound corresponds to one line of lines 1 to 1085 of Table A1 (Compounds I.J4-126aA1-1 to I.J4-126aA1-1085)

Table 127a Compounds I.K4, wherein R is CF$_3$, and wherein the combination of R$^4_n$ and R$^1$ for each compound corresponds to one line of lines 1 to 1085 of Table A1 (Compounds I.K4-127aA1-1 to I.K4-127aA1-1085)

Table 128a Compounds I.L4, wherein R is CF$_3$, and wherein the combination of R$^4_n$ and R$^1$ for each compound corresponds to one line of lines 1 to 1085 of Table A1 (Compounds I.L4-128aA1-1 to I.L4-128aA1-1085)

Table 129a Compounds I.M4, wherein R is CF$_3$, and wherein the combination of R$^4_n$ and R$^1$ for each compound corresponds to one line of lines 1 to 1085 of Table A1 (Compounds I.M4-129aA1-1 to I.M4-129aA1-1085)

Table 130a Compounds I.N4, wherein R is CF$_3$, and wherein the combination of R$^4_n$ and R$^1$ for each compound corresponds to one line of lines 1 to 1085 of Table A1 (Compounds I.N4-130aA1-1 to I.N4-130aA1-1085)

Table 131a Compounds I.O4, wherein R is CF$_3$, and wherein the combination of R$^4_n$ and R$^1$ for each compound corresponds to one line of lines 1 to 1085 of Table A1 (Compounds I.O4-131aA1-1 to I.O4-131aA1-1085)

Table 132a Compounds I.P4, wherein R is CF$_3$, and wherein the combination of R$^4_n$ and R$^1$ for each compound corresponds to one line of lines 1 to 1085 of Table A1 (Compounds I.P4-132aA1-1 to I.P4-132aA1-1085)

Table 133a Compounds I.A5, wherein R is CF$_3$, and wherein the combination of R$^4_n$ and R$^1$ for each compound corresponds to one line of lines 1 to 1085 of Table A1 (Compounds I.A5-133aA1-1 to I.A5-133aA1-1085)

Table 134a Compounds I.B5, wherein R is CF$_3$, and wherein the combination of R$^4_n$ and R$^1$ for each compound corresponds to one line of lines 1 to 1085 of Table A1 (Compounds I.B5-134aA1-1 to I.B5-134aA1-1085)

Table 135a Compounds I.C5, wherein R is CF$_3$, and wherein the combination of R$^4_n$ and R$^1$ for each compound corresponds to one line of lines 1 to 1085 of Table A1 (Compounds I.C5-135aA1-1 to I.C5-135aA1-1085)

Table 136a Compounds I.D5, wherein R is CF$_3$, and wherein the combination of R$^4_n$ and R$^1$ for each compound corresponds to one line of lines 1 to 1085 of Table A1 (Compounds I.D5-136aA1-1 to I.D5-136aA1-1085)

Table 137a Compounds I.E5, wherein R is $CF_3$, and wherein the combination of $R^4_n$ and $R^1$ for each compound corresponds to one line of lines 1 to 1085 of Table A1 (Compounds I.E5-137aA1-1 to I.E5-137aA1-1085)

Table 138a Compounds I.F5, wherein R is $CF_3$, and wherein the combination of $R^4_n$ and $R^1$ for each compound corresponds to one line of lines 1 to 1085 of Table A1 (Compounds I.F5-138aA1-1 to I.F5-138aA1-1085)

Table 139a Compounds I.G5, wherein R is $CF_3$, and wherein the combination of $R^4_n$ and $R^1$ for each compound corresponds to one line of lines 1 to 1085 of Table A1 (Compounds I.G5-139aA1-1 to I.G5-139aA1-1085)

Table 140a Compounds I.H5, wherein R is $CF_3$, and wherein the combination of $R^4_n$ and $R^1$ for each compound corresponds to one line of lines 1 to 1085 of Table A1 (Compounds I.H5-140aA1-1 to I.H5-140aA1-1085)

Table 141a Compounds I.J5, wherein R is $CF_3$, and wherein the combination of $R^4_n$ and $R^1$ for each compound corresponds to one line of lines 1 to 1085 of Table A1 (Compounds I.J5-141aA1-1 to I.J5-141aA1-1085)

Table 142a Compounds I.K5, wherein R is $CF_3$, and wherein the combination of $R^4_n$ and $R^1$ for each compound corresponds to one line of lines 1 to 1085 of Table A1 (Compounds I.K5-142aA1-1 to I.K5-142aA1-1085)

Table 143a Compounds I.L5, wherein R is $CF_3$, and wherein the combination of $R^4_n$ and $R^1$ for each compound corresponds to one line of lines 1 to 1085 of Table A1 (Compounds I.L5-143aA1-1 to I.L5-143aA1-1085)

Table 144a Compounds I.M5, wherein R is $CF_3$, and wherein the combination of $R^4_n$ and $R^1$ for each compound corresponds to one line of lines 1 to 1085 of Table A1 (Compounds I.M5-144aA1-1 to I.M5-144aA1-1085)

Table 145a Compounds I.N5, wherein R is $CF_3$, and wherein the combination of $R^4_n$ and $R^1$ for each compound corresponds to one line of lines 1 to 1085 of Table A1 (Compounds I.N5-145aA1-1 to I.N5-145aA1-1085)

Table 146a Compounds I.O5, wherein R is $CF_3$, and wherein the combination of $R^4_n$ and $R^1$ for each compound corresponds to one line of lines 1 to 1085 of Table A1 (Compounds I.O5-146aA1-1 to I.O5-146aA1-1085)

Table 147a Compounds I.P5, wherein R is $CF_3$, and wherein the combination of $R^4_n$ and $R^1$ for each compound corresponds to one line of lines 1 to 1085 of Table A1 (Compounds I.P5-147aA1-1 to I.P5-147aA1-1085)

Table 148a Compounds I.A6, wherein R is $CF_3$, and wherein the combination of $R^4_n$ and $R^1$ for each compound corresponds to one line of lines 1 to 1085 of Table A1 (Compounds I.A6-148aA1-1 to I.A6-148aA1-1085)

Table 149a Compounds I.B6, wherein R is $CF_3$, and wherein the combination of $R^4_n$ and $R^1$ for each compound corresponds to one line of lines 1 to 1085 of Table A1 (Compounds I.B6-149aA1-1 to I.B6-149aA1-1085)

Table 150a Compounds I.C6, wherein R is $CF_3$, and wherein the combination of $R^4_n$ and $R^1$ for each compound corresponds to one line of lines 1 to 1085 of Table A1 (Compounds I.C6-150aA1-1 to I.C6-150aA1-1085)

Table 151a Compounds I.D6, wherein R is $CF_3$, and wherein the combination of $R^4_n$ and $R^1$ for each compound corresponds to one line of lines 1 to 1085 of Table A1 (Compounds I.D6-151aA1-1 to I.D6-151aA1-1085)

Table 152a Compounds I.E6, wherein R is $CF_3$, and wherein the combination of $R^4_n$ and $R^1$ for each compound corresponds to one line of lines 1 to 1085 of Table A1 (Compounds I.E6-152aA1-1 to I.E6-152aA1-1085)

Table 153a Compounds I.F6, wherein R is $CF_3$, and wherein the combination of $R^4_n$ and $R^1$ for each compound corresponds to one line of lines 1 to 1085 of Table A1 (Compounds I.F6-153aA1-1 to I.F6-153aA1-1085)

Table 154a Compounds I.G6, wherein R is $CF_3$, and wherein the combination of $R^4_n$ and $R^1$ for each compound corresponds to one line of lines 1 to 1085 of Table A1 (Compounds I.G6-154aA1-1 to I.G6-154aA1-1085)

Table 155a Compounds I.H6, wherein R is $CF_3$, and wherein the combination of $R^4_n$ and $R^1$ for each compound corresponds to one line of lines 1 to 1085 of Table A1 (Compounds I.H6-155aA1-1 to I.H6-155aA1-1085)

Table 156a Compounds I.J6, wherein R is $CF_3$, and wherein the combination of $R^4_n$ and $R^1$ for each compound corresponds to one line of lines 1 to 1085 of Table A1 (Compounds I.J6-156aA1-1 to I.J6-156aA1-1085)

Table 157a Compounds I.K6, wherein R is $CF_3$, and wherein the combination of $R^4_n$ and $R^1$ for each compound corresponds to one line of lines 1 to 1085 of Table A1 (Compounds I.K6-157aA1-1 to I.K6-157aA1-1085)

Table 158a Compounds I.L6, wherein R is $CF_3$, and wherein the combination of $R^4_n$ and $R^1$ for each compound corresponds to one line of lines 1 to 1085 of Table A1 (Compounds I.L6-158aA1-1 to I.L6-158aA1-1085)

Table 159a Compounds I.M6, wherein R is $CF_3$, and wherein the combination of $R^4_n$ and $R^1$ for each compound corresponds to one line of lines 1 to 1085 of Table A1 (Compounds I.M6-159aA1-1 to I.M6-159aA1-1085)

Table 160a Compounds I.N6, wherein R is $CF_3$, and wherein the combination of $R^4_n$ and $R^1$ for each compound corresponds to one line of lines 1 to 1085 of Table A1 (Compounds I.N6-160aA1-1 to I.N6-160aA1-1085)

Table 161a Compounds I.O6, wherein R is $CF_3$, and wherein the combination of $R^4_n$ and $R^1$ for each compound corresponds to one line of lines 1 to 1085 of Table A1 (Compounds I.O6-161aA1-1 to I.O6-161aA1-1085)

Table 162a Compounds I.P6, wherein R is $CF_3$, and wherein the combination of $R^4_n$ and $R^1$ for each compound corresponds to one line of lines 1 to 1085 of Table A1 (Compounds I.P6-162aA1-1 to I.P6-162aA1-1085)

Table 163a Compounds I.A7, wherein R is CF$_3$, and wherein the combination of R$^4{}_n$ and R$^1$ for each compound corresponds to one line of lines 1 to 1085 of Table A1 (Compounds I.A7-163aA1-1 to I.A7-163aA1-1085)

Table 164a Compounds I.B7, wherein R is CF$_3$, and wherein the combination of R$^4{}_n$ and R$^1$ for each compound corresponds to one line of lines 1 to 1085 of Table A1 (Compounds I.B7-164aA1-1 to I.B7-164aA1-1085)

Table 165a Compounds I.C7, wherein R is CF$_3$, and wherein the combination of R$^4{}_n$ and R$^1$ for each compound corresponds to one line of lines 1 to 1085 of Table A1 (Compounds I.C7-165aA1-1 to I.C7-165aA1-1085)

Table 166a Compounds I.D7, wherein R is CF$_3$, and wherein the combination of R$^4{}_n$ and R$^1$ for each compound corresponds to one line of lines 1 to 1085 of Table A1 (Compounds I.D7-166aA1-1 to I.D7-166aA1-1085)

Table 167a Compounds I.E7, wherein R is CF$_3$, and wherein the combination of R$^4{}_n$ and R$^1$ for each compound corresponds to one line of lines 1 to 1085 of Table A1 (Compounds I.E7-167aA1-1 to I.E7-167aA1-1085)

Table 168a Compounds I.F7, wherein R is CF$_3$, and wherein the combination of R$^4{}_n$ and R$^1$ for each compound corresponds to one line of lines 1 to 1085 of Table A1 (Compounds I.F7-168aA1-1 to I.F7-168aA1-1085)

Table 169a Compounds I.G7, wherein R is CF$_3$, and wherein the combination of R$^4{}_n$ and R$^1$ for each compound corresponds to one line of lines 1 to 1085 of Table A1 (Compounds I.G7-169aA1-1 to I.G7-169aA1-1085)

Table 170a Compounds I.H7, wherein R is CF$_3$, and wherein the combination of R$^4{}_n$ and R$^1$ for each compound corresponds to one line of lines 1 to 1085 of Table A1 (Compounds I.H7-170aA1-1 to I.H7-170aA1-1085)

Table 171a Compounds I.J7, wherein R is CF$_3$, and wherein the combination of R$^4{}_n$ and R$^1$ for each compound corresponds to one line of lines 1 to 1085 of Table A1 (Compounds I.J7-171aA1-1 to I.J7-171aA1-1085)

Table 172a Compounds I.K7, wherein R is CF$_3$, and wherein the combination of R$^4{}_n$ and R$^1$ for each compound corresponds to one line of lines 1 to 1085 of Table A1 (Compounds I.K7-172aA1-1 to I.K7-172aA1-1085)

Table 173a Compounds I.L7, wherein R is CF$_3$, and wherein the combination of R$^4{}_n$ and R$^1$ for each compound corresponds to one line of lines 1 to 1085 of Table A1 (Compounds I.L7-173aA1-1 to I.L7-173aA1-1085)

Table 174a Compounds I.M7, wherein R is CF$_3$, and wherein the combination of R$^4{}_n$ and R$^1$ for each compound corresponds to one line of lines 1 to 1085 of Table A1 (Compounds I.M7-174aA1-1 to I.M7-174aA1-1085)

Table 175a Compounds I.N7, wherein R is CF$_3$, and wherein the combination of R$^4{}_n$ and R$^1$ for each compound corresponds to one line of lines 1 to 1085 of Table A1 (Compounds I.N7-175aA1-1 to I.N7-175aA1-1085)

Table 176a Compounds I.O7, wherein R is CF$_3$, and wherein the combination of R$^4{}_n$ and R$^1$ for each compound corresponds to one line of lines 1 to 1085 of Table A1 (Compounds I.O7-176aA1-1 to I.O7-176aA1-1085)

Table 177a Compounds I.P7, wherein R is CF$_3$, and wherein the combination of R$^4{}_n$ and R$^1$ for each compound corresponds to one line of lines 1 to 1085 of Table A1 (Compounds I.P7-177aA1-1 to I.P7-177aA1-1085)

Table 178a Compounds I.A8, wherein R is CF$_3$, and wherein the combination of R$^4{}_n$ and R$^1$ for each compound corresponds to one line of lines 1 to 1085 of Table A1 (Compounds I.A8-178aA1-1 to I.A8-178aA1-1085)

Table 179a Compounds I.B8, wherein R is CF$_3$, and wherein the combination of R$^4{}_n$ and R$^1$ for each compound corresponds to one line of lines 1 to 1085 of Table A1 (Compounds I.B8-179aA1-1 to I.B8-179aA1-1085)

Table 180a Compounds I.C8, wherein R is CF$_3$, and wherein the combination of R$^4{}_n$ and R$^1$ for each compound corresponds to one line of lines 1 to 1085 of Table A1 (Compounds I.C8-180aA1-1 to I.C8-180aA1-1085)

Table 181a Compounds I.D8, wherein R is CF$_3$, and wherein the combination of R$^4{}_n$ and R$^1$ for each compound corresponds to one line of lines 1 to 1085 of Table A1 (Compounds I.D8-181aA1-1 to I.D8-181aA1-1085)

Table 182a Compounds I.E8, wherein R is CF$_3$, and wherein the combination of R$^4{}_n$ and R$^1$ for each compound corresponds to one line of lines 1 to 1085 of Table A1 (Compounds I.E8-182aA1-1 to I.E8-182aA1-1085)

Table 183a Compounds I.F8, wherein R is CF$_3$, and wherein the combination of R$^4{}_n$ and R$^1$ for each compound corresponds to one line of lines 1 to 1085 of Table A1 (Compounds I.F8-183aA1-1 to I.F8-183aA1-1085)

Table 184a Compounds I.G8, wherein R is CF$_3$, and wherein the combination of R$^4{}_n$ and R$^1$ for each compound corresponds to one line of lines 1 to 1085 of Table A1 (Compounds I.G8-184aA1-1 to I.G8-184aA1-1085)

Table 185a Compounds I.H8, wherein R is CF$_3$, and wherein the combination of R$^4{}_n$ and R$^1$ for each compound corresponds to one line of lines 1 to 1085 of Table A1 (Compounds I.H8-185aA1-1 to I.H8-185aA1-1085)

Table 186a Compounds I.J8, wherein R is CF$_3$, and wherein the combination of R$^4{}_n$ and R$^1$ for each compound corresponds to one line of lines 1 to 1085 of Table A1 (Compounds I.J8-186aA1-1 to I.J8-186aA1-1085)

Table 187a Compounds I.K8, wherein R is CF$_3$, and wherein the combination of R$^4{}_n$ and R$^1$ for each compound corresponds to one line of lines 1 to 1085 of Table A1 (Compounds I.K8-187aA1-1 to I.K8-187aA1-1085)

Table 188a Compounds I.L8, wherein R is CF$_3$, and wherein the combination of R$^4{}_n$ and R$^1$ for each compound corresponds to one line of lines 1 to 1085 of Table A1 (Compounds I.L8-188aA1-1 to I.L8-188aA1-1085)

Table 189a Compounds I.M8, wherein R is $CF_3$, and wherein the combination of $R^4_n$ and $R^1$ for each compound corresponds to one line of lines 1 to 1085 of Table A1 (Compounds I.M8-189aA1-1 to I.M8-189aA1-1085)

Table 190a Compounds I.N8, wherein R is $CF_3$, and wherein the combination of $R^4_n$ and $R^1$ for each compound corresponds to one line of lines 1 to 1085 of Table A1 (Compounds I.N8-190aA1-1 to I.N8-190aA1-1085)

Table 191a Compounds I.O8, wherein R is $CF_3$, and wherein the combination of $R^4_n$ and $R^1$ for each compound corresponds to one line of lines 1 to 1085 of Table A1 (Compounds I.O8-191aA1-1 to I.O8-191aA1-1085)

Table 192a Compounds I.P8, wherein R is $CF_3$, and wherein the combination of $R^4_n$ and $R^1$ for each compound corresponds to one line of lines 1 to 1085 of Table A1 (Compounds I.P8-192aA1-1 to I.P8-192aA1-1085)

Table 193a Compounds I.A9, wherein R is $CF_3$, and wherein the combination of $R^4_n$ and $R^1$ for each compound corresponds to one line of lines 1 to 1085 of Table A1 (Compounds I.A9-193aA1-1 to I.A9-193aA1-1085)

Table 194a Compounds I.B9, wherein R is $CF_3$, and wherein the combination of $R^4_n$ and $R^1$ for each compound corresponds to one line of lines 1 to 1085 of Table A1 (Compounds I.B9-194aA1-1 to I.B9-194aA1-1085)

Table 195a Compounds I.C9, wherein R is $CF_3$, and wherein the combination of $R^4_n$ and $R^1$ for each compound corresponds to one line of lines 1 to 1085 of Table A1 (Compounds I.C9-195aA1-1 to I.C9-195aA1-1085)

Table 196a Compounds I.D9, wherein R is $CF_3$, and wherein the combination of $R^4_n$ and $R^1$ for each compound corresponds to one line of lines 1 to 1085 of Table A1 (Compounds I.D9-196aA1-1 to I.D9-196aA1-1085)

Table 197a Compounds I.E9, wherein R is $CF_3$, and wherein the combination of $R^4_n$ and $R^1$ for each compound corresponds to one line of lines 1 to 1085 of Table A1 (Compounds I.E9-197aA1-1 to I.E9-197aA1-1085)

Table 198a Compounds I.F9, wherein R is $CF_3$, and wherein the combination of $R^4_n$ and $R^1$ for each compound corresponds to one line of lines 1 to 1085 of Table A1 (Compounds I.F9-198aA1-1 to I.F9-198aA1-1085)

Table 199a Compounds I.G9, wherein R is $CF_3$, and wherein the combination of $R^4_n$ and $R^1$ for each compound corresponds to one line of lines 1 to 1085 of Table A1 (Compounds I.G9-199aA1-1 to I.G9-199aA1-1085)

Table 200a Compounds I.H9, wherein R is $CF_3$, and wherein the combination of $R^4_n$ and $R^1$ for each compound corresponds to one line of lines 1 to 1085 of Table A1 (Compounds I.H9-200aA1-1 to I.H9-200aA1-1085)

Table 201a Compounds I.J9, wherein R is $CF_3$, and wherein the combination of $R^4_n$ and $R^1$ for each compound corresponds to one line of lines 1 to 1085 of Table A1 (Compounds I.J9-201aA1-1 to I.J9-201aA1-1085)

Table 202a Compounds I.K9, wherein R is $CF_3$, and wherein the combination of $R^4_n$ and $R^1$ for each compound corresponds to one line of lines 1 to 1085 of Table A1 (Compounds I.K9-202aA1-1 to I.K9-202aA1-1085)

Table 203a Compounds I.L9, wherein R is $CF_3$, and wherein the combination of $R^4_n$ and $R^1$ for each compound corresponds to one line of lines 1 to 1085 of Table A1 (Compounds I.L9-203aA1-1 to I.L9-203aA1-1085)

Table 204a Compounds I.M9, wherein R is $CF_3$, and wherein the combination of $R^4_n$ and $R^1$ for each compound corresponds to one line of lines 1 to 1085 of Table A1 (Compounds I.M9-204aA1-1 to I.M9-204aA1-1085)

Table 205a Compounds I.N9, wherein R is $CF_3$, and wherein the combination of $R^4_n$ and $R^1$ for each compound corresponds to one line of lines 1 to 1085 of Table A1 (Compounds I.N9-205aA1-1 to I.N9-205aA1-1085)

Table 206a Compounds I.O9, wherein R is $CF_3$, and wherein the combination of $R^4_n$ and $R^1$ for each compound corresponds to one line of lines 1 to 1085 of Table A1 (Compounds I.O9-206aA1-1 to I.O9-206aA1-1085)

Table 207a Compounds I.P9, wherein R is $CF_3$, and wherein the combination of $R^4_n$ and $R^1$ for each compound corresponds to one line of lines 1 to 1085 of Table A1 (Compounds I.P9-207aA1-1 to I.P9-207aA1-1085)

Table 208a Compounds I.A10, wherein R is $CF_3$, and wherein the combination of $R^4_n$ and $R^1$ for each compound corresponds to one line of lines 1 to 1085 of Table A1 (Compounds I.A10-208aA1-1 to I.A10-208aA1-1085)

Table 209a Compounds I.B10, wherein R is $CF_3$, and wherein the combination of $R^4_n$ and $R^1$ for each compound corresponds to one line of lines 1 to 1085 of Table A1 (Compounds I.B10-209aA1-1 to I.B10-209aA1-1085)

Table 210a Compounds I.C10, wherein R is $CF_3$, and wherein the combination of $R^4_n$ and $R^1$ for each compound corresponds to one line of lines 1 to 1085 of Table A1 (Compounds I.B10-210aA1-1 to I.C10-210aA1-1085)

Table 211a Compounds I.D10, wherein R is $CF_3$, and wherein the combination of $R^4_n$ and $R^1$ for each compound corresponds to one line of lines 1 to 1085 of Table A1 (Compounds I.D10-211aA1-1 to I.D10-211aA1-1085)

Table 212a Compounds I.E10, wherein R is $CF_3$, and wherein the combination of $R^4_n$ and $R^1$ for each compound corresponds to one line of lines 1 to 1085 of Table A1 (Compounds I.E10-212aA1-1 to I.E10-212aA1-1085)

Table 213a Compounds I.F10, wherein R is $CF_3$, and wherein the combination of $R^4_n$ and $R^1$ for each compound corresponds to one line of lines 1 to 1085 of Table A1 (Compounds I.F10-213aA1-1 to I.F10-213aA1-1085)

Table 214a Compounds I.G10, wherein R is $CF_3$, and wherein the combination of $R^4_n$ and $R^1$ for each compound corresponds to one line of lines 1 to 1085 of Table A1 (Compounds I.G10-214aA1-1 to I.G10-214aA1-1085)

Table 215a Compounds I.H10, wherein R is $CF_3$, and wherein the combination of $R^4_n$ and $R^1$ for each compound corresponds to one line of lines 1 to 1085 of Table A1 (Compounds I.H10-215aA1-1 to I.H10-215aA1-1085)

Table 216a Compounds I.J10, wherein R is $CF_3$, and wherein the combination of $R^4_n$ and $R^1$ for each compound corresponds to one line of lines 1 to 1085 of Table A1 (Compounds I.J10-216aA1-1 to I.J10-216aA1-1085)

Table 217a Compounds I.K10, wherein R is $CF_3$, and wherein the combination of $R^4_n$ and $R^1$ for each compound corresponds to one line of lines 1 to 1085 of Table A1 (Compounds I.K10-217aA1-1 to I.K10-217aA1-1085)

Table 218a Compounds I.L10, wherein R is $CF_3$, and wherein the combination of $R^4_n$ and $R^1$ for each compound corresponds to one line of lines 1 to 1085 of Table A1 (Compounds I.L10-218aA1-1 to I.L10-218aA1-1085)

Table 219a Compounds I.M10, wherein R is $CF_3$, and wherein the combination of $R^4_n$ and $R^1$ for each compound corresponds to one line of lines 1 to 1085 of Table A1 (Compounds I.M10-219aA1-1 to I.M10-219aA1-1085)

Table 220a Compounds I.N10, wherein R is $CF_3$, and wherein the combination of $R^4_n$ and $R^1$ for each compound corresponds to one line of lines 1 to 1085 of Table A1 (Compounds I.N10-220aA1-1 to I.N10-220aA1-1085)

Table 221a Compounds I.O10, wherein R is $CF_3$, and wherein the combination of $R^4_n$ and $R^1$ for each compound corresponds to one line of lines 1 to 1085 of Table A1 (Compounds I.O10-221aA1-1 to I.O10-221aA1-1085)

Table 222a Compounds I.P10, wherein R is $CF_3$, and wherein the combination of $R^4_n$ and $R^1$ for each compound corresponds to one line of lines 1 to 1085 of Table A1 (Compounds I.P10-222aA1-1 to I.P10-222aA1-1085)

Table 223a Compounds I.A11, wherein R is $CF_3$, and wherein the combination of $R^4_n$ and $R^1$ for each compound corresponds to one line of lines 1 to 1085 of Table A1 (Compounds I.A11-223aA1-1 to I.A11-223aA1-1085)

Table 224a Compounds I.B11, wherein R is $CF_3$, and wherein the combination of $R^4_n$ and $R^1$ for each compound corresponds to one line of lines 1 to 1085 of Table A1 (Compounds I.B11-224aA1-1 to I.B11-224aA1-1085)

Table 225a Compounds I.C11, wherein R is $CF_3$, and wherein the combination of $R^4_n$ and $R^1$ for each compound corresponds to one line of lines 1 to 1085 of Table A1 (Compounds I.C11-225aA1-1 to I.C11-225aA1-1085)

Table 226a Compounds I.D11, wherein R is $CF_3$, and wherein the combination of $R^4_n$ and $R^1$ for each compound corresponds to one line of lines 1 to 1085 of Table A1 (Compounds I.D11-226aA1-1 to I.D11-226aA1-1085)

Table 227a Compounds I.E11, wherein R is $CF_3$, and wherein the combination of $R^4_n$ and $R^1$ for each compound corresponds to one line of lines 1 to 1085 of Table A1 (Compounds I.E11-227aA1-1 to I.E11-227aA1-1085)

Table 228a Compounds I.F11, wherein R is $CF_3$, and wherein the combination of $R^4_n$ and $R^1$ for each compound corresponds to one line of lines 1 to 1085 of Table A1 (Compounds I.F11-228aA1-1 to I.F11-228aA1-1085)

Table 229a Compounds I.G11, wherein R is $CF_3$, and wherein the combination of $R^4_n$ and $R^1$ for each compound corresponds to one line of lines 1 to 1085 of Table A1 (Compounds I.G11-229aA1-1 to I.G11-229aA1-1085)

Table 230a Compounds I.H11, wherein R is $CF_3$, and wherein the combination of $R^4_n$ and $R^1$ for each compound corresponds to one line of lines 1 to 1085 of Table A1 (Compounds I.H11-230aA1-1 to I.H11-230aA1-1085)

Table 231a Compounds I.J11, wherein R is $CF_3$, and wherein the combination of $R^4_n$ and $R^1$ for each compound corresponds to one line of lines 1 to 1085 of Table A1 (Compounds I.J11-231aA1-1 to I.J11-231aA1-1085)

Table 232a Compounds I.K11, wherein R is $CF_3$, and wherein the combination of $R^4_n$ and $R^1$ for each compound corresponds to one line of lines 1 to 1085 of Table A1 (Compounds I.K11-232aA1-1 to I.K11-232aA1-1085)

Table 233a Compounds I.L11, wherein R is $CF_3$, and wherein the combination of $R^4_n$ and $R^1$ for each compound corresponds to one line of lines 1 to 1085 of Table A1 (Compounds I.L11-233aA1-1 to I.L11-233aA1-1085)

Table 234a Compounds I.M11, wherein R is $CF_3$, and wherein the combination of $R^4_n$ and $R^1$ for each compound corresponds to one line of lines 1 to 1085 of Table A1 (Compounds I.M11-234aA1-1 to I.M11-234aA1-1085)

Table 235a Compounds I.N11, wherein R is $CF_3$, and wherein the combination of $R^4_n$ and $R^1$ for each compound corresponds to one line of lines 1 to 1085 of Table A1 (Compounds I.N11-235aA1-1 to I.N11-235aA1-1085)

Table 236a Compounds I.O11, wherein R is $CF_3$, and wherein the combination of $R^4_n$ and $R^1$ for each compound corresponds to one line of lines 1 to 1085 of Table A1 (Compounds I.O11-236aA1-1 to I.O11-236aA1-1085)

Table 237a Compounds I.P11, wherein R is $CF_3$, and wherein the combination of $R^4_n$ and $R^1$ for each compound corresponds to one line of lines 1 to 1085 of Table A1 (Compounds I.P11-237aA1-1 to I.P11-237aA1-1085)

TABLE A1

| No. | $R^4_m$ | $R^1$ |
|---|---|---|
| 1 | —* | H |
| 2 | 2-Cl | H |
| 3 | 3-Cl | H |
| 4 | 4-Cl | H |
| 5 | 2-F | H |
| 6 | 3-F | H |
| 7 | 4-F | H |
| 8 | 2,4-$Cl_2$ | H |
| 9 | 2,6-$Cl_2$ | H |
| 10 | 2,4-$F_2$ | H |

TABLE A1-continued

| No. | $R^4_m$ | $R^1$ |
|---|---|---|
| 11 | 2,6-F$_2$ | H |
| 12 | 2-F-3-Cl | H |
| 13 | 2-F-4-Cl | H |
| 14 | 2-Cl-3-F | H |
| 15 | 2-Cl-4-F | H |
| 16 | 2-CH$_3$ | H |
| 17 | 3-CH$_3$ | H |
| 18 | 4-CH$_3$ | H |
| 19 | 4-CF$_3$ | H |
| 20 | 2-CHF$_2$ | H |
| 21 | 3-CHF$_2$ | H |
| 22 | 4-CHF$_2$ | H |
| 23 | 2-OCH$_3$ | H |
| 24 | 4-OCH$_3$ | H |
| 25 | 2-OCF$_3$ | H |
| 26 | 4-OCF$_3$ | H |
| 27 | 2-OCHF$_2$ | H |
| 28 | 3-OCHF$_2$ | H |
| 29 | 4-OCHF$_2$ | H |
| 30 | 2,4-(CH$_3$)$_2$ | H |
| 31 | 2,4,6-(CH$_3$)$_3$ | H |
| 32 | —* | CH$_3$ |
| 33 | 2-Cl | CH$_3$ |
| 34 | 3-Cl | CH$_3$ |
| 35 | 4-Cl | CH$_3$ |
| 36 | 2-F | CH$_3$ |
| 37 | 3-F | CH$_3$ |
| 38 | 4-F | CH$_3$ |
| 39 | 2,4-Cl$_2$ | CH$_3$ |
| 40 | 2,6-Cl$_2$ | CH$_3$ |
| 41 | 2,4-F$_2$ | CH$_3$ |
| 42 | 2,6-F$_2$ | CH$_3$ |
| 43 | 2-F-3-Cl | CH$_3$ |
| 44 | 2-F-4-Cl | CH$_3$ |
| 45 | 2-Cl-3-F | CH$_3$ |
| 46 | 2-Cl-4-F | CH$_3$ |
| 47 | 2-CH$_3$ | CH$_3$ |
| 48 | 3-CH$_3$ | CH$_3$ |
| 49 | 4-CH$_3$ | CH$_3$ |
| 50 | 4-CF$_3$ | CH$_3$ |
| 51 | 2-CHF$_2$ | CH$_3$ |
| 52 | 3-CHF$_2$ | CH$_3$ |
| 53 | 4-CHF$_2$ | CH$_3$ |
| 54 | 2-OCH$_3$ | CH$_3$ |
| 55 | 4-OCH$_3$ | CH$_3$ |
| 56 | 2-OCF$_3$ | CH$_3$ |
| 57 | 4-OCF$_3$ | CH$_3$ |
| 58 | 2-OCHF$_2$ | CH$_3$ |
| 59 | 3-OCHF$_2$ | CH$_3$ |
| 60 | 4-OCHF$_2$ | CH$_3$ |
| 61 | 2,4-(CH$_3$)$_2$ | CH$_3$ |
| 62 | 2,4,6-(CH$_3$)$_3$ | CH$_3$ |
| 63 | —* | CH$_2$CH$_3$ |
| 64 | 2-Cl | CH$_2$CH$_3$ |
| 65 | 3-Cl | CH$_2$CH$_3$ |
| 66 | 4-Cl | CH$_2$CH$_3$ |
| 67 | 2-F | CH$_2$CH$_3$ |
| 68 | 3-F | CH$_2$CH$_3$ |
| 69 | 4-F | CH$_2$CH$_3$ |
| 70 | 2,4-Cl$_2$ | CH$_2$CH$_3$ |
| 71 | 2,6-Cl$_2$ | CH$_2$CH$_3$ |
| 72 | 2,4-F$_2$ | CH$_2$CH$_3$ |
| 73 | 2,6-F$_2$ | CH$_2$CH$_3$ |
| 74 | 2-F-3-Cl | CH$_2$CH$_3$ |
| 75 | 2-F-4-Cl | CH$_2$CH$_3$ |
| 76 | 2-Cl-3-F | CH$_2$CH$_3$ |
| 77 | 2-Cl-4-F | CH$_2$CH$_3$ |
| 78 | 2-CH$_3$ | CH$_2$CH$_3$ |
| 79 | 3-CH$_3$ | CH$_2$CH$_3$ |
| 80 | 4-CH$_3$ | CH$_2$CH$_3$ |
| 81 | 4-CF$_3$ | CH$_2$CH$_3$ |
| 82 | 2-CHF$_2$ | CH$_2$CH$_3$ |
| 83 | 3-CHF$_2$ | CH$_2$CH$_3$ |
| 84 | 4-CHF$_2$ | CH$_2$CH$_3$ |
| 85 | 2-OCH$_3$ | CH$_2$CH$_3$ |
| 86 | 4-OCH$_3$ | CH$_2$CH$_3$ |
| 87 | 2-OCF$_3$ | CH$_2$CH$_3$ |
| 88 | 4-OCF$_3$ | CH$_2$CH$_3$ |
| 89 | 2-OCHF$_2$ | CH$_2$CH$_3$ |
| 90 | 3-OCHF$_2$ | CH$_2$CH$_3$ |
| 91 | 4-OCHF$_2$ | CH$_2$CH$_3$ |
| 92 | 2,4-(CH$_3$)$_2$ | CH$_2$CH$_3$ |
| 93 | 2,4,6-(CH$_3$)$_3$ | CH$_2$CH$_3$ |
| 94 | —* | CH$_2$CH$_2$CH$_3$ |
| 95 | 2-Cl | CH$_2$CH$_2$CH$_3$ |
| 96 | 3-Cl | CH$_2$CH$_2$CH$_3$ |
| 97 | 4-Cl | CH$_2$CH$_2$CH$_3$ |
| 98 | 2-F | CH$_2$CH$_2$CH$_3$ |
| 99 | 3-F | CH$_2$CH$_2$CH$_3$ |
| 100 | 4-F | CH$_2$CH$_2$CH$_3$ |
| 101 | 2,4-Cl$_2$ | CH$_2$CH$_2$CH$_3$ |
| 102 | 2,6-Cl$_2$ | CH$_2$CH$_2$CH$_3$ |
| 103 | 2,4-F$_2$ | CH$_2$CH$_2$CH$_3$ |
| 104 | 2,6-F$_2$ | CH$_2$CH$_2$CH$_3$ |
| 105 | 2-F-3-Cl | CH$_2$CH$_2$CH$_3$ |
| 106 | 2-F-4-Cl | CH$_2$CH$_2$CH$_3$ |
| 107 | 2-Cl-3-F | CH$_2$CH$_2$CH$_3$ |
| 108 | 2-Cl-4-F | CH$_2$CH$_2$CH$_3$ |
| 109 | 2-CH$_3$ | CH$_2$CH$_2$CH$_3$ |
| 110 | 3-CH$_3$ | CH$_2$CH$_2$CH$_3$ |
| 111 | 4-CH$_3$ | CH$_2$CH$_2$CH$_3$ |
| 112 | 4-CF$_3$ | CH$_2$CH$_2$CH$_3$ |
| 113 | 2-CHF$_2$ | CH$_2$CH$_2$CH$_3$ |
| 114 | 3-CHF$_2$ | CH$_2$CH$_2$CH$_3$ |
| 115 | 4-CHF$_2$ | CH$_2$CH$_2$CH$_3$ |
| 116 | 2-OCH$_3$ | CH$_2$CH$_2$CH$_3$ |
| 117 | 4-OCH$_3$ | CH$_2$CH$_2$CH$_3$ |
| 118 | 2-OCF$_3$ | CH$_2$CH$_2$CH$_3$ |
| 119 | 4-OCF$_3$ | CH$_2$CH$_2$CH$_3$ |
| 120 | 2-OCHF$_2$ | CH$_2$CH$_2$CH$_3$ |
| 121 | 3-OCHF$_2$ | CH$_2$CH$_2$CH$_3$ |
| 122 | 4-OCHF$_2$ | CH$_2$CH$_2$CH$_3$ |
| 123 | 2,4-(CH$_3$)$_2$ | CH$_2$CH$_2$CH$_3$ |
| 124 | 2,4,6-(CH$_3$)$_3$ | CH$_2$CH$_2$CH$_3$ |
| 125 | —* | CH(CH$_3$)$_2$ |
| 126 | 2-Cl | CH(CH$_3$)$_2$ |
| 127 | 3-Cl | CH(CH$_3$)$_2$ |
| 128 | 4-Cl | CH(CH$_3$)$_2$ |
| 129 | 2-F | CH(CH$_3$)$_2$ |
| 130 | 3-F | CH(CH$_3$)$_2$ |
| 131 | 4-F | CH(CH$_3$)$_2$ |
| 132 | 2,4-Cl$_2$ | CH(CH$_3$)$_2$ |
| 133 | 2,6-Cl$_2$ | CH(CH$_3$)$_2$ |
| 134 | 2,4-F$_2$ | CH(CH$_3$)$_2$ |
| 135 | 2,6-F$_2$ | CH(CH$_3$)$_2$ |
| 136 | 2-F-3-Cl | CH(CH$_3$)$_2$ |
| 137 | 2-F-4-Cl | CH(CH$_3$)$_2$ |
| 138 | 2-Cl-3-F | CH(CH$_3$)$_2$ |
| 139 | 2-Cl-4-F | CH(CH$_3$)$_2$ |
| 140 | 2-CH$_3$ | CH(CH$_3$)$_2$ |
| 141 | 3-CH$_3$ | CH(CH$_3$)$_2$ |
| 142 | 4-CH$_3$ | CH(CH$_3$)$_2$ |
| 143 | 4-CF$_3$ | CH(CH$_3$)$_2$ |
| 144 | 2-CHF$_2$ | CH(CH$_3$)$_2$ |
| 145 | 3-CHF$_2$ | CH(CH$_3$)$_2$ |
| 146 | 4-CHF$_2$ | CH(CH$_3$)$_2$ |
| 147 | 2-OCH$_3$ | CH(CH$_3$)$_2$ |
| 148 | 4-OCH$_3$ | CH(CH$_3$)$_2$ |
| 149 | 2-OCF$_3$ | CH(CH$_3$)$_2$ |
| 150 | 4-OCF$_3$ | CH(CH$_3$)$_2$ |
| 151 | 2-OCHF$_2$ | CH(CH$_3$)$_2$ |
| 152 | 3-OCHF$_2$ | CH(CH$_3$)$_2$ |
| 153 | 4-OCHF$_2$ | CH(CH$_3$)$_2$ |
| 154 | 2,4-(CH$_3$)$_2$ | CH(CH$_3$)$_2$ |
| 155 | 2,4,6-(CH$_3$)$_3$ | CH(CH$_3$)$_2$ |
| 156 | —* | C$_3$H$_5$ (c-propyl) |
| 157 | 2-Cl | C$_3$H$_5$ (c-propyl) |
| 158 | 3-Cl | C$_3$H$_5$ (c-propyl) |
| 159 | 4-Cl | C$_3$H$_5$ (c-propyl) |
| 160 | 2-F | C$_3$H$_5$ (c-propyl) |
| 161 | 3-F | C$_3$H$_5$ (c-propyl) |
| 162 | 4-F | C$_3$H$_5$ (c-propyl) |
| 163 | 2,4-Cl$_2$ | C$_3$H$_5$ (c-propyl) |
| 164 | 2,6-Cl$_2$ | C$_3$H$_5$ (c-propyl) |
| 165 | 2,4-F$_2$ | C$_3$H$_5$ (c-propyl) |
| 166 | 2,6-F$_2$ | C$_3$H$_5$ (c-propyl) |

TABLE A1-continued

| No. | $R^4_m$ | $R^1$ |
|---|---|---|
| 167 | 2-F-3-Cl | C₃H₅ (c-propyl) |
| 168 | 2-F-4-Cl | C₃H₅ (c-propyl) |
| 169 | 2-Cl-3-F | C₃H₅ (c-propyl) |
| 170 | 2-Cl-4-F | C₃H₅ (c-propyl) |
| 171 | 2-CH₃ | C₃H₅ (c-propyl) |
| 172 | 3-CH₃ | C₃H₅ (c-propyl) |
| 173 | 4-CH₃ | C₃H₅ (c-propyl) |
| 174 | 4-CF₃ | C₃H₅ (c-propyl) |
| 175 | 2-CHF₂ | C₃H₅ (c-propyl) |
| 176 | 3-CHF₂ | C₃H₅ (c-propyl) |
| 177 | 4-CHF₂ | C₃H₅ (c-propyl) |
| 178 | 2-OCH₃ | C₃H₅ (c-propyl) |
| 179 | 4-OCH₃ | C₃H₅ (c-propyl) |
| 180 | 2-OCF₃ | C₃H₅ (c-propyl) |
| 181 | 4-OCF₃ | C₃H₅ (c-propyl) |
| 182 | 2-OCHF₂ | C₃H₅ (c-propyl) |
| 183 | 3-OCHF₂ | C₃H₅ (c-propyl) |
| 184 | 4-OCHF₂ | C₃H₅ (c-propyl) |
| 185 | 2,4-(CH₃)₂ | C₃H₅ (c-propyl) |
| 186 | 2,4,6-(CH₃)₃ | C₃H₅ (c-propyl) |
| 187 | —* | C₆H₅ |
| 188 | 2-Cl | C₆H₅ |
| 189 | 3-Cl | C₆H₅ |
| 190 | 4-Cl | C₆H₅ |
| 191 | 2-F | C₆H₅ |
| 192 | 3-F | C₆H₅ |
| 193 | 4-F | C₆H₅ |
| 194 | 2,4-Cl₂ | C₆H₅ |
| 195 | 2,6-Cl₂ | C₆H₅ |
| 196 | 2,4-F₂ | C₆H₅ |
| 197 | 2,6-F₂ | C₆H₅ |
| 198 | 2-F-3-Cl | C₆H₅ |
| 199 | 2-F-4-Cl | C₆H₅ |
| 200 | 2-Cl-3-F | C₆H₅ |
| 201 | 2-Cl-4-F | C₆H₅ |
| 202 | 2-CH₃ | C₆H₅ |
| 203 | 3-CH₃ | C₆H₅ |
| 204 | 4-CH₃ | C₆H₅ |
| 205 | 4-CF₃ | C₆H₅ |
| 206 | 2-CHF₂ | C₆H₅ |
| 207 | 3-CHF₂ | C₆H₅ |
| 208 | 4-CHF₂ | C₆H₅ |
| 209 | 2-OCH₃ | C₆H₅ |
| 210 | 4-OCH₃ | C₆H₅ |
| 211 | 2-OCF₃ | C₆H₅ |
| 212 | 4-OCF₃ | C₆H₅ |
| 213 | 2-OCHF₂ | C₆H₅ |
| 214 | 3-OCHF₂ | C₆H₅ |
| 215 | 4-OCHF₂ | C₆H₅ |
| 216 | 2,4-(CH₃)₂ | C₆H₅ |
| 217 | 2,4,6-(CH₃)₃ | C₆H₅ |
| 218 | —* | CH₂C₆H₅ |
| 219 | 2-Cl | CH₂C₆H₅ |
| 220 | 3-Cl | CH₂C₆H₅ |
| 221 | 4-Cl | CH₂C₆H₅ |
| 222 | 2-F | CH₂C₆H₅ |
| 223 | 3-F | CH₂C₆H₅ |
| 224 | 4-F | CH₂C₆H₅ |
| 225 | 2,4-Cl₂ | CH₂C₆H₅ |
| 226 | 2,6-Cl₂ | CH₂C₆H₅ |
| 227 | 2,4-F₂ | CH₂C₆H₅ |
| 228 | 2,6-F₂ | CH₂C₆H₅ |
| 229 | 2-F-3-Cl | CH₂C₆H₅ |
| 230 | 2-F-4-Cl | CH₂C₆H₅ |
| 231 | 2-Cl-3-F | CH₂C₆H₅ |
| 232 | 2-Cl-4-F | CH₂C₆H₅ |
| 233 | 2-CH₃ | CH₂C₆H₅ |
| 234 | 3-CH₃ | CH₂C₆H₅ |
| 235 | 4-CH₃ | CH₂C₆H₅ |
| 236 | 4-CF₃ | CH₂C₆H₅ |
| 237 | 2-CHF₂ | CH₂C₆H₅ |
| 238 | 3-CHF₂ | CH₂C₆H₅ |
| 239 | 4-CHF₂ | CH₂C₆H₅ |
| 240 | 2-OCH₃ | CH₂C₆H₅ |
| 241 | 4-OCH₃ | CH₂C₆H₅ |
| 242 | 2-OCF₃ | CH₂C₆H₅ |
| 243 | 4-OCF₃ | CH₂C₆H₅ |
| 244 | 2-OCHF₂ | CH₂C₆H₅ |
| 245 | 3-OCHF₂ | CH₂C₆H₅ |
| 246 | 4-OCHF₂ | CH₂C₆H₅ |
| 247 | 2,4-(CH₃)₂ | CH₂C₆H₅ |
| 248 | 2,4,6-(CH₃)₃ | CH₂C₆H₅ |
| 249 | —* | CF₃ |
| 250 | 2-Cl | CF₃ |
| 251 | 3-Cl | CF₃ |
| 252 | 4-Cl | CF₃ |
| 253 | 2-F | CF₃ |
| 254 | 3-F | CF₃ |
| 255 | 4-F | CF₃ |
| 256 | 2,4-Cl₂ | CF₃ |
| 257 | 2,6-Cl₂ | CF₃ |
| 258 | 2,4-F₂ | CF₃ |
| 259 | 2,6-F₂ | CF₃ |
| 260 | 2-F-3-Cl | CF₃ |
| 261 | 2-F-4-Cl | CF₃ |
| 262 | 2-Cl-3-F | CF₃ |
| 263 | 2-Cl-4-F | CF₃ |
| 264 | 2-CH₃ | CF₃ |
| 265 | 3-CH₃ | CF₃ |
| 266 | 4-CH₃ | CF₃ |
| 267 | 4-CF₃ | CF₃ |
| 268 | 2-CHF₂ | CF₃ |
| 269 | 3-CHF₂ | CF₃ |
| 270 | 4-CHF₂ | CF₃ |
| 271 | 2-OCH₃ | CF₃ |
| 272 | 4-OCH₃ | CF₃ |
| 273 | 2-OCF₃ | CF₃ |
| 274 | 4-OCF₃ | CF₃ |
| 275 | 2-OCHF₂ | CF₃ |
| 276 | 3-OCHF₂ | CF₃ |
| 277 | 4-OCHF₂ | CF₃ |
| 278 | 2,4-(CH₃)₂ | CF₃ |
| 279 | 2,4,6-(CH₃)₃ | CF₃ |
| 280 | —* | CHF₂ |
| 281 | 2-Cl | CHF₂ |
| 282 | 3-Cl | CHF₂ |
| 283 | 4-Cl | CHF₂ |
| 284 | 2-F | CHF₂ |
| 285 | 3-F | CHF₂ |
| 286 | 4-F | CHF₂ |
| 287 | 2,4-Cl₂ | CHF₂ |
| 288 | 2,6-Cl₂ | CHF₂ |
| 289 | 2,4-F₂ | CHF₂ |
| 290 | 2,6-F₂ | CHF₂ |
| 291 | 2-F-3-Cl | CHF₂ |
| 292 | 2-F-4-Cl | CHF₂ |
| 293 | 2-Cl-3-F | CHF₂ |
| 294 | 2-Cl-4-F | CHF₂ |
| 295 | 2-CH₃ | CHF₂ |
| 296 | 3-CH₃ | CHF₂ |
| 297 | 4-CH₃ | CHF₂ |
| 298 | 4-CF₃ | CHF₂ |
| 299 | 2-CHF₂ | CHF₂ |
| 300 | 3-CHF₂ | CHF₂ |
| 301 | 4-CHF₂ | CHF₂ |
| 302 | 2-OCH₃ | CHF₂ |
| 303 | 4-OCH₃ | CHF₂ |
| 304 | 2-OCF₃ | CHF₂ |
| 305 | 4-OCF₃ | CHF₂ |
| 306 | 2-OCHF₂ | CHF₂ |
| 307 | 3-OCHF₂ | CHF₂ |
| 308 | 4-OCHF₂ | CHF₂ |
| 309 | 2,4-(CH₃)₂ | CHF₂ |
| 310 | 2,4,6-(CH₃)₃ | CHF₂ |
| 311 | —* | C≡CH |
| 312 | 2-Cl | C≡CH |
| 313 | 3-Cl | C≡CH |
| 314 | 4-Cl | C≡CH |
| 315 | 2-F | C≡CH |
| 316 | 3-F | C≡CH |
| 317 | 4-F | C≡CH |
| 318 | 2,4-Cl₂ | C≡CH |
| 319 | 2,6-Cl₂ | C≡CH |
| 320 | 2,4-F₂ | C≡CH |
| 321 | 2,6-F₂ | C≡CH |
| 322 | 2-F-3-Cl | C≡CH |

TABLE A1-continued

| No. | $R^4_m$ | $R^1$ |
|---|---|---|
| 323 | 2-F-4-Cl | C≡CH |
| 324 | 2-Cl-3-F | C≡CH |
| 325 | 2-Cl-4-F | C≡CH |
| 326 | 2-CH$_3$ | C≡CH |
| 327 | 3-CH$_3$ | C≡CH |
| 328 | 4-CH$_3$ | C≡CH |
| 329 | 4-CF$_3$ | C≡CH |
| 330 | 2-CHF$_2$ | C≡CH |
| 331 | 3-CHF$_2$ | C≡CH |
| 332 | 4-CHF$_2$ | C≡CH |
| 333 | 2-OCH$_3$ | C≡CH |
| 334 | 4-OCH$_3$ | C≡CH |
| 335 | 2-OCF$_3$ | C≡CH |
| 336 | 4-OCF$_3$ | C≡CH |
| 337 | 2-OCHF$_2$ | C≡CH |
| 338 | 3-OCHF$_2$ | C≡CH |
| 339 | 4-OCHF$_2$ | C≡CH |
| 340 | 2,4-(CH$_3$)$_2$ | C≡CH |
| 341 | 2,4,6-(CH$_3$)$_3$ | C≡CH |
| 342 | —* | C≡CCH$_3$ |
| 343 | 2-Cl | C≡CCH$_3$ |
| 344 | 3-Cl | C≡CCH$_3$ |
| 345 | 4-Cl | C≡CCH$_3$ |
| 346 | 2-F | C≡CCH$_3$ |
| 347 | 3-F | C≡CCH$_3$ |
| 348 | 4-F | C≡CCH$_3$ |
| 349 | 2,4-Cl$_2$ | C≡CCH$_3$ |
| 350 | 2,6-Cl$_2$ | C≡CCH$_3$ |
| 351 | 2,4-F$_2$ | C≡CCH$_3$ |
| 352 | 2,6-F$_2$ | C≡CCH$_3$ |
| 353 | 2-F-3-Cl | C≡CCH$_3$ |
| 354 | 2-F-4-Cl | C≡CCH$_3$ |
| 355 | 2-Cl-3-F | C≡CCH$_3$ |
| 356 | 2-Cl-4-F | C≡CCH$_3$ |
| 357 | 2-CH$_3$ | C≡CCH$_3$ |
| 358 | 3-CH$_3$ | C≡CCH$_3$ |
| 359 | 4-CH$_3$ | C≡CCH$_3$ |
| 360 | 4-CF$_3$ | C≡CCH$_3$ |
| 361 | 2-CHF$_2$ | C≡CCH$_3$ |
| 362 | 3-CHF$_2$ | C≡CCH$_3$ |
| 363 | 4-CHF$_2$ | C≡CCH$_3$ |
| 364 | 2-OCH$_3$ | C≡CCH$_3$ |
| 365 | 4-OCH$_3$ | C≡CCH$_3$ |
| 366 | 2-OCF$_3$ | C≡CCH$_3$ |
| 367 | 4-OCF$_3$ | C≡CCH$_3$ |
| 368 | 2-OCHF$_2$ | C≡CCH$_3$ |
| 369 | 3-OCHF$_2$ | C≡CCH$_3$ |
| 370 | 4-OCHF$_2$ | C≡CCH$_3$ |
| 371 | 2,4-(CH$_3$)$_2$ | C≡CCH$_3$ |
| 372 | 2,4,6-(CH$_3$)$_3$ | C≡CCH$_3$ |
| 373 | —* | CH$_2$CH$_2$CH$_2$CH$_3$ |
| 374 | 2-Cl | CH$_2$CH$_2$CH$_2$CH$_3$ |
| 375 | 3-Cl | CH$_2$CH$_2$CH$_2$CH$_3$ |
| 376 | 4-Cl | CH$_2$CH$_2$CH$_2$CH$_3$ |
| 377 | 2-F | CH$_2$CH$_2$CH$_2$CH$_3$ |
| 378 | 3-F | CH$_2$CH$_2$CH$_2$CH$_3$ |
| 379 | 4-F | CH$_2$CH$_2$CH$_2$CH$_3$ |
| 380 | 2,4-Cl$_2$ | CH$_2$CH$_2$CH$_2$CH$_3$ |
| 381 | 2,6-Cl$_2$ | CH$_2$CH$_2$CH$_2$CH$_3$ |
| 382 | 2,4-F$_2$ | CH$_2$CH$_2$CH$_2$CH$_3$ |
| 383 | 2,6-F$_2$ | CH$_2$CH$_2$CH$_2$CH$_3$ |
| 384 | 2-F-3-Cl | CH$_2$CH$_2$CH$_2$CH$_3$ |
| 385 | 2-F-4-Cl | CH$_2$CH$_2$CH$_2$CH$_3$ |
| 386 | 2-Cl-3-F | CH$_2$CH$_2$CH$_2$CH$_3$ |
| 387 | 2-Cl-4-F | CH$_2$CH$_2$CH$_2$CH$_3$ |
| 388 | 2-CH$_3$ | CH$_2$CH$_2$CH$_2$CH$_3$ |
| 389 | 3-CH$_3$ | CH$_2$CH$_2$CH$_2$CH$_3$ |
| 390 | 4-CH$_3$ | CH$_2$CH$_2$CH$_2$CH$_3$ |
| 391 | 4-CF$_3$ | CH$_2$CH$_2$CH$_2$CH$_3$ |
| 392 | 2-CHF$_2$ | CH$_2$CH$_2$CH$_2$CH$_3$ |
| 393 | 3-CHF$_2$ | CH$_2$CH$_2$CH$_2$CH$_3$ |
| 394 | 4-CHF$_2$ | CH$_2$CH$_2$CH$_2$CH$_3$ |
| 395 | 2-OCH$_3$ | CH$_2$CH$_2$CH$_2$CH$_3$ |
| 396 | 4-OCH$_3$ | CH$_2$CH$_2$CH$_2$CH$_3$ |
| 397 | 2-OCF$_3$ | CH$_2$CH$_2$CH$_2$CH$_3$ |
| 398 | 4-OCF$_3$ | CH$_2$CH$_2$CH$_2$CH$_3$ |
| 399 | 2-OCHF$_2$ | CH$_2$CH$_2$CH$_2$CH$_3$ |
| 400 | 3-OCHF$_2$ | CH$_2$CH$_2$CH$_2$CH$_3$ |
| 401 | 4-OCHF$_2$ | CH$_2$CH$_2$CH$_2$CH$_3$ |
| 402 | 2,4-(CH$_3$)$_2$ | CH$_2$CH$_2$CH$_2$CH$_3$ |
| 403 | 2,4,6-(CH$_3$)$_3$ | CH$_2$CH$_2$CH$_2$CH$_3$ |
| 404 | —* | C(CH$_3$)$_3$ |
| 405 | 2-Cl | C(CH$_3$)$_3$ |
| 406 | 3-Cl | C(CH$_3$)$_3$ |
| 407 | 4-Cl | C(CH$_3$)$_3$ |
| 408 | 2-F | C(CH$_3$)$_3$ |
| 409 | 3-F | C(CH$_3$)$_3$ |
| 410 | 4-F | C(CH$_3$)$_3$ |
| 411 | 2,4-Cl$_2$ | C(CH$_3$)$_3$ |
| 412 | 2,6-Cl$_2$ | C(CH$_3$)$_3$ |
| 413 | 2,4-F$_2$ | C(CH$_3$)$_3$ |
| 414 | 2,6-F$_2$ | C(CH$_3$)$_3$ |
| 415 | 2-F-3-Cl | C(CH$_3$)$_3$ |
| 416 | 2-F-4-Cl | C(CH$_3$)$_3$ |
| 417 | 2-Cl-3-F | C(CH$_3$)$_3$ |
| 418 | 2-Cl-4-F | C(CH$_3$)$_3$ |
| 419 | 2-CH$_3$ | C(CH$_3$)$_3$ |
| 420 | 3-CH$_3$ | C(CH$_3$)$_3$ |
| 421 | 4-CH$_3$ | C(CH$_3$)$_3$ |
| 422 | 4-CF$_3$ | C(CH$_3$)$_3$ |
| 423 | 2-CHF$_2$ | C(CH$_3$)$_3$ |
| 424 | 3-CHF$_2$ | C(CH$_3$)$_3$ |
| 425 | 4-CHF$_2$ | C(CH$_3$)$_3$ |
| 426 | 2-OCH$_3$ | C(CH$_3$)$_3$ |
| 427 | 4-OCH$_3$ | C(CH$_3$)$_3$ |
| 428 | 2-OCF$_3$ | C(CH$_3$)$_3$ |
| 429 | 4-OCF$_3$ | C(CH$_3$)$_3$ |
| 430 | 2-OCHF$_2$ | C(CH$_3$)$_3$ |
| 431 | 3-OCHF$_2$ | C(CH$_3$)$_3$ |
| 432 | 4-OCHF$_2$ | C(CH$_3$)$_3$ |
| 433 | 2,4-(CH$_3$)$_2$ | C(CH$_3$)$_3$ |
| 434 | 2,4,6-(CH$_3$)$_3$ | C(CH$_3$)$_3$ |
| 435 | —* | CH$_2$CH=CH$_2$ |
| 436 | 2-Cl | CH$_2$CH=CH$_2$ |
| 437 | 3-Cl | CH$_2$CH=CH$_2$ |
| 438 | 4-Cl | CH$_2$CH=CH$_2$ |
| 439 | 2-F | CH$_2$CH=CH$_2$ |
| 440 | 3-F | CH$_2$CH=CH$_2$ |
| 441 | 4-F | CH$_2$CH=CH$_2$ |
| 442 | 2,4-Cl$_2$ | CH$_2$CH=CH$_2$ |
| 443 | 2,6-Cl$_2$ | CH$_2$CH=CH$_2$ |
| 444 | 2,4-F$_2$ | CH$_2$CH=CH$_2$ |
| 445 | 2,6-F$_2$ | CH$_2$CH=CH$_2$ |
| 446 | 2-F-3-Cl | CH$_2$CH=CH$_2$ |
| 447 | 2-F-4-Cl | CH$_2$CH=CH$_2$ |
| 448 | 2-Cl-3-F | CH$_2$CH=CH$_2$ |
| 449 | 2-Cl-4-F | CH$_2$CH=CH$_2$ |
| 450 | 2-CH$_3$ | CH$_2$CH=CH$_2$ |
| 451 | 3-CH$_3$ | CH$_2$CH=CH$_2$ |
| 452 | 4-CH$_3$ | CH$_2$CH=CH$_2$ |
| 453 | 4-CF$_3$ | CH$_2$CH=CH$_2$ |
| 454 | 2-CHF$_2$ | CH$_2$CH=CH$_2$ |
| 455 | 3-CHF$_2$ | CH$_2$CH=CH$_2$ |
| 456 | 4-CHF$_2$ | CH$_2$CH=CH$_2$ |
| 457 | 2-OCH$_3$ | CH$_2$CH=CH$_2$ |
| 458 | 4-OCH$_3$ | CH$_2$CH=CH$_2$ |
| 459 | 2-OCF$_3$ | CH$_2$CH=CH$_2$ |
| 460 | 4-OCF$_3$ | CH$_2$CH=CH$_2$ |
| 461 | 2-OCHF$_2$ | CH$_2$CH=CH$_2$ |
| 462 | 3-OCHF$_2$ | CH$_2$CH=CH$_2$ |
| 463 | 4-OCHF$_2$ | CH$_2$CH=CH$_2$ |
| 464 | 2,4-(CH$_3$)$_2$ | CH$_2$CH=CH$_2$ |
| 465 | 2,4,6-(CH$_3$)$_3$ | CH$_2$CH=CH$_2$ |
| 466 | —* | CH$_2$CH=CHCH$_3$ |
| 467 | 2-Cl | CH$_2$CH=CHCH$_3$ |
| 468 | 3-Cl | CH$_2$CH=CHCH$_3$ |
| 469 | 4-Cl | CH$_2$CH=CHCH$_3$ |
| 470 | 2-F | CH$_2$CH=CHCH$_3$ |
| 471 | 3-F | CH$_2$CH=CHCH$_3$ |
| 472 | 4-F | CH$_2$CH=CHCH$_3$ |
| 473 | 2,4-Cl$_2$ | CH$_2$CH=CHCH$_3$ |
| 474 | 2,6-Cl$_2$ | CH$_2$CH=CHCH$_3$ |
| 475 | 2,4-F$_2$ | CH$_2$CH=CHCH$_3$ |
| 476 | 2,6-F$_2$ | CH$_2$CH=CHCH$_3$ |
| 477 | 2-F-3-Cl | CH$_2$CH=CHCH$_3$ |
| 478 | 2-F-4-Cl | CH$_2$CH=CHCH$_3$ |

TABLE A1-continued

| No. | $R^4_m$ | $R^1$ |
|---|---|---|
| 479 | 2-Cl-3-F | $CH_2CH=CHCH_3$ |
| 480 | 2-Cl-4-F | $CH_2CH=CHCH_3$ |
| 481 | 2-$CH_3$ | $CH_2CH=CHCH_3$ |
| 482 | 3-$CH_3$ | $CH_2CH=CHCH_3$ |
| 483 | 4-$CH_3$ | $CH_2CH=CHCH_3$ |
| 484 | 4-$CF_3$ | $CH_2CH=CHCH_3$ |
| 485 | 2-$CHF_2$ | $CH_2CH=CHCH_3$ |
| 486 | 3-$CHF_2$ | $CH_2CH=CHCH_3$ |
| 487 | 4-$CHF_2$ | $CH_2CH=CHCH_3$ |
| 488 | 2-$OCH_3$ | $CH_2CH=CHCH_3$ |
| 489 | 4-$OCH_3$ | $CH_2CH=CHCH_3$ |
| 490 | 2-$OCF_3$ | $CH_2CH=CHCH_3$ |
| 491 | 4-$OCF_3$ | $CH_2CH=CHCH_3$ |
| 492 | 2-$OCHF_2$ | $CH_2CH=CHCH_3$ |
| 493 | 3-$OCHF_2$ | $CH_2CH=CHCH_3$ |
| 494 | 4-$OCHF_2$ | $CH_2CH=CHCH_3$ |
| 495 | 2,4-$(CH_3)_2$ | $CH_2CH=CHCH_3$ |
| 496 | 2,4,6-$(CH_3)_3$ | $CH_2CH=CHCH_3$ |
| 497 | —* | $CH_2C(CH_3)=CH_2$ |
| 498 | 2-Cl | $CH_2C(CH_3)=CH_2$ |
| 499 | 3-Cl | $CH_2C(CH_3)=CH_2$ |
| 500 | 4-Cl | $CH_2C(CH_3)=CH_2$ |
| 501 | 2-F | $CH_2C(CH_3)=CH_2$ |
| 502 | 3-F | $CH_2C(CH_3)=CH_2$ |
| 503 | 4-F | $CH_2C(CH_3)=CH_2$ |
| 504 | 2,4-$Cl_2$ | $CH_2C(CH_3)=CH_2$ |
| 505 | 2,6-$Cl_2$ | $CH_2C(CH_3)=CH_2$ |
| 506 | 2,4-$F_2$ | $CH_2C(CH_3)=CH_2$ |
| 507 | 2,6-$F_2$ | $CH_2C(CH_3)=CH_2$ |
| 508 | 2-F-3-Cl | $CH_2C(CH_3)=CH_2$ |
| 509 | 2-F-4-Cl | $CH_2C(CH_3)=CH_2$ |
| 510 | 2-Cl-3-F | $CH_2C(CH_3)=CH_2$ |
| 511 | 2-Cl-4-F | $CH_2C(CH_3)=CH_2$ |
| 512 | 2-$CH_3$ | $CH_2C(CH_3)=CH_2$ |
| 513 | 3-$CH_3$ | $CH_2C(CH_3)=CH_2$ |
| 514 | 4-$CH_3$ | $CH_2C(CH_3)=CH_2$ |
| 515 | 4-$CF_3$ | $CH_2C(CH_3)=CH_2$ |
| 516 | 2-$CHF_2$ | $CH_2C(CH_3)=CH_2$ |
| 517 | 3-$CHF_2$ | $CH_2C(CH_3)=CH_2$ |
| 518 | 4-$CHF_2$ | $CH_2C(CH_3)=CH_2$ |
| 519 | 2-$OCH_3$ | $CH_2C(CH_3)=CH_2$ |
| 520 | 4-$OCH_3$ | $CH_2C(CH_3)=CH_2$ |
| 521 | 2-$OCF_3$ | $CH_2C(CH_3)=CH_2$ |
| 522 | 4-$OCF_3$ | $CH_2C(CH_3)=CH_2$ |
| 523 | 2-$OCHF_2$ | $CH_2C(CH_3)=CH_2$ |
| 524 | 3-$OCHF_2$ | $CH_2C(CH_3)=CH_2$ |
| 525 | 4-$OCHF_2$ | $CH_2C(CH_3)=CH_2$ |
| 526 | 2,4-$(CH_3)_2$ | $CH_2C(CH_3)=CH_2$ |
| 527 | 2,4,6-$(CH_3)_3$ | $CH_2C(CH_3)=CH_2$ |
| 528 | —* | $CH=CHCH_3$ |
| 529 | 2-Cl | $CH=CHCH_3$ |
| 530 | 3-Cl | $CH=CHCH_3$ |
| 531 | 4-Cl | $CH=CHCH_3$ |
| 532 | 2-F | $CH=CHCH_3$ |
| 533 | 3-F | $CH=CHCH_3$ |
| 534 | 4-F | $CH=CHCH_3$ |
| 535 | 2,4-$Cl_2$ | $CH=CHCH_3$ |
| 536 | 2,6-$Cl_2$ | $CH=CHCH_3$ |
| 537 | 2,4-$F_2$ | $CH=CHCH_3$ |
| 538 | 2,6-$F_2$ | $CH=CHCH_3$ |
| 539 | 2-F-3-Cl | $CH=CHCH_3$ |
| 540 | 2-F-4-Cl | $CH=CHCH_3$ |
| 541 | 2-Cl-3-F | $CH=CHCH_3$ |
| 542 | 2-Cl-4-F | $CH=CHCH_3$ |
| 543 | 2-$CH_3$ | $CH=CHCH_3$ |
| 544 | 3-$CH_3$ | $CH=CHCH_3$ |
| 545 | 4-$CH_3$ | $CH=CHCH_3$ |
| 546 | 4-$CF_3$ | $CH=CHCH_3$ |
| 547 | 2-$CHF_2$ | $CH=CHCH_3$ |
| 548 | 3-$CHF_2$ | $CH=CHCH_3$ |
| 549 | 4-$CHF_2$ | $CH=CHCH_3$ |
| 550 | 2-$OCH_3$ | $CH=CHCH_3$ |
| 551 | 4-$OCH_3$ | $CH=CHCH_3$ |
| 552 | 2-$OCF_3$ | $CH=CHCH_3$ |
| 553 | 4-$OCF_3$ | $CH=CHCH_3$ |
| 554 | 2-$OCHF_2$ | $CH=CHCH_3$ |
| 555 | 3-$OCHF_2$ | $CH=CHCH_3$ |
| 556 | 4-$OCHF_2$ | $CH=CHCH_3$ |
| 557 | 2,4-$(CH_3)_2$ | $CH=CHCH_3$ |
| 558 | 2,4,6-$(CH_3)_3$ | $CH=CHCH_3$ |
| 559 | —* | $C(CH_3)=CH_2$ |
| 560 | 2-Cl | $C(CH_3)=CH_2$ |
| 561 | 3-Cl | $C(CH_3)=CH_2$ |
| 562 | 4-Cl | $C(CH_3)=CH_2$ |
| 563 | 2-F | $C(CH_3)=CH_2$ |
| 564 | 3-F | $C(CH_3)=CH_2$ |
| 565 | 4-F | $C(CH_3)=CH_2$ |
| 566 | 2,4-$Cl_2$ | $C(CH_3)=CH_2$ |
| 567 | 2,6-$Cl_2$ | $C(CH_3)=CH_2$ |
| 568 | 2,4-$F_2$ | $C(CH_3)=CH_2$ |
| 569 | 2,6-$F_2$ | $C(CH_3)=CH_2$ |
| 570 | 2-F-3-Cl | $C(CH_3)=CH_2$ |
| 571 | 2-F-4-Cl | $C(CH_3)=CH_2$ |
| 572 | 2-Cl-3-F | $C(CH_3)=CH_2$ |
| 573 | 2-Cl-4-F | $C(CH_3)=CH_2$ |
| 574 | 2-$CH_3$ | $C(CH_3)=CH_2$ |
| 575 | 3-$CH_3$ | $C(CH_3)=CH_2$ |
| 576 | 4-$CH_3$ | $C(CH_3)=CH_2$ |
| 577 | 4-$CF_3$ | $C(CH_3)=CH_2$ |
| 578 | 2-$CHF_2$ | $C(CH_3)=CH_2$ |
| 579 | 3-$CHF_2$ | $C(CH_3)=CH_2$ |
| 580 | 4-$CHF_2$ | $C(CH_3)=CH_2$ |
| 581 | 2-$OCH_3$ | $C(CH_3)=CH_2$ |
| 582 | 4-$OCH_3$ | $C(CH_3)=CH_2$ |
| 583 | 2-$OCF_3$ | $C(CH_3)=CH_2$ |
| 584 | 4-$OCF_3$ | $C(CH_3)=CH_2$ |
| 585 | 2-$OCHF_2$ | $C(CH_3)=CH_2$ |
| 586 | 3-$OCHF_2$ | $C(CH_3)=CH_2$ |
| 587 | 4-$OCHF_2$ | $C(CH_3)=CH_2$ |
| 588 | 2,4-$(CH_3)_2$ | $C(CH_3)=CH_2$ |
| 589 | 2,4,6-$(CH_3)_3$ | $C(CH_3)=CH_2$ |
| 590 | —* | $CH=CH_2$ |
| 591 | 2-Cl | $CH=CH_2$ |
| 592 | 3-Cl | $CH=CH_2$ |
| 593 | 4-Cl | $CH=CH_2$ |
| 594 | 2-F | $CH=CH_2$ |
| 595 | 3-F | $CH=CH_2$ |
| 596 | 4-F | $CH=CH_2$ |
| 597 | 2,4-$Cl_2$ | $CH=CH_2$ |
| 598 | 2,6-$Cl_2$ | $CH=CH_2$ |
| 599 | 2,4-$F_2$ | $CH=CH_2$ |
| 600 | 2,6-$F_2$ | $CH=CH_2$ |
| 601 | 2-F-3-Cl | $CH=CH_2$ |
| 602 | 2-F-4-Cl | $CH=CH_2$ |
| 603 | 2-Cl-3-F | $CH=CH_2$ |
| 604 | 2-Cl-4-F | $CH=CH_2$ |
| 605 | 2-$CH_3$ | $CH=CH_2$ |
| 606 | 3-$CH_3$ | $CH=CH_2$ |
| 607 | 4-$CH_3$ | $CH=CH_2$ |
| 608 | 4-$CF_3$ | $CH=CH_2$ |
| 609 | 2-$CHF_2$ | $CH=CH_2$ |
| 610 | 3-$CHF_2$ | $CH=CH_2$ |
| 611 | 4-$CHF_2$ | $CH=CH_2$ |
| 612 | 2-$OCH_3$ | $CH=CH_2$ |
| 613 | 4-$OCH_3$ | $CH=CH_2$ |
| 614 | 2-$OCF_3$ | $CH=CH_2$ |
| 615 | 4-$OCF_3$ | $CH=CH_2$ |
| 616 | 2-$OCHF_2$ | $CH=CH_2$ |
| 617 | 3-$OCHF_2$ | $CH=CH_2$ |
| 618 | 4-$OCHF_2$ | $CH=CH_2$ |
| 619 | 2,4-$(CH_3)_2$ | $CH=CH_2$ |
| 620 | 2,4,6-$(CH_3)_3$ | $CH=CH_2$ |
| 621 | —* | cyclohexyl |
| 622 | 2-Cl | cyclohexyl |
| 623 | 3-Cl | cyclohexyl |
| 624 | 4-Cl | cyclohexyl |
| 625 | 2-F | cyclohexyl |
| 626 | 3-F | cyclohexyl |
| 627 | 4-F | cyclohexyl |
| 628 | 2,4-$Cl_2$ | cyclohexyl |
| 629 | 2,6-$Cl_2$ | cyclohexyl |
| 630 | 2,4-$F_2$ | cyclohexyl |
| 631 | 2,6-$F_2$ | cyclohexyl |
| 632 | 2-F-3-Cl | cyclohexyl |
| 633 | 2-F-4-Cl | cyclohexyl |
| 634 | 2-Cl-3-F | cyclohexyl |

TABLE A1-continued

| No. | $R^4_m$ | $R^1$ |
|---|---|---|
| 635 | 2-Cl-4-F | cyclohexyl |
| 636 | 2-CH₃ | cyclohexyl |
| 637 | 3-CH₃ | cyclohexyl |
| 638 | 4-CH₃ | cyclohexyl |
| 639 | 4-CF₃ | cyclohexyl |
| 640 | 2-CHF₂ | cyclohexyl |
| 641 | 3-CHF₂ | cyclohexyl |
| 642 | 4-CHF₂ | cyclohexyl |
| 643 | 2-OCH₃ | cyclohexyl |
| 644 | 4-OCH₃ | cyclohexyl |
| 645 | 2-OCF₃ | cyclohexyl |
| 646 | 4-OCF₃ | cyclohexyl |
| 647 | 2-OCHF₂ | cyclohexyl |
| 648 | 3-OCHF₂ | cyclohexyl |
| 649 | 4-OCHF₂ | cyclohexyl |
| 650 | 2,4-(CH₃)₂ | cyclohexyl |
| 651 | 2,4,6-(CH₃)₃ | cyclohexyl |
| 652 | —* | cyclopentyl |
| 653 | 2-Cl | cyclopentyl |
| 654 | 3-Cl | cyclopentyl |
| 655 | 4-Cl | cyclopentyl |
| 656 | 2-F | cyclopentyl |
| 657 | 3-F | cyclopentyl |
| 658 | 4-F | cyclopentyl |
| 659 | 2,4-Cl₂ | cyclopentyl |
| 660 | 2,6-Cl₂ | cyclopentyl |
| 661 | 2,4-F₂ | cyclopentyl |
| 662 | 2,6-F₂ | cyclopentyl |
| 663 | 2-F-3-Cl | cyclopentyl |
| 664 | 2-F-4-Cl | cyclopentyl |
| 665 | 2-Cl-3-F | cyclopentyl |
| 666 | 2-Cl-4-F | cyclopentyl |
| 667 | 2-CH₃ | cyclopentyl |
| 668 | 3-CH₃ | cyclopentyl |
| 669 | 4-CH₃ | cyclopentyl |
| 670 | 4-CF₃ | cyclopentyl |
| 671 | 2-CHF₂ | cyclopentyl |
| 672 | 3-CHF₂ | cyclopentyl |
| 673 | 4-CHF₂ | cyclopentyl |
| 674 | 2-OCH₃ | cyclopentyl |
| 675 | 4-OCH₃ | cyclopentyl |
| 676 | 2-OCF₃ | cyclopentyl |
| 677 | 4-OCF₃ | cyclopentyl |
| 678 | 2-OCHF₂ | cyclopentyl |
| 679 | 3-OCHF₂ | cyclopentyl |
| 680 | 4-OCHF₂ | cyclopentyl |
| 681 | 2,4-(CH₃)₂ | cyclopentyl |
| 682 | 2,4,6-(CH₃)₃ | cyclopentyl |
| 683 | —* | CH(CH₃)CH₂CH₃ |
| 684 | 2-Cl | CH(CH₃)CH₂CH₃ |
| 685 | 3-Cl | CH(CH₃)CH₂CH₃ |
| 686 | 4-Cl | CH(CH₃)CH₂CH₃ |
| 687 | 2-F | CH(CH₃)CH₂CH₃ |
| 688 | 3-F | CH(CH₃)CH₂CH₃ |
| 689 | 4-F | CH(CH₃)CH₂CH₃ |
| 690 | 2,4-Cl₂ | CH(CH₃)CH₂CH₃ |
| 691 | 2,6-Cl₂ | CH(CH₃)CH₂CH₃ |
| 692 | 2,4-F₂ | CH(CH₃)CH₂CH₃ |
| 693 | 2,6-F₂ | CH(CH₃)CH₂CH₃ |
| 694 | 2-F-3-Cl | CH(CH₃)CH₂CH₃ |
| 695 | 2-F-4-Cl | CH(CH₃)CH₂CH₃ |
| 696 | 2-Cl-3-F | CH(CH₃)CH₂CH₃ |
| 697 | 2-Cl-4-F | CH(CH₃)CH₂CH₃ |
| 698 | 2-CH₃ | CH(CH₃)CH₂CH₃ |
| 699 | 3-CH₃ | CH(CH₃)CH₂CH₃ |
| 700 | 4-CH₃ | CH(CH₃)CH₂CH₃ |
| 701 | 4-CF₃ | CH(CH₃)CH₂CH₃ |
| 702 | 2-CHF₂ | CH(CH₃)CH₂CH₃ |
| 703 | 3-CHF₂ | CH(CH₃)CH₂CH₃ |
| 704 | 4-CHF₂ | CH(CH₃)CH₂CH₃ |
| 705 | 2-OCH₃ | CH(CH₃)CH₂CH₃ |
| 706 | 4-OCH₃ | CH(CH₃)CH₂CH₃ |
| 707 | 2-OCF₃ | CH(CH₃)CH₂CH₃ |
| 708 | 4-OCF₃ | CH(CH₃)CH₂CH₃ |
| 709 | 2-OCHF₂ | CH(CH₃)CH₂CH₃ |
| 710 | 3-OCHF₂ | CH(CH₃)CH₂CH₃ |
| 711 | 4-OCHF₂ | CH(CH₃)CH₂CH₃ |
| 712 | 2,4-(CH₃)₂ | CH(CH₃)CH₂CH₃ |
| 713 | 2,4,6-(CH₃)₃ | CH(CH₃)CH₂CH₃ |
| 714 | —* | CH₂CH(CH₃)₂ |
| 715 | 2-Cl | CH₂CH(CH₃)₂ |
| 716 | 3-Cl | CH₂CH(CH₃)₂ |
| 717 | 4-Cl | CH₂CH(CH₃)₂ |
| 718 | 2-F | CH₂CH(CH₃)₂ |
| 719 | 3-F | CH₂CH(CH₃)₂ |
| 720 | 4-F | CH₂CH(CH₃)₂ |
| 721 | 2,4-Cl₂ | CH₂CH(CH₃)₂ |
| 722 | 2,6-Cl₂ | CH₂CH(CH₃)₂ |
| 723 | 2,4-F₂ | CH₂CH(CH₃)₂ |
| 724 | 2,6-F₂ | CH₂CH(CH₃)₂ |
| 725 | 2-F-3-Cl | CH₂CH(CH₃)₂ |
| 726 | 2-F-4-Cl | CH₂CH(CH₃)₂ |
| 727 | 2-Cl-3-F | CH₂CH(CH₃)₂ |
| 728 | 2-Cl-4-F | CH₂CH(CH₃)₂ |
| 729 | 2-CH₃ | CH₂CH(CH₃)₂ |
| 730 | 3-CH₃ | CH₂CH(CH₃)₂ |
| 731 | 4-CH₃ | CH₂CH(CH₃)₂ |
| 732 | 4-CF₃ | CH₂CH(CH₃)₂ |
| 733 | 2-CHF₂ | CH₂CH(CH₃)₂ |
| 734 | 3-CHF₂ | CH₂CH(CH₃)₂ |
| 735 | 4-CHF₂ | CH₂CH(CH₃)₂ |
| 736 | 2-OCH₃ | CH₂CH(CH₃)₂ |
| 737 | 4-OCH₃ | CH₂CH(CH₃)₂ |
| 738 | 2-OCF₃ | CH₂CH(CH₃)₂ |
| 739 | 4-OCF₃ | CH₂CH(CH₃)₂ |
| 740 | 2-OCHF₂ | CH₂CH(CH₃)₂ |
| 741 | 3-OCHF₂ | CH₂CH(CH₃)₂ |
| 742 | 4-OCHF₂ | CH₂CH(CH₃)₂ |
| 743 | 2,4-(CH₃)₂ | CH₂CH(CH₃)₂ |
| 744 | 2,4,6-(CH₃)₃ | CH₂CH(CH₃)₂ |
| 745 | —* | CH₂—C≡CCH₃ |
| 746 | 2-Cl | CH₂—C≡CCH₃ |
| 747 | 3-Cl | CH₂—C≡CCH₃ |
| 748 | 4-Cl | CH₂—C≡CCH₃ |
| 749 | 2-F | CH₂—C≡CCH₃ |
| 750 | 3-F | CH₂—C≡CCH₃ |
| 751 | 4-F | CH₂—C≡CCH₃ |
| 752 | 2,4-Cl₂ | CH₂—C≡CCH₃ |
| 753 | 2,6-Cl₂ | CH₂—C≡CCH₃ |
| 754 | 2,4-F₂ | CH₂—C≡CCH₃ |
| 755 | 2,6-F₂ | CH₂—C≡CCH₃ |
| 756 | 2-F-3-Cl | CH₂—C≡CCH₃ |
| 757 | 2-F-4-Cl | CH₂—C≡CCH₃ |
| 758 | 2-Cl-3-F | CH₂—C≡CCH₃ |
| 759 | 2-Cl-4-F | CH₂—C≡CCH₃ |
| 760 | 2-CH₃ | CH₂—C≡CCH₃ |
| 761 | 3-CH₃ | CH₂—C≡CCH₃ |
| 762 | 4-CH₃ | CH₂—C≡CCH₃ |
| 763 | 4-CF₃ | CH₂—C≡CCH₃ |
| 764 | 2-CHF₂ | CH₂—C≡CCH₃ |
| 765 | 3-CHF₂ | CH₂—C≡CCH₃ |
| 766 | 4-CHF₂ | CH₂—C≡CCH₃ |
| 767 | 2-OCH₃ | CH₂—C≡CCH₃ |
| 768 | 4-OCH₃ | CH₂—C≡CCH₃ |
| 769 | 2-OCF₃ | CH₂—C≡CCH₃ |
| 770 | 4-OCF₃ | CH₂—C≡CCH₃ |
| 771 | 2-OCHF₂ | CH₂—C≡CCH₃ |
| 772 | 3-OCHF₂ | CH₂—C≡CCH₃ |
| 773 | 4-OCHF₂ | CH₂—C≡CCH₃ |
| 774 | 2,4-(CH₃)₂ | CH₂—C≡CCH₃ |
| 775 | 2,4,6-(CH₃)₃ | CH₂—C≡CCH₃ |
| 776 | —* | CH₂—C≡CH |
| 777 | 2-Cl | CH₂—C≡CH |
| 778 | 3-Cl | CH₂—C≡CH |
| 779 | 4-Cl | CH₂—C≡CH |
| 780 | 2-F | CH₂—C≡CH |
| 781 | 3-F | CH₂—C≡CH |
| 782 | 4-F | CH₂—C≡CH |
| 783 | 2,4-Cl₂ | CH₂—C≡CH |
| 784 | 2,6-Cl₂ | CH₂—C≡CH |
| 785 | 2,4-F₂ | CH₂—C≡CH |
| 786 | 2,6-F₂ | CH₂—C≡CH |
| 787 | 2-F-3-Cl | CH₂—C≡CH |
| 788 | 2-F-4-Cl | CH₂—C≡CH |
| 789 | 2-Cl-3-F | CH₂—C≡CH |
| 790 | 2-Cl-4-F | CH₂—C≡CH |

TABLE A1-continued

| No. | $R^4_m$ | $R^1$ |
|---|---|---|
| 791 | 2-CH$_3$ | CH$_2$—C≡CH |
| 792 | 3-CH$_3$ | CH$_2$—C≡CH |
| 793 | 4-CH$_3$ | CH$_2$—C≡CH |
| 794 | 4-CF$_3$ | CH$_2$—C≡CH |
| 795 | 2-CHF$_2$ | CH$_2$—C≡CH |
| 796 | 3-CHF$_2$ | CH$_2$—C≡CH |
| 797 | 4-CHF$_2$ | CH$_2$—C≡CH |
| 798 | 2-OCH$_3$ | CH$_2$—C≡CH |
| 799 | 4-OCH$_3$ | CH$_2$—C≡CH |
| 800 | 2-OCF$_3$ | CH$_2$—C≡CH |
| 801 | 4-OCF$_3$ | CH$_2$—C≡CH |
| 802 | 2-OCHF$_2$ | CH$_2$—C≡CH |
| 803 | 3-OCHF$_2$ | CH$_2$—C≡CH |
| 804 | 4-OCHF$_2$ | CH$_2$—C≡CH |
| 805 | 2,4-(CH$_3$)$_2$ | CH$_2$—C≡CH |
| 806 | 2,4,6-(CH$_3$)$_3$ | CH$_2$—C≡CH |
| 807 | —* | CH(CH$_3$)—c-propyl |
| 808 | 2-Cl | CH(CH$_3$)—c-propyl |
| 809 | 3-Cl | CH(CH$_3$)—c-propyl |
| 810 | 4-Cl | CH(CH$_3$)—c-propyl |
| 811 | 2-F | CH(CH$_3$)—c-propyl |
| 812 | 3-F | CH(CH$_3$)—c-propyl |
| 813 | 4-F | CH(CH$_3$)—c-propyl |
| 814 | 2,4-Cl$_2$ | CH(CH$_3$)—c-propyl |
| 815 | 2,6-Cl$_2$ | CH(CH$_3$)—c-propyl |
| 816 | 2,4-F$_2$ | CH(CH$_3$)—c-propyl |
| 817 | 2,6-F$_2$ | CH(CH$_3$)—c-propyl |
| 818 | 2-F-3-Cl | CH(CH$_3$)—c-propyl |
| 819 | 2-F-4-Cl | CH(CH$_3$)—c-propyl |
| 820 | 2-Cl-3-F | CH(CH$_3$)—c-propyl |
| 821 | 2-Cl-4-F | CH(CH$_3$)—c-propyl |
| 822 | 2-CH$_3$ | CH(CH$_3$)—c-propyl |
| 823 | 3-CH$_3$ | CH(CH$_3$)—c-propyl |
| 824 | 4-CH$_3$ | CH(CH$_3$)—c-propyl |
| 825 | 4-CF$_3$ | CH(CH$_3$)—c-propyl |
| 826 | 2-CHF$_2$ | CH(CH$_3$)—c-propyl |
| 827 | 3-CHF$_2$ | CH(CH$_3$)—c-propyl |
| 828 | 4-CHF$_2$ | CH(CH$_3$)—c-propyl |
| 829 | 2-OCH$_3$ | CH(CH$_3$)—c-propyl |
| 830 | 4-OCH$_3$ | CH(CH$_3$)—c-propyl |
| 831 | 2-OCF$_3$ | CH(CH$_3$)—c-propyl |
| 832 | 4-OCF$_3$ | CH(CH$_3$)—c-propyl |
| 833 | 2-OCHF$_2$ | CH(CH$_3$)—c-propyl |
| 834 | 3-OCHF$_2$ | CH(CH$_3$)—c-propyl |
| 835 | 4-OCHF$_2$ | CH(CH$_3$)—c-propyl |
| 836 | 2,4-(CH$_3$)$_2$ | CH(CH$_3$)—c-propyl |
| 837 | 2,4,6-(CH$_3$)$_3$ | CH(CH$_3$)—c-propyl |
| 838 | —* | CH$_2$—(c-propyl) |
| 839 | 2-Cl | CH$_2$—(c-propyl) |
| 840 | 3-Cl | CH$_2$—(c-propyl) |
| 841 | 4-Cl | CH$_2$—(c-propyl) |
| 842 | 2-F | CH$_2$—(c-propyl) |
| 843 | 3-F | CH$_2$—(c-propyl) |
| 844 | 4-F | CH$_2$—(c-propyl) |
| 845 | 2,4-Cl$_2$ | CH$_2$—(c-propyl) |
| 846 | 2,6-Cl$_2$ | CH$_2$—(c-propyl) |
| 847 | 2,4-F$_2$ | CH$_2$—(c-propyl) |
| 848 | 2,6-F$_2$ | CH$_2$—(c-propyl) |
| 849 | 2-F-3-Cl | CH$_2$—(c-propyl) |
| 850 | 2-F-4-Cl | CH$_2$—(c-propyl) |
| 851 | 2-Cl-3-F | CH$_2$—(c-propyl) |
| 852 | 2-Cl-4-F | CH$_2$—(c-propyl) |
| 853 | 2-CH$_3$ | CH$_2$—(c-propyl) |
| 854 | 3-CH$_3$ | CH$_2$—(c-propyl) |
| 855 | 4-CH$_3$ | CH$_2$—(c-propyl) |
| 856 | 4-CF$_3$ | CH$_2$—(c-propyl) |
| 857 | 2-CHF$_2$ | CH$_2$—(c-propyl) |
| 858 | 3-CHF$_2$ | CH$_2$—(c-propyl) |
| 859 | 4-CHF$_2$ | CH$_2$—(c-propyl) |
| 860 | 2-OCH$_3$ | CH$_2$—(c-propyl) |
| 861 | 4-OCH$_3$ | CH$_2$—(c-propyl) |
| 862 | 2-OCF$_3$ | CH$_2$—(c-propyl) |
| 863 | 4-OCF$_3$ | CH$_2$—(c-propyl) |
| 864 | 2-OCHF$_2$ | CH$_2$—(c-propyl) |
| 865 | 3-OCHF$_2$ | CH$_2$—(c-propyl) |
| 866 | 4-OCHF$_2$ | CH$_2$—(c-propyl) |
| 867 | 2,4-(CH$_3$)$_2$ | CH$_2$—(c-propyl) |
| 868 | 2,4,6-(CH$_3$)$_3$ | CH$_2$—(c-propyl) |
| 869 | —* | 1-Cl—(c-propyl) |
| 870 | 2-Cl | 1-Cl—(c-propyl) |
| 871 | 3-Cl | 1-Cl—(c-propyl) |
| 872 | 4-Cl | 1-Cl—(c-propyl) |
| 873 | 2-F | 1-Cl—(c-propyl) |
| 874 | 3-F | 1-Cl—(c-propyl) |
| 875 | 4-F | 1-Cl—(c-propyl) |
| 876 | 2,4-Cl$_2$ | 1-Cl—(c-propyl) |
| 877 | 2,6-Cl$_2$ | 1-Cl—(c-propyl) |
| 878 | 2,4-F$_2$ | 1-Cl—(c-propyl) |
| 879 | 2,6-F$_2$ | 1-Cl—(c-propyl) |
| 880 | 2-F-3-Cl | 1-Cl—(c-propyl) |
| 881 | 2-F-4-Cl | 1-Cl—(c-propyl) |
| 882 | 2-Cl-3-F | 1-Cl—(c-propyl) |
| 883 | 2-Cl-4-F | 1-Cl—(c-propyl) |
| 884 | 2-CH$_3$ | 1-Cl—(c-propyl) |
| 885 | 3-CH$_3$ | 1-Cl—(c-propyl) |
| 886 | 4-CH$_3$ | 1-Cl—(c-propyl) |
| 887 | 4-CF$_3$ | 1-Cl—(c-propyl) |
| 888 | 2-CHF$_2$ | 1-Cl—(c-propyl) |
| 889 | 3-CHF$_2$ | 1-Cl—(c-propyl) |
| 890 | 4-CHF$_2$ | 1-Cl—(c-propyl) |
| 891 | 2-OCH$_3$ | 1-Cl—(c-propyl) |
| 892 | 4-OCH$_3$ | 1-Cl—(c-propyl) |
| 893 | 2-OCF$_3$ | 1-Cl—(c-propyl) |
| 894 | 4-OCF$_3$ | 1-Cl—(c-propyl) |
| 895 | 2-OCHF$_2$ | 1-Cl—(c-propyl) |
| 896 | 3-OCHF$_2$ | 1-Cl—(c-propyl) |
| 897 | 4-OCHF$_2$ | 1-Cl—(c-propyl) |
| 898 | 2,4-(CH$_3$)$_2$ | 1-Cl—(c-propyl) |
| 899 | 2,4,6-(CH$_3$)$_3$ | 1-Cl—(c-propyl) |
| 900 | —* | 1-CH$_3$—(c-propyl) |
| 901 | 2-Cl | 1-CH$_3$—(c-propyl) |
| 902 | 3-Cl | 1-CH$_3$—(c-propyl) |
| 903 | 4-Cl | 1-CH$_3$—(c-propyl) |
| 904 | 2-F | 1-CH$_3$—(c-propyl) |
| 905 | 3-F | 1-CH$_3$—(c-propyl) |
| 906 | 4-F | 1-CH$_3$—(c-propyl) |
| 907 | 2,4-Cl$_2$ | 1-CH$_3$—(c-propyl) |
| 908 | 2,6-Cl$_2$ | 1-CH$_3$—(c-propyl) |
| 909 | 2,4-F$_2$ | 1-CH$_3$—(c-propyl) |
| 910 | 2,6-F$_2$ | 1-CH$_3$—(c-propyl) |
| 911 | 2-F-3-Cl | 1-CH$_3$—(c-propyl) |
| 912 | 2-F-4-Cl | 1-CH$_3$—(c-propyl) |
| 913 | 2-Cl-3-F | 1-CH$_3$—(c-propyl) |
| 914 | 2-Cl-4-F | 1-CH$_3$—(c-propyl) |
| 915 | 2-CH$_3$ | 1-CH$_3$—(c-propyl) |
| 916 | 3-CH$_3$ | 1-CH$_3$—(c-propyl) |
| 917 | 4-CH$_3$ | 1-CH$_3$—(c-propyl) |
| 918 | 4-CF$_3$ | 1-CH$_3$—(c-propyl) |
| 919 | 2-CHF$_2$ | 1-CH$_3$—(c-propyl) |
| 920 | 3-CHF$_2$ | 1-CH$_3$—(c-propyl) |
| 921 | 4-CHF$_2$ | 1-CH$_3$—(c-propyl) |
| 922 | 2-OCH$_3$ | 1-CH$_3$—(c-propyl) |
| 923 | 4-OCH$_3$ | 1-CH$_3$—(c-propyl) |
| 924 | 2-OCF$_3$ | 1-CH$_3$—(c-propyl) |
| 925 | 4-OCF$_3$ | 1-CH$_3$—(c-propyl) |
| 926 | 2-OCHF$_2$ | 1-CH$_3$—(c-propyl) |
| 927 | 3-OCHF$_2$ | 1-CH$_3$—(c-propyl) |
| 928 | 4-OCHF$_2$ | 1-CH$_3$—(c-propyl) |
| 929 | 2,4-(CH$_3$)$_2$ | 1-CH$_3$—(c-propyl) |
| 930 | 2,4,6-(CH$_3$)$_3$ | 1-CH$_3$—(c-propyl) |
| 931 | —* | 1-CN—(c-propyl) |
| 932 | 2-Cl | 1-CN—(c-propyl) |
| 933 | 3-Cl | 1-CN—(c-propyl) |
| 934 | 4-Cl | 1-CN—(c-propyl) |
| 935 | 2-F | 1-CN—(c-propyl) |
| 936 | 3-F | 1-CN—(c-propyl) |
| 937 | 4-F | 1-CN—(c-propyl) |
| 938 | 2,4-Cl$_2$ | 1-CN—(c-propyl) |
| 939 | 2,6-Cl$_2$ | 1-CN—(c-propyl) |
| 940 | 2,4-F$_2$ | 1-CN—(c-propyl) |
| 941 | 2,6-F$_2$ | 1-CN—(c-propyl) |
| 942 | 2-F-3-Cl | 1-CN—(c-propyl) |
| 943 | 2-F-4-Cl | 1-CN—(c-propyl) |
| 944 | 2-Cl-3-F | 1-CN—(c-propyl) |
| 945 | 2-Cl-4-F | 1-CN—(c-propyl) |
| 946 | 2-CH$_3$ | 1-CN—(c-propyl) |

TABLE A1-continued

| No. | $R^4_m$ | $R^1$ |
|---|---|---|
| 947 | 3-CH₃ | 1-CN—(c-propyl) |
| 948 | 4-CH₃ | 1-CN—(c-propyl) |
| 949 | 4-CF₃ | 1-CN—(c-propyl) |
| 950 | 2-CHF₂ | 1-CN—(c-propyl) |
| 951 | 3-CHF₂ | 1-CN—(c-propyl) |
| 952 | 4-CHF₂ | 1-CN—(c-propyl) |
| 953 | 2-OCH₃ | 1-CN—(c-propyl) |
| 954 | 4-OCH₃ | 1-CN—(c-propyl) |
| 955 | 2-OCF₃ | 1-CN—(c-propyl) |
| 956 | 4-OCF₃ | 1-CN—(c-propyl) |
| 957 | 2-OCHF₂ | 1-CN—(c-propyl) |
| 958 | 3-OCHF₂ | 1-CN—(c-propyl) |
| 959 | 4-OCHF₂ | 1-CN—(c-propyl) |
| 960 | 2,4-(CH₃)₂ | 1-CN—(c-propyl) |
| 961 | 2,4,6-(CH₃)₃ | 1-CN—(c-propyl) |
| 962 | —* | CH₂OCH₃ |
| 963 | 2-Cl | CH₂OCH₃ |
| 964 | 3-Cl | CH₂OCH₃ |
| 965 | 4-Cl | CH₂OCH₃ |
| 966 | 2-F | CH₂OCH₃ |
| 967 | 3-F | CH₂OCH₃ |
| 968 | 4-F | CH₂OCH₃ |
| 969 | 2,4-Cl₂ | CH₂OCH₃ |
| 970 | 2,6-Cl₂ | CH₂OCH₃ |
| 971 | 2,4-F₂ | CH₂OCH₃ |
| 972 | 2,6-F₂ | CH₂OCH₃ |
| 973 | 2-F-3-Cl | CH₂OCH₃ |
| 974 | 2-F-4-Cl | CH₂OCH₃ |
| 975 | 2-Cl-3-F | CH₂OCH₃ |
| 976 | 2-Cl-4-F | CH₂OCH₃ |
| 977 | 2-CH₃ | CH₂OCH₃ |
| 978 | 3-CH₃ | CH₂OCH₃ |
| 979 | 4-CH₃ | CH₂OCH₃ |
| 980 | 4-CF₃ | CH₂OCH₃ |
| 981 | 2-CHF₂ | CH₂OCH₃ |
| 982 | 3-CHF₂ | CH₂OCH₃ |
| 983 | 4-CHF₂ | CH₂OCH₃ |
| 984 | 2-OCH₃ | CH₂OCH₃ |
| 985 | 4-OCH₃ | CH₂OCH₃ |
| 986 | 2-OCF₃ | CH₂OCH₃ |
| 987 | 4-OCF₃ | CH₂OCH₃ |
| 988 | 2-OCHF₂ | CH₂OCH₃ |
| 989 | 3-OCHF₂ | CH₂OCH₃ |
| 990 | 4-OCHF₂ | CH₂OCH₃ |
| 991 | 2,4-(CH₃)₂ | CH₂OCH₃ |
| 992 | 2,4,6-(CH₃)₃ | CH₂OCH₃ |
| 993 | —* | CH₂OCH₂CH₃ |
| 994 | 2-Cl | CH₂OCH₂CH₃ |
| 995 | 3-Cl | CH₂OCH₂CH₃ |
| 996 | 4-Cl | CH₂OCH₂CH₃ |
| 997 | 2-F | CH₂OCH₂CH₃ |
| 998 | 3-F | CH₂OCH₂CH₃ |
| 999 | 4-F | CH₂OCH₂CH₃ |
| 1000 | 2,4-Cl₂ | CH₂OCH₂CH₃ |
| 1001 | 2,6-Cl₂ | CH₂OCH₂CH₃ |
| 1002 | 2,4-F₂ | CH₂OCH₂CH₃ |
| 1003 | 2,6-F₂ | CH₂OCH₂CH₃ |
| 1004 | 2-F-3-Cl | CH₂OCH₂CH₃ |
| 1005 | 2-F-4-Cl | CH₂OCH₂CH₃ |
| 1006 | 2-Cl-3-F | CH₂OCH₂CH₃ |
| 1007 | 2-Cl-4-F | CH₂OCH₂CH₃ |
| 1008 | 2-CH₃ | CH₂OCH₂CH₃ |
| 1009 | 3-CH₃ | CH₂OCH₂CH₃ |
| 1010 | 4-CH₃ | CH₂OCH₂CH₃ |
| 1011 | 4-CF₃ | CH₂OCH₂CH₃ |
| 1012 | 2-CHF₂ | CH₂OCH₂CH₃ |
| 1013 | 3-CHF₂ | CH₂OCH₂CH₃ |
| 1014 | 4-CHF₂ | CH₂OCH₂CH₃ |
| 1015 | 2-OCH₃ | CH₂OCH₂CH₃ |
| 1016 | 4-OCH₃ | CH₂OCH₂CH₃ |
| 1017 | 2-OCF₃ | CH₂OCH₂CH₃ |
| 1018 | 4-OCF₃ | CH₂OCH₂CH₃ |
| 1019 | 2-OCHF₂ | CH₂OCH₂CH₃ |
| 1020 | 3-OCHF₂ | CH₂OCH₂CH₃ |
| 1021 | 4-OCHF₂ | CH₂OCH₂CH₃ |
| 1022 | 2,4-(CH₃)₂ | CH₂OCH₂CH₃ |
| 1023 | 2,4,6-(CH₃)₃ | CH₂OCH₂CH₃ |
| 1024 | —* | CH(CH₃)OCH₃ |
| 1025 | 2-Cl | CH(CH₃)OCH₃ |
| 1026 | 3-Cl | CH(CH₃)OCH₃ |
| 1027 | 4-Cl | CH(CH₃)OCH₃ |
| 1028 | 2-F | CH(CH₃)OCH₃ |
| 1029 | 3-F | CH(CH₃)OCH₃ |
| 1030 | 4-F | CH(CH₃)OCH₃ |
| 1031 | 2,4-Cl₂ | CH(CH₃)OCH₃ |
| 1032 | 2,6-Cl₂ | CH(CH₃)OCH₃ |
| 1033 | 2,4-F₂ | CH(CH₃)OCH₃ |
| 1034 | 2,6-F₂ | CH(CH₃)OCH₃ |
| 1035 | 2-F-3-Cl | CH(CH₃)OCH₃ |
| 1036 | 2-F-4-Cl | CH(CH₃)OCH₃ |
| 1037 | 2-Cl-3-F | CH(CH₃)OCH₃ |
| 1038 | 2-Cl-4-F | CH(CH₃)OCH₃ |
| 1039 | 2-CH₃ | CH(CH₃)OCH₃ |
| 1040 | 3-CH₃ | CH(CH₃)OCH₃ |
| 1041 | 4-CH₃ | CH(CH₃)OCH₃ |
| 1042 | 4-CF₃ | CH(CH₃)OCH₃ |
| 1043 | 2-CHF₂ | CH(CH₃)OCH₃ |
| 1044 | 3-CHF₂ | CH(CH₃)OCH₃ |
| 1045 | 4-CHF₂ | CH(CH₃)OCH₃ |
| 1046 | 2-OCH₃ | CH(CH₃)OCH₃ |
| 1047 | 4-OCH₃ | CH(CH₃)OCH₃ |
| 1048 | 2-OCF₃ | CH(CH₃)OCH₃ |
| 1049 | 4-OCF₃ | CH(CH₃)OCH₃ |
| 1050 | 2-OCHF₂ | CH(CH₃)OCH₃ |
| 1051 | 3-OCHF₂ | CH(CH₃)OCH₃ |
| 1052 | 4-OCHF₂ | CH(CH₃)OCH₃ |
| 1053 | 2,4-(CH₃)₂ | CH(CH₃)OCH₃ |
| 1054 | 2,4,6-(CH₃)₃ | CH(CH₃)OCH₃ |
| 1055 | —* | CH(CH₃)OCH₂CH₃ |
| 1056 | 2-Cl | CH(CH₃)OCH₂CH₃ |
| 1057 | 3-Cl | CH(CH₃)OCH₂CH₃ |
| 1058 | 4-Cl | CH(CH₃)OCH₂CH₃ |
| 1059 | 2-F | CH(CH₃)OCH₂CH₃ |
| 1060 | 3-F | CH(CH₃)OCH₂CH₃ |
| 1061 | 4-F | CH(CH₃)OCH₂CH₃ |
| 1062 | 2,4-Cl₂ | CH(CH₃)OCH₂CH₃ |
| 1063 | 2,6-Cl₂ | CH(CH₃)OCH₂CH₃ |
| 1064 | 2,4-F₂ | CH(CH₃)OCH₂CH₃ |
| 1065 | 2,6-F₂ | CH(CH₃)OCH₂CH₃ |
| 1066 | 2-F-3-Cl | CH(CH₃)OCH₂CH₃ |
| 1067 | 2-F-4-Cl | CH(CH₃)OCH₂CH₃ |
| 1068 | 2-Cl-3-F | CH(CH₃)OCH₂CH₃ |
| 1069 | 2-Cl-4-F | CH(CH₃)OCH₂CH₃ |
| 1070 | 2-CH₃ | CH(CH₃)OCH₂CH₃ |
| 1071 | 3-CH₃ | CH(CH₃)OCH₂CH₃ |
| 1072 | 4-CH₃ | CH(CH₃)OCH₂CH₃ |
| 1073 | 4-CF₃ | CH(CH₃)OCH₂CH₃ |
| 1074 | 2-CHF₂ | CH(CH₃)OCH₂CH₃ |
| 1075 | 3-CHF₂ | CH(CH₃)OCH₂CH₃ |
| 1076 | 4-CHF₂ | CH(CH₃)OCH₂CH₃ |
| 1077 | 2-OCH₃ | CH(CH₃)OCH₂CH₃ |
| 1078 | 4-OCH₃ | CH(CH₃)OCH₂CH₃ |
| 1079 | 2-OCF₃ | CH(CH₃)OCH₂CH₃ |
| 1080 | 4-OCF₃ | CH(CH₃)OCH₂CH₃ |
| 1081 | 2-OCHF₂ | CH(CH₃)OCH₂CH₃ |
| 1082 | 3-OCHF₂ | CH(CH₃)OCH₂CH₃ |
| 1083 | 4-OCHF₂ | CH(CH₃)OCH₂CH₃ |
| 1084 | 2,4-(CH₃)₂ | CH(CH₃)OCH₂CH₃ |
| 1085 | 2,4,6-(CH₃)₃ | CH(CH₃)OCH₂CH₃ |

*this means that m = 0;
c-propyl" stands for cyclopropyl

The compounds I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

Thus, the present invention also relates to a method for combating phytopathogenic fungi, comprising: treating the fungi or the materials, plants, the soil or seeds to be protected against fungal attack with an effective amount of at least one compound of formula I as defined herein.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or goose-berries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grape-fruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e.g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyl-phenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins.

Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The compounds I and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphano-myces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthi-anum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chiamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g.

*E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grain-staining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans* late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. scierotiorum*); *Septoria* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalia*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6$^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; dimethyl sulfoxide (DMSO); ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble Concentrates (SL, LS)

10-60 wt % of a compound I and 5-15 wt % wetting agent (e.g. alcohol alkoxylates) are dissolved in water and/or in a water-soluble solvent (e.g. alcohols) up to 100 wt %. The active substance dissolves upon dilution with water.
ii) Dispersible Concentrates (DC)

5-25 wt % of a compound I and 1-10 wt % dispersant (e.g. polyvinylpyrrolidone) are dissolved in up to 100 wt % organic solvent (e.g. cyclohexanone). Dilution with water gives a dispersion.
iii) Emulsifiable Concentrates (EC)

15-70 wt % of a compound I and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.
iv) Emulsions (EW, EO, ES)

5-40 wt % of a compound I and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.
v) Suspensions (SC, OD, FS)

In an agitated ball mill, 20-60 wt % of a compound I are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.
vi) Water-Dispersible Granules and Water-Soluble Granules (WG, SG)

50-80 wt % of a compound I are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.
vii) Water-Dispersible Powders and Water-Soluble Powders (WP, SP, WS)

50-80 wt % of a compound I are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.
viii) Gel (GW, GF)

In an agitated ball mill, 5-25 wt % of a compound I are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.
iv) Microemulsion (ME)

5-20 wt % of a compound I are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.
iv) Microcapsules (CS)

An oil phase comprising 5-50 wt % of a compound I, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4, 4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.
ix) Dustable Powders (DP, DS)

1-10 wt % of a compound I are ground finely and mixed intimately with up to 100 wt % solid carrier, e.g. finely divided kaolin.

x) Granules (GR, FG)

0.5-30 wt % of a compound I is ground finely and associated with up to 100 wt % solid carrier (e.g. silicate). Granulation is achieved by extrusion, spray-drying or the fluidized bed.

xi) Ultra-Low Volume Liquids (UL)

1-50 wt % of a compound I are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Water-soluble concentrates (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying or treating compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds I can be used, is intended to illustrate the possible combinations but does not limit them:

A) Respiration Inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

inhibitors of complex II (e.g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, 3-(difluoromethyl)-1-methyl-N-(1,1,3-trimethylindan-4-yl) pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluorometh-yl)-1,5-dimethyl-N-(1,1,3-trimethylindan-4-yl)pyrazole-4-carboxamide, 3-(difluoro-methyl)-1,5-dimethyl-N-(1, 1,3-trimethylindan-4-yl)pyrazole-4-carboxamide, 1,3,5-tri-methyl-N-(1,1,3-trimethylindan-4-yl)pyrazole-4-carboxamide;
other respiration inhibitors (e.g. complex I, uncouplers): diflumetorim, (5,8-difluoro-quinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organo-metal compounds: fentin salts, such as fentin-acetate, fentin chloride or fentin hydroxide; ametoctradin; and silthiofam;

B) Sterol Biosynthesis Inhibitors (SBI Fungicides)
C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; -[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol, imidazoles: imazalil, pefurazoate, prochloraz, triflumizol; pyrimidines, pyridines and piperazines: fenarimol, nuarimol, pyrifenox, triforine;
Delta14-reductase inhibitors: aldimorph, dodemorph, dodemorph-acetate, fenpropimorph, tridemorph, fenpropidin, piperalin, spiroxamine;
Inhibitors of 3-keto reductase: fenhexamid;

C) Nucleic Acid Synthesis Inhibitors
phenylamides or acyl amino acid fungicides: benalaxyl, benalaxyl-M, kiralaxyl, metalaxyl, metalaxyl-M (mefenoxam), ofurace, oxadixyl;
others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenyl-methoxy)pyrimidin-4-amine;

D) Inhibitors of Cell Division and Cytoskeleton
tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine
other cell division inhibitors: diethofencarb, ethaboxam, pencycuron, fluopicolide, zoxamide, metrafenone, pyriofenone;

E) Inhibitors of Amino Acid and Protein Synthesis
methionine synthesis inhibitors (anilino-pyrimidines): cyprodinil, mepanipyrim, pyrimethanil;
protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors
MAP/histidine kinase inhibitors: fluoroimid, iprodione, procymidone, vinclozolin, fenpiclonil, fludioxonil;
G protein inhibitors: quinoxyfen;

G) Lipid and Membrane Synthesis Inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
compounds affecting cell membrane permeability and fatty acides: propamocarb, propamocarb-hydrochlorid;
fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon; 2,6-dimethyl-1H,5H-[1,4]dithiino[2,3-c:5,6-c']dipyrrole-1,3,5,7(2H,6H)-tetraone;

I) Cell Wall Synthesis Inhibitors
inhibitors of glucan synthesis: validamycin, polyoxin B;
melanin synthesis inhibitors: pyroquilon, tricyclazole, carpropamid, dicyclomet, fenoxanil;

J) Plant Defence Inducers
acibenzolar-S-methyl, probenazole, isotianil, tiadinil, prohexadione-calcium; phosphonates: fosetyl, fosetyl-aluminum, phosphorous acid and its salts;

K) Unknown Mode of Action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropyl-methoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, 1V-Methyl-2-{1-[(5-methyl-3-trifluoromethyl-1H-pyrazol-1-yl)-acetyl]-piperidin-4-yl}-M[(1R)-1,2,3,4-tetrahydro-naphthalen-1-yl]-4-thiazolecarboxamide, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

L) Antifungal Biocontrol Agents, Plant Bioactivators:*Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and *TRICHODERMA* 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB BioInnovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth Regulators abscisic acid, amidochlor, ancymidol, 6-benzylaminopurine, brassinolide, butralin, chlormequat (chlormequat chloride), choline chloride, cyclanilide, daminozide, dike-gulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, metha-benzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera*

*monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etox-azole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

The present invention furthermore relates to agrochemical compositions comprising a mixture of at least one compound I (component 1) and at least one further active substance useful for plant protection, e.g. selected from the groups A) to O) (component 2), in particular one further fungicide, e.g. one or more fungicide from the groups A) to L), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to L), as described above, is more efficient than combating those fungi with individual compounds I or individual fungicides from groups A) to L). By applying compounds I together with at least one active substance from groups A) to O) a synergistic effect can be obtained, i.e. more then simple addition of the individual effects is obtained (synergistic mixtures).

This can be obtained by applying the compounds I and at least one further active substance simultaneously, either jointly (e.g. as tank-mix) or seperately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I (component 1) and one further active substance (component 2), e.g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I (component 1) and a first further active substance (component 2) and a second further active substance (component 3), e.g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to mixtures comprising a compound I (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound of formula I (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound of formula I (component 1) and at least one active substance selected from group C) (component 2) and particularly selected from metalaxyl, (metalaxyl-M) mefenoxam, ofurace.

Preference is given to mixtures comprising a compound of formula I (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I (component 1) and at least one active substance selected from group E) (component 2) and particularly selected from cyprodinil, mepanipyrim, pyrimethanil.

Preference is also given to mixtures comprising a compound I (component 1) and at least one active substance selected from group F) (component 2) and particularly selected from iprodione, fludioxonil, vinclozolin, quinoxyfen.

Preference is also given to mixtures comprising a compound I (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I (component 1) and at least one active substance selected from group I) (component 2) and particularly selected from carpropamid and fenoxanil.

Preference is also given to mixtures comprising a compound I (component 1) and at least one active substance selected from group J) (component 2) and particularly selected from acibenzolar-S-methyl, probenazole, tiadinil, fosetyl, fosetyl-aluminium, $H_3PO_3$ and salts thereof.

Preference is also given to mixtures comprising a compound I (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Preference is also given to mixtures comprising a compound I (component 1) and at least one active substance selected from group L) (component 2) and particularly selected from *Bacillus subtilis* strain NRRL No. B-21661, *Bacillus pumilus* strain NRRL No. B-30087 and *Ulocladium oudemansii*.

Accordingly, the present invention furthermore relates to compositions comprising one compound I (component 1) and one further active substance (component 2), which further active substance is selected from the column "Component 2" of the lines B-1 to B-360 of Table B.

A further embodiment relates to the compositions B-1 to B-372 listed in Table B, where a row of Table B corresponds in each case to a fungicidal composition comprising one of the in the present specification individualized compounds of formula I (component 1) and the respective further active substance from groups A) to O) (component 2) stated in the row in question. Preferably, the compositions described comprise the active substances in synergistically effective amounts.

TABLE B

Composition comprising one indivivalized compound I and one further active substance from groups A) to O)

| Mixture | Component 1 | Component 2 |
|---|---|---|
| B-1 | one individualized compound I | Azoxystrobin |
| B-2 | one individualized compound I | Coumethoxystrobin |
| B-3 | one individualized compound I | Coumoxystrobin |
| B-4 | one individualized compound I | Dimoxystrobin |
| B-5 | one individualized compound I | Enestroburin |
| B-6 | one individualized compound I | Fenaminstrobin |
| B-7 | one individualized compound I | Fenoxystrobin/Flufenoxystrobin |
| B-8 | one individualized compound I | Fluoxastrobin |
| B-9 | one individualized compound I | Kresoxim-methyl |
| B-10 | one individualized compound I | Metominostrobin |
| B-11 | one individualized compound I | Orysastrobin |
| B-12 | one individualized compound I | Picoxystrobin |
| B-13 | one individualized compound I | Pyraclostrobin |
| B-14 | one individualized compound I | Pyrametostrobin |
| B-15 | one individualized compound I | Pyraoxystrobin |
| B-16 | one individualized compound I | Pyribencarb |
| B-17 | one individualized compound I | Trifloxystrobin |
| B-18 | one individualized compound I | Triclopyricarb/Chlorodincarb |
| B-19 | one individualized compound I | 2-[2-(2,5-dimethyl-phenoxymethyl)-phenyl]-3-methoxy-acrylic acid methyl ester |
| B-20 | one individualized compound I | 2-(2-(3-(2,6-dichlorophenyl)-1-methyl-allylideneaminooxymethyl)-phenyl)-2-methoxyimino-N-methyl-acetamide |
| B-21 | one individualized compound I | Benalaxyl |
| B-22 | one individualized compound I | Benalaxyl-M |
| B-23 | one individualized compound I | Benodanil |
| B-24 | one individualized compound I | Bixafen |
| B-25 | one individualized compound I | Boscalid |
| B-26 | one individualized compound I | Carboxin |
| B-27 | one individualized compound I | Fenfuram |
| B-28 | one individualized compound I | Fenhexamid |
| B-29 | one individualized compound I | Flutolanil |
| B-30 | one individualized compound I | Fluxapyroxad |
| B-31 | one individualized compound I | Furametpyr |
| B-32 | one individualized compound I | Isopyrazam |
| B-33 | one individualized compound I | Isotianil |
| B-34 | one individualized compound I | Kiralaxyl |
| B-35 | one individualized compound I | Mepronil |
| B-36 | one individualized compound I | Metalaxyl |
| B-37 | one individualized compound I | Metalaxyl-M |
| B-38 | one individualized compound I | Ofurace |
| B-39 | one individualized compound I | Oxadixyl |
| B-40 | one individualized compound I | Oxycarboxin |
| B-41 | one individualized compound I | Penflufen |
| B-42 | one individualized compound I | Penthiopyrad |
| B-43 | one individualized compound I | Sedaxane |
| B-44 | one individualized compound I | Tecloftalam |

TABLE B-continued

Composition comprising one indivivalized compound I and one further active substance from groups A) to O)

| Mixture | Component 1 | Component 2 |
|---|---|---|
| B-45 | one individualized compound I | Thifluzamide |
| B-46 | one individualized compound I | Tiadinil |
| B-47 | one individualized compound I | 2-Amino-4-methyl-thiazole-5-carboxylic acid anilide |
| B-48 | one individualized compound I | N-(4'-trifluoromethylthiobiphenyl-2-yl)-3-difluoromethyl-1-methyl-1H-pyrazole-4-carboxamide |
| B-49 | one individualized compound I | N-(2-(1,3,3-trimethyl-butyl)-phenyl)-1,3-dimethyl-5-fluoro-1H-pyrazole-4-carboxamide |
| B-50 | one individualized compound I | N-[9-(dichloromethylene)-1,2,3,4-tetrahydro-1,4-methanonaphthalen-5-yl]-3-(difluoromethyl)-1-methyl-1H-pyrazole-4-carboxamide |
| B-51 | one individualized compound I | Dimethomorph |
| B-52 | one individualized compound I | Flumorph |
| B-53 | one individualized compound I | Pyrimorph |
| B-54 | one individualized compound I | Flumetover |
| B-55 | one individualized compound I | Fluopicolide |
| B-56 | one individualized compound I | Fluopyram |
| B-57 | one individualized compound I | Zoxamide |
| B-58 | one individualized compound I | Carpropamid |
| B-59 | one individualized compound I | Diclocymet |
| B-60 | one individualized compound I | Mandipropamid |
| B-61 | one individualized compound I | Oxytetracyclin |
| B-62 | one individualized compound I | Silthiofam |
| B-63 | one individualized compound I | N-(6-methoxy-pyridin-3-yl) cyclopropanecarboxylic acid amide |
| B-64 | one individualized compound I | Azaconazole |
| B-65 | one individualized compound I | Bitertanol |
| B-66 | one individualized compound I | Bromuconazole |
| B-67 | one individualized compound I | Cyproconazole |
| B-68 | one individualized compound I | Difenoconazole |
| B-69 | one individualized compound I | Diniconazole |
| B-70 | one individualized compound I | Diniconazole-M |
| B-71 | one individualized compound I | Epoxiconazole |
| B-72 | one individualized compound I | Fenbuconazole |
| B-73 | one individualized compound I | Fluquinconazole |
| B-74 | one individualized compound I | Flusilazole |
| B-75 | one individualized compound I | Flutriafol |
| B-76 | one individualized compound I | Hexaconazol |
| B-77 | one individualized compound I | Imibenconazole |
| B-78 | one individualized compound I | Ipconazole |
| B-79 | one individualized compound I | Metconazole |
| B-80 | one individualized compound I | Myclobutanil |
| B-81 | one individualized compound I | Oxpoconazol |
| B-82 | one individualized compound I | Paclobutrazol |
| B-83 | one individualized compound I | Penconazole |
| B-84 | one individualized compound I | Propiconazole |
| B-85 | one individualized compound I | Prothioconazole |
| B-86 | one individualized compound I | Simeconazole |
| B-87 | one individualized compound I | Tebuconazole |
| B-88 | one individualized compound I | Tetraconazole |
| B-89 | one individualized compound I | Triadimefon |
| B-90 | one individualized compound I | Triadimenol |
| B-91 | one individualized compound I | Triticonazole |
| B-92 | one individualized compound I | Uniconazole |
| B-93 | one individualized compound I | Cyazofamid |
| B-94 | one individualized compound I | Imazalil |
| B-95 | one individualized compound I | Imazalil-sulfate |
| B-96 | one individualized compound I | Pefurazoate |
| B-97 | one individualized compound I | Prochloraz |
| B-98 | one individualized compound I | Triflumizole |
| B-99 | one individualized compound I | Benomyl |
| B-100 | one individualized compound I | Carbendazim |
| B-101 | one individualized compound I | Fuberidazole |
| B-102 | one individualized compound I | Thiabendazole |
| B-103 | one individualized compound I | Ethaboxam |
| B-104 | one individualized compound I | Etridiazole |
| B-105 | one individualized compound I | Hymexazole |
| B-106 | one individualized compound I | 2-(4-Chloro-phenyl)-N-[4-(3,4-dimethoxy-phenyl)-isoxazol-5-yl]-2-prop-2-yn-yloxy-acetamide |
| B-107 | one individualized compound I | Fluazinam |
| B-108 | one individualized compound I | Pyrifenox |
| B-109 | one individualized compound I | 3-[5-(4-Chloro-phenyl)-2,3-dimethyl-isoxazolidin-3-yl]-pyridine (Pyrisoxazole) |
| B-110 | one individualized compound I | 3-[5-(4-Methyl-phenyl)-2,3-dimethyl-isoxazolidin-3-yl]-pyridine |
| B-111 | one individualized compound I | Bupirimate |
| B-112 | one individualized compound I | Cyprodinil |
| B-113 | one individualized compound I | 5-Fluorocytosine |
| B-114 | one individualized compound I | 5-Fluoro-2-(p-tolylmethoxy)pyrimidin-4-amine |
| B-115 | one individualized compound I | 5-Fluoro-2-(4-fluorophenylmethoxy)-pyrimidin-4-amine |
| B-116 | one individualized compound I | Diflumetorim |
| B-117 | one individualized compound I | (5,8-Difluoroquinazolin-4-yl)-{2-[2-fluoro-4-(4-trifluoromethylpyridin-2-yloxy)-phenyl]-ethyl}-amine |
| B-118 | one individualized compound I | Fenarimol |
| B-119 | one individualized compound I | Ferimzone |
| B-120 | one individualized compound I | Mepanipyrim |
| B-121 | one individualized compound I | Nitrapyrin |
| B-122 | one individualized compound I | Nuarimol |
| B-123 | one individualized compound I | Pyrimethanil |
| B-124 | one individualized compound I | Triforine |
| B-125 | one individualized compound I | Fenpiclonil |
| B-126 | one individualized compound I | Fludioxonil |
| B-127 | one individualized compound I | Aldimorph |
| B-128 | one individualized compound I | Dodemorph |
| B-129 | one individualized compound I | Dodemorph-acetate |
| B-130 | one individualized compound I | Fenpropimorph |
| B-131 | one individualized compound I | Tridemorph |
| B-132 | one individualized compound I | Fenpropidin |
| B-133 | one individualized compound I | Fluoroimid |
| B-134 | one individualized compound I | Iprodione |
| B-135 | one individualized compound I | Procymidone |
| B-136 | one individualized compound I | Vinclozolin |
| B-137 | one individualized compound I | Famoxadone |
| B-138 | one individualized compound I | Fenamidone |
| B-139 | one individualized compound I | Flutianil |
| B-140 | one individualized compound I | Octhilinone |
| B-141 | one individualized compound I | Probenazole |
| B-142 | one individualized compound I | Fenpyrazamine |
| B-143 | one individualized compound I | Acibenzolar-S-methyl |
| B-144 | one individualized compound I | Ametoctradin |
| B-145 | one individualized compound I | Amisulbrom |
| B-146 | one individualized compound I | [(3S,6S,7R,8R)-8-benzyl-3-[(3-isobutyryloxymethoxy-4-methoxypyridine-2-carbonyl)amino]-6-methyl-4,9-dioxo-[1,5]dioxonan-7-yl]2-methylpropanoate |
| B-147 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate |
| B-148 | one individualized compound I | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate |
| B-149 | one individualized compound I | [(3S,6S,7R,8R)-8-benzyl-3-[(3-isobutoxycarbonyloxy-4-methoxy-pyridine- |

TABLE B-continued

Composition comprising one indivivalized compound I and one further active substance from groups A) to O)

| Mixture | Component 1 | Component 2 |
|---|---|---|
| | | 2-carbonyl)amino]-6-methyl-4,9-dioxo-1,5-dioxonan-7-yl]2-methylpropanoate |
| B-150 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methyl-propanoate |
| B-151 | one individualized compound I | Anilazin |
| B-152 | one individualized compound I | Blasticidin-S |
| B-153 | one individualized compound I | Captafol |
| B-154 | one individualized compound I | Captan |
| B-155 | one individualized compound I | Chinomethionat |
| B-156 | one individualized compound I | Dazomet |
| B-157 | one individualized compound I | Debacarb |
| B-158 | one individualized compound I | Diclomezine |
| B-159 | one individualized compound I | Difenzoquat, |
| B-160 | one individualized compound I | Difenzoquat-methylsulfate |
| B-161 | one individualized compound I | Fenoxanil |
| B-162 | one individualized compound I | Folpet |
| B-163 | one individualized compound I | Oxolinsaure |
| B-164 | one individualized compound I | Piperalin |
| B-165 | one individualized compound I | Proquinazid |
| B-166 | one individualized compound I | Pyroquilon |
| B-167 | one individualized compound I | Quinoxyfen |
| B-168 | one individualized compound I | Triazoxid |
| B-169 | one individualized compound I | Tricyclazole |
| B-170 | one individualized compound I | 2-Butoxy-6-iodo-3-propyl-chromen-4-one |
| B-171 | one individualized compound I | 5-Chloro-1-(4,6-dimethoxy-pyrimidin-2-yl)-2-methyl-1H-benzoimidazole |
| B-172 | one individualized compound I | 5-Chloro-7-(4-methyl-piperidin-1-yl)-6-(2,4,6-trifluoro-phenyl)-[1,2,4]triazolo[1,5-a]pyrimidine |
| B-173 | one individualized compound I | Ferbam |
| B-174 | one individualized compound I | Mancozeb |
| B-175 | one individualized compound I | Maneb |
| B-176 | one individualized compound I | Metam |
| B-177 | one individualized compound I | Methasulphocarb |
| B-178 | one individualized compound I | Metiram |
| B-179 | one individualized compound I | Propineb |
| B-180 | one individualized compound I | Thiram |
| B-181 | one individualized compound I | Zineb |
| B-182 | one individualized compound I | Ziram |
| B-183 | one individualized compound I | Diethofencarb |
| B-184 | one individualized compound I | Benthiavalicarb |
| B-185 | one individualized compound I | Iprovalicarb |
| B-186 | one individualized compound I | Propamocarb |
| B-187 | one individualized compound I | Propamocarb hydrochlorid |
| B-188 | one individualized compound I | Valifenalate |
| B-189 | one individualized compound I | N-(1-(1-(4-cyanophenyl)ethanesulfonyl)-but-2-yl) carbamic acid-(4-fluoro-phenyl) ester |
| B-190 | one individualized compound I | Dodine |
| B-191 | one individualized compound I | Dodine free base |
| B-192 | one individualized compound I | Guazatine |
| B-193 | one individualized compound I | Guazatine-acetate |
| B-194 | one individualized compound I | Iminoctadine |
| B-195 | one individualized compound I | Iminoctadine-triacetate |
| B-196 | one individualized compound I | Iminoctadine-tris(albesilate) |
| B-197 | one individualized compound I | Kasugamycin |
| B-198 | one individualized compound I | Kasugamycin-hydrochloride-hydrate |
| B-199 | one individualized compound I | Polyoxine |
| B-200 | one individualized compound I | Streptomycin |
| B-201 | one individualized compound I | Validamycin A |
| B-202 | one individualized compound I | Binapacryl |
| B-203 | one individualized compound I | Dicloran |
| B-204 | one individualized compound I | Dinobuton |
| B-205 | one individualized compound I | Dinocap |
| B-206 | one individualized compound I | Nitrothal-isopropyl |
| B-207 | one individualized compound I | Tecnazen |
| B-208 | one individualized compound I | Fentin salts |
| B-209 | one individualized compound I | Dithianon |
| B-210 | one individualized compound I | Isoprothiolane |
| B-211 | one individualized compound I | Edifenphos |
| B-212 | one individualized compound I | Fosetyl, Fosetyl-aluminium |
| B-213 | one individualized compound I | Iprobenfos |
| B-214 | one individualized compound I | Phosphorous acid ($H_3PO_3$) and derivatives |
| B-215 | one individualized compound I | Pyrazophos |
| B-216 | one individualized compound I | Tolclofos-methyl |
| B-217 | one individualized compound I | Chlorothalonil |
| B-218 | one individualized compound I | Dichlofluanid |
| B-219 | one individualized compound I | Dichlorophen |
| B-220 | one individualized compound I | Flusulfamide |
| B-221 | one individualized compound I | Hexachlorbenzene |
| B-222 | one individualized compound I | Pencycuron |
| B-223 | one individualized compound I | Pentachlorophenol and salts |
| B-224 | one individualized compound I | Phthalide |
| B-225 | one individualized compound I | Quintozene |
| B-226 | one individualized compound I | Thiophanate Methyl |
| B-227 | one individualized compound I | Tolylfluanid |
| B-228 | one individualized compound I | N-(4-chloro-2-nitro-phenyl)-N-ethyl-4-methyl-benzenesulfonamide |
| B-229 | one individualized compound I | Bordeaux mixture |
| B-230 | one individualized compound I | Copper acetate |
| B-231 | one individualized compound I | Copper hydroxide |
| B-232 | one individualized compound I | Copper oxychloride |
| B-233 | one individualized compound I | basic Copper sulfate |
| B-234 | one individualized compound I | Sulfur |
| B-235 | one individualized compound I | Biphenyl |
| B-236 | one individualized compound I | Bronopol |
| B-237 | one individualized compound I | Cyflufenamid |
| B-238 | one individualized compound I | Cymoxanil |
| B-239 | one individualized compound I | Diphenylamin |
| B-240 | one individualized compound I | Metrafenone |
| B-241 | one individualized compound I | Pyriofenone |
| B-242 | one individualized compound I | Mildiomycin |
| B-243 | one individualized compound I | Oxin-copper |
| B-244 | one individualized compound I | Prohexadione calcium |
| B-245 | one individualized compound I | Spiroxamine |
| B-246 | one individualized compound I | Tebufloquin |
| B-247 | one individualized compound I | Tolylfluanid |
| B-248 | one individualized compound I | N-(Cyclopropylmethoxyimino-(6-difluoromethoxy-2,3-difluoro-phenyl)-methyl)-2-phenyl acetamide |
| B-249 | one individualized compound I | N'-(4-(4-chloro-3-trifluoromethyl-phenoxy)-2,5-dimethyl-phenyl)-N-ethyl-N-methyl formamidine |
| B-250 | one individualized compound I | N'-(4-(4-fluoro-3-trifluoromethyl-phenoxy)-2,5-dimethyl-phenyl)-N-ethyl-N-methyl formamidine |
| B-251 | one individualized compound I | N'-(2-methyl-5-trifluoromethyl-4-(3-trimethylsilanyl-propoxy)-phenyl)-N-ethyl-N-methyl formamidine |
| B-252 | one individualized compound I | N'-(5-difluoromethyl-2-methyl-4-(3-trimethylsilanyl-propoxy)-phenyl)-N-ethyl-N-methyl formamidine |
| B-253 | one individualized compound I | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-254 | one individualized compound I | 2-{1-[2-(5-Methyl-3-trifluoromethyl-pyrazole-1- |

TABLE B-continued

Composition comprising one indivivalized compound I and one further active substance from groups A) to O)

| Mixture | Component 1 | Component 2 |
|---|---|---|
| | | yl)-acetyl]-piperidin-4-yl}-thiazole-4-carboxylic acid methyl-(R)-1,2,3,4-tetrahydro-naphthalen-1-yl-amide |
| B-255 | one individualized compound I | 1-[4-[4-[5-(2,6-difluorophenyl)-4,5-dihydro-3-isoxazolyl]-2-thiazolyl]-1-pipendinyl]-2-[5-methyl-3-(trifluoromethyl)-1H-pyrazol-1-yl]ethanone |
| B-256 | one individualized compound I | Methoxy-acetic acid 6-tert-butyl-8-fluoro-2,3-dimethyl-quinolin-4-yl ester |
| B-257 | one individualized compound I | N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide |
| B-258 | one individualized compound I | *Bacillus subtilis* NRRL No. B-21661 |
| B-259 | one individualized compound I | *Bacillus pumilus* NRRL No. B-30087 |
| B-260 | one individualized compound I | *Ulocladium oudemansii* |
| B-261 | one individualized compound I | Carbaryl |
| B-262 | one individualized compound I | Carbofuran |
| B-263 | one individualized compound I | Carbosulfan |
| B-264 | one individualized compound I | Methomylthiodicarb |
| B-265 | one individualized compound I | Bifenthrin |
| B-266 | one individualized compound I | Cyfluthrin |
| B-267 | one individualized compound I | Cypermethrin |
| B-268 | one individualized compound I | alpha-Cypermethrin |
| B-269 | one individualized compound I | zeta-Cypermethrin |
| B-270 | one individualized compound I | Deltamethrin |
| B-271 | one individualized compound I | Esfenvalerate |
| B-272 | one individualized compound I | Lambda-cyhalothrin |
| B-273 | one individualized compound I | Permethrin |
| B-274 | one individualized compound I | Tefluthrin |
| B-275 | one individualized compound I | Diflubenzuron |
| B-276 | one individualized compound I | Flufenoxuron |
| B-277 | one individualized compound I | Lufenuron |
| B-278 | one individualized compound I | Teflubenzuron |
| B-279 | one individualized compound I | Spirotetramate |
| B-280 | one individualized compound I | Clothianidin |
| B-281 | one individualized compound I | Dinotefuran |
| B-282 | one individualized compound I | midacloprid |
| B-283 | one individualized compound I | Thiamethoxam |
| B-284 | one individualized compound I | Acetamiprid |
| B-285 | one individualized compound I | Thiacloprid |
| B-286 | one individualized compound I | Endosulfan |
| B-287 | one individualized compound I | Fipronil |
| B-288 | one individualized compound I | Abamectin |
| B-289 | one individualized compound I | Emamectin |
| B-290 | one individualized compound I | Spinosad |
| B-291 | one individualized compound I | Spinetoram |
| B-292 | one individualized compound I | Hydramethylnon |
| B-293 | one individualized compound I | Chlorfenapyr |
| B-294 | one individualized compound I | Fenbutatin oxide |
| B-295 | one individualized compound I | Indoxacarb |
| B-296 | one individualized compound I | Metaflumizone |
| B-297 | one individualized compound I | Flonicamid |
| B-298 | one individualized compound I | Lubendiamide |
| B-299 | one individualized compound I | Chlorantraniliprole |
| B-300 | one individualized compound I | Cyazypyr (HGW86) |
| B-301 | one individualized compound I | Cyflumetofen |
| B-302 | one individualized compound I | Acetochlor |
| B-303 | one individualized compound I | Dimethenamid |
| B-304 | one individualized compound I | metolachlor |
| B-305 | one individualized compound I | Metazachlor |
| B-306 | one individualized compound I | Glyphosate |
| B-307 | one individualized compound I | Glufosinate |
| B-308 | one individualized compound I | Sulfosate |
| B-309 | one individualized compound I | Clodinafop |
| B-310 | one individualized compound I | Fenoxaprop |
| B-311 | one individualized compound I | Fluazifop |
| B-312 | one individualized compound I | Haloxyfop |
| B-313 | one individualized compound I | Paraquat |
| B-314 | one individualized compound I | Phenmedipham |
| B-315 | one individualized compound I | Clethodim |
| B-316 | one individualized compound I | Cycloxydim |
| B-317 | one individualized compound I | Profoxydim |
| B-318 | one individualized compound I | Sethoxydim |
| B-319 | one individualized compound I | Tepraloxydim |
| B-320 | one individualized compound I | Pendimethalin |
| B-321 | one individualized compound I | Prodiamine |
| B-322 | one individualized compound I | Trifluralin |
| B-323 | one individualized compound I | Acifluorfen |
| B-324 | one individualized compound I | Bromoxynil |
| B-325 | one individualized compound I | Imazamethabenz |
| B-326 | one individualized compound I | Imazamox |
| B-327 | one individualized compound I | Imazapic |
| B-328 | one individualized compound I | Imazapyr |
| B-329 | one individualized compound I | Imazaquin |
| B-330 | one individualized compound I | Imazethapyr |
| B-331 | one individualized compound I | 2,4-Dichlorophenoxyacetic acid (2,4-D) |
| B-332 | one individualized compound I | Chloridazon |
| B-333 | one individualized compound I | Clopyralid |
| B-334 | one individualized compound I | Fluroxypyr |
| B-335 | one individualized compound I | Picloram |
| B-336 | one individualized compound I | Picolinafen |
| B-337 | one individualized compound I | Bensulfuron |
| B-338 | one individualized compound I | Chlorimuron-ethyl |
| B-339 | one individualized compound I | Cyclosulfamuron |
| B-340 | one individualized compound I | Iodosulfuron |
| B-341 | one individualized compound I | Mesosulfuron |
| B-342 | one individualized compound I | Metsulfuron-methyl |
| B-343 | one individualized compound I | Nicosulfuron |
| B-344 | one individualized compound I | Rimsulfuron |
| B-345 | one individualized compound I | Triflusulfuron |
| B-346 | one individualized compound I | Atrazine |
| B-347 | one individualized compound I | Hexazinone |
| B-348 | one individualized compound I | Diuron |
| B-349 | one individualized compound I | Florasulam |
| B-350 | one individualized compound I | Pyroxasulfone |
| B-351 | one individualized compound I | Bentazone |
| B-352 | one individualized compound I | Cinidon-ethyl |
| B-353 | one individualized compound I | Cinmethylin |
| B-354 | one individualized compound I | Dicamba |
| B-355 | one individualized compound I | Diflufenzopyr |
| B-356 | one individualized compound I | Quinclorac |
| B-357 | one individualized compound I | Quinmerac |
| B-358 | one individualized compound I | Mesotrione |
| B-359 | one individualized compound I | Saflufenacil |
| B-360 | one individualized compound I | Topramezone |
| B-361 | one individualized compound I | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| B-362 | one individualized compound I | [rel-(2S;3R)-3-(2-chlorophenyl)-2-(2,4-difluorophenyl)-oxiranylmethyl]-5-thio-cyanato-1H-[1,2,4]triazole, |
| B-363 | one individualized compound I | 2-[rel-(2S;3R)-3-(2-chlorophenyl)-2-(2,4-difluorophenyl)-oxiranylmethyl]-2H-[1,2,4]triazole-3-thiol |
| B-364 | one individualized compound I | 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone |

TABLE B-continued

Composition comprising one indivivalized compound I and one further active substance from groups A) to O)

| Mixture | Component 1 | Component 2 |
|---|---|---|
| B-365 | one individualized compound I | 2,6-dimethyl-1H,5H-[1,4]dithiino[2,3-c:5,6-c']dipyrrole-1,3,5,7(2H,6H)-tetraone |
| B-366 | one individualized compound I | flupyradifurone |
| B-367 | one individualized compound I | 3-(difluoromethyl)-1-methyl-N-(1,1,3-trimethylindan-4-yl)pyrazole-4-carboxamide |
| B-368 | one individualized compound I | 3-(trifluoromethyl)-1-methyl-N-(1,1,3-trimethylindan-4-yl)pyrazole-4-carboxamide |
| B-369 | one individualized compound I | 1,3-dimethyl-N-(1,1,3-trimethylindan-4-yl)pyrazole-4-carboxamide |
| B-370 | one individualized compound I | 3-(trifluorometh-yl)-1,5-dimethyl-N-(1,1,3-trimethylindan-4-yl)pyrazole-4-carboxamide |
| B-371 | one individualized compound I | 3-(difluoro-methyl)-1,5-dimethyl-N-(1,1,3-trimethylindan-4-yl)pyrazole-4-carboxamide |
| B-372 | one individualized compound I | 1,3,5-tri-methyl-N-(1,1,3-trimethylindan-4-yl)pyrazole-4-carboxamide |

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657).

The mixtures of active substances can be prepared as compositions comprising besides the active ingredients at least one inert ingredient by usual means, e.g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

I. SYNTHESIS EXAMPLES

With due modification of the starting compounds, the procedures shown in the synthesis examples below were used to obtain further compounds I. The resulting compounds, together with physical data, are listed in Table I below.

Example 1

Preparation of 2-[4-(4-chloro-phenoxy)-2-trifluoromethyl-phenyl]-1-[1,2,4]triazol-1-yl-propan-2-ol (compound I-2)

Step 1: 4-Fluoro-2-(trifluoromethyl)-acetophenone (35 g, 170 mmol), 4-chlorophenol (21.8 g, 170 mmol), potassium carbonate (28.1 g, 203 mmol) and DMF (284 g, 300 ml) were stirred together at about 115° C. for about five hours. After cooling, the mixture was added to a brine solution and extracted three times with MTBE. The organic phases were combined, washed twice with 10% aqueous LiCl solution and dried. Evaporation of the solvents gave the intermediate 1-[4-(4-chloro-phenoxy)-2-trifluoromethyl-phenyl]-ethanone (51.4 g, 87%; HPLC $R_t$=3.721 min*(conditions A see below)).

Step 2: DMSO (154 g, 140 ml, 1.97 mol) was added to a mixture of sodium hydride (0.831 g, 33 mmol) in THF (53 g, 6 0 ml) and cooled to about 5° C. Trimethylsulf(ox)onium iodide (6.42 g, 31.5 mmol) in DMSO (80 ml) was then added dropwise and the mixture was stirred at about 5° C. for a further hour. The intermediate 1-[4-(4-chloro-phenoxy)-2-trifluoromethyl-phenyl]-ethanone (5.0 g, 14.3 mol) in DMSO (40 ml) was then added dropwise over a period of about five minutes. The mixture was then stirred for 15 min, quenched with saturated ammonium chloride solution (150 ml) and extracted three times with MTBE. The organic phases were combined, washed with water and dried. Evaporation of the solvent gave 2-[4-(4-chloro-phenoxy)-2-trifluoromethyl-phenyl]-2-methyl-oxirane as a yellow oil (4.4 g, 89%, HPLC $R_t$=3.839 min*(conditions A see below)).

Step 3: A mixture of 2-[4-(4-chloro-phenoxy)-2-trifluoromethyl-phenyl]-2-methyl-oxirane (1.92 g, 4.96 mmol), 1,2,4-triazole (1.715 g, 24.8 mmol), NaOH (0.496 g, 12.41 mmol) and N-methyl pyrrolidone (48 ml) was stirred at about 110° C. for about one hour, followed by further four hours at about 130° C. After cooling to room temperature, saturated ammonium chloride solution was added and the organic phases extracted three times with MTBE. The organic phases were combined, washed twice with 10% LiCl solution and dried. Evaporation of the solvents followed by precipitation from diisopropyl ether gave the final product 2-[4-(4-chloro-phenoxy)-2-trifluoromethyl-phenyl]-1-[1,2,4]triazol-1-yl-propan-2-ol as a white solid (1.55 g, 75%, m.p. 121-122° C., HPLC $R_t$=3.196 min*(conditions A see below)).

Example 1a

Preparation of 2-[4-(4-chloro-phenoxy)-2-trifluoromethyl-phenyl]-1-[1,2,4]triazol-1-yl-propan-2-ol (compound I-2)

Step 1:
4-Fluoro-2-(trifluoromethyl)-acetophenone (622.0 g, 3.02 mol), 4-chlorophenol (426.7 g, 3.32 mol), potassium carbonate (542.1 g, 3.92 mol) and DMF (2365 ml) were stirred together at about 120° C. for about five hours then at 140° C. for 5 hours. After cooling, the mixture was added to a brine solution and extracted three times with MTBE. The organic phases were combined, washed twice with 10% aqueous LiCl solution and dried. Evaporation of the solvents gave the intermediate 1-[4-(4-chloro-phenoxy)-2-trifluoromethyl-phenyl]-ethanone (884.7 g, 88%; $^1$H-NMR (CDCl$_3$; 400 MHz) (ppm)=2.60 (s, 3H); 6.98 (d, 2H); 7.10 (d, 1H); 7.30 (s, 1H); 7.35 (d, 2H); 7.50 (d, 1H).

Step 2:

DMSO (140 mL) was added to a mixture of sodium hydride (0.831 g, 33 mmol) in THF (53 g, 60 mL) and cooled to about 5° C. Trimethylsulfonium iodide (6.42 g, 31.5 mmol) in DMSO (80 ml) was then added dropwise and the mixture was stirred at about 5° C. for a further hour. The intermediate 1-[4-(4-chloro-phenoxy)-2-trifluoromethyl-phenyl]-ethanone (5.0 g, 14.3 mol) in DMSO (40 ml) was then added dropwise over a period of about five minutes. The mixture was then stirred for 15 min, quenched with saturated ammonium chloride solution (150 ml) and extracted three times with MTBE. The organic phases were combined, washed with water and dried. Evaporation of the solvent gave 2-[4-(4-chloro-phenoxy)-2-trifluoromethyl-phenyl]-2-methyl-oxirane as a yellow oil (4.4 g, 89%). $^1$H-NMR (CDCl$_3$; 400 MHz) (ppm)=1,65 (s, 3H); 2.95-3.05 (d, 2H); 6.95 (d, 2H); 7.10 (d, 1H); 7.25 (s, 1H); 7.35 (d, 2H); 7.65 (d, 1H).

Step 3:

A mixture of 2-[4-(4-chloro-phenoxy)-2-trifluoromethyl-phenyl]-2-methyl-oxirane (1.92 g, 4.96 mmol), 1,2,4-triazole (1.715 g, 24.8 mmol), NaOH (0.496 g, 12.41 mmol) and N-methyl pyrrolidone (48 ml) was stirred at about 110° C. for about one hour, followed by further four hours at about 130° C. After cooling to room temperature, saturated ammonium chloride solution was added and the organic phases extracted three times with MTBE. The organic phases were combined, washed twice with 10% LiCl solution and dried. Evaporation of the solvents followed by precipitation from diisopropyl ether gave the final product 2-[4-(4-chloro-phenoxy)-2-trifluoromethyl-phenyl]-1-[1,2,4]triazol-1-yl-propan-2-ol as a white solid (1.55 g, 75%, m.p. 121-122° C., HPLC Rt=3.196 min*(conditions A see below)).

Example 2

Preparation of 2-[4-(4-chloro-phenoxy)-2-trifluoromethyl-phenyl]-1[1,2,4]triazol-1-yl-butan-2-ol (compound I-3)

Step 1: Bromine (29.6 g, 185 mmol) was added dropwise over three minutes to a solution of the 1-[4-(4-chloro-phenoxy)-2-trifluoromethyl-phenyl]ethanone intermediate of step 1 of example 1, (61.4 g, 185 mmol), in diethyl ether (700 ml). The mixture was stirred at room temperature for about 90 min, after which a mixture of ice-cold water (1 l) and saturated sodium bicarbonate solution (300 ml) was added slowly under stirring until pH 7 to 8 was reached. The organic phases were extracted twice with MTBE and washed with LiCl solution. Drying and evaporation of the solvents gave the intermediate 2-bromo-1-[4-(4-chloro-phenoxy)-2-trifluoromethyl-phenyl]-ethanone as a brown oil (76 g, 83%, HPLC R$_t$=3.196 min*(conditions A see below)).

Step 2: 1,2,4-Triazole (3.76 g, 53 mmol) was added slowly and portionwise to a mixture of sodium hydride (1.28 g, 53 mmol) in THF (150 ml), and the mixture stirred at room temperature for about 30 min. To this mixture the intermediate 2-bromo-1-[4-(4-chloro-phenoxy)-2-trifluoromethyl-phenyl]-ethanone (20.0 g, 40.7 mmol) in THF (100 ml) was added dropwise and stirred at room temperature for about 150 min. The reaction mixture was cooled to about 10° C. and added slowly to a mixture of ice-cold water and saturated ammonium chloride solution, and the organic components extracted three times with ethyl acetate. The organic phases were combined, dried and the solvents evaporated. Recrystallisation from diisopropyl ether gave the intermediate 1-[4-(4-chloro-phenoxy)-2-trifluoromethyl-phenyl]-2-[1,2,4]triazol-1-yl-ethanone as a white solid (14.5 g, 84%; HPLC R$_t$=3.225 min*(conditions A see below)).

Step 3: Magnesium bromide diethyl etherate (2.65 g, 10.3 mmol) was added to a solution of 1-[4-(4-chloro-phenoxy)-2-trifluoromethyl-phenyl]-2-[1,2,4]triazol-1-yl-ethanone (2.0 g, 5.1 mmol) in dichloromethane (DCM, 20 ml) and the mixture stirred at room temperature for 90 min. This mixture was then cooled to about −10° C. and ethylmagnesium bromide (10.3 ml of a 1M solution in THF, 10.3 mmol) was added dropwise. After stirring for about two hours, the mixture was allowed to warm to room temperature and was then quenched by addition of a saturated ammonium chloride solution. The organic components were extracted three times with DCM, the organic phases combined, washed again with saturated ammonium chloride solution, dried and the solvents evaporated. Addition of diisopropyl ether resulted in precipitation of the unreacted starting material, which was filtered off. The filtrate was then purified using reverse phase chromatography, to give the final product 2-[4-(4-chloro-phenoxy)-2-trifluoromethyl-phenyl]-1[1,2,4]triazol-1-yl-butan-2-ol as a light brown coloured solid (130 mg, 5.8%; HPLC R$_t$=3.366 min*(conditions A see below); HPLC Rt=1.21 min, masse=412 **(conditions B see below).

Example 3

Preparation of 1-[2-[4-(4-chlorophenoxy)-2-(trifluoromethyl)phenyl]-2-methoxy-propyl]-1,2,4-triazole (compound I-10)

To a solution of 2-[4-(4-chlorophenoxy)-2-(trifluoromethyl)phenyl]-1-(1,2,4-triazol-1-yl)propan-2-ol (33.35 g, 83 mmol) in 400 mL of THF was added sodium hydride (2.54 g, 100.5 mmol) at room temperature. The reaction mixture was then stirred for 30 min followed by the addition of methyliodide (14.24 g, 100.3 mmol) and stirred at 90° C. for 2 hours. After addition of an aq. solution of sodium chloride, the mixture was extracted with dichloromethane, dried, evaporated. The crude residue was purified by recrystallization in heptane/ethyl acetate (1:2) to give the title compound as a colorless solid (34.0 g, 98%; HPLC-MS R$_t$=1.26 min; masse=412 **(conditions B see below)).

Example 4

Preparation of 1-[2-allyloxy-2-[4-(4-chlorophenoxy)-2-(trifluoromethyl)-phenyl]propyl]-1,2,4-triazole (compound I-18)

To a solution of 2-[4-(4-chlorophenoxy)-2-(trifluoromethyl)phenyl]-1-(1,2,4-triazol-1-yl)propan-2-ol (40.0 g, 100.5 mmol) in 500 mL of THF was added sodium hydride (3.05 g, 120.6 mmol) at room temperature. The reaction mixture was then stirred for 30 min followed by the addition of allyl bromide (14.63 g, 120.9 mmol) and stirred at room temperature for 10 hours. After addition of an aq. solution of sodium chloride, the mixture was extracted with dichloromethane, dried, evaporated. The crude residue was purified on silica gel to give the title compound as a yellowish oil (43.5 g, 95%; HPLC-MS $R_f$=1.36 min; masse=438** (conditions B see below)).

Example 5

Preparation of 2-[4-(4-chlorophenoxy)-2-(trifluoromethyl)phenyl]-1-(1,2,4-triazol-1-yl)pent-3-yn-2-ol (compound I-6)

Step 1:
1-Bromo-4-fluoro-2-(trifluoromethyl)benzene (2.04 g, 15.9 mmol) was mixed with potassium carbonate (4.18 g) in dimethylformamide and the reaction mixture heated to 110° C. Then 4-chloro-phenol (3.68 g, 15.14 mmol) was added and the resulting mixture was stirred for 5 hours at 110° C. After cooling and a water/DCM extraction, the organic layers were washed with an aqueous solution of lithium chloride and then sodium hydroxide, dried, filtrated and evaporated to give 3.14 g of 1-bromo-4-(4-chlorophenoxy)-2-(trifluoromethyl)benzene as an oil. $^1$H-NMR (CDCl$_3$; 400 MHz) •• (ppm)=6.80 (d, 1H); 6.95 (d, 2H); 7.35 (d, 2H); 7,55 (d, 1H); 7.80 (s, 1H).

Step 2:
To a solution of 1-bromo-4-(4-chlorophenoxy)-2-(trifluoromethyl)benzene (100.0 g, 0.28 mol, 1.0 eq.) in 500 mL of THF was added dropwise isopropyl magnesium chloride lithium chloride complex (284 mL, 1.3 M in THF) at room temperature and stirred for 2 hours. This mixture was then added dropwise to a solution of acetyl chloride (29.0 g, 0.37 mmol) in 500 mL of THF at room temperature. The resulting reaction mixture was then stirred for 150 min and quenched with a sat. solution of ammonium chloride. After a water/MTBE extraction, the organic solvents were dried and evaporated to give 96.6 g of 1-[4-(4-chlorophenoxy)-2-(trifluoromethyl)-phenyl]ethanone as yellowish oil. $^1$H-NMR (CDCl$_3$; 400 MHz) •• (ppm)=2.6 (s, 3H); 7.0 (d, 2H); 7.10 (d, 1H); 7.30 (s, 1H); 7.37 (d, 2H); 7.50 (d, 1H).

Step 3:
Bromine (29.6 g, 185 mmol) was added dropwise over three minutes to a solution of 1-[4-(4-chloro-phenoxy)-2-trifluoromethyl-phenyl]-ethanone (61.4 g, 185 mmol), in diethyl ether (700 ml). The mixture was stirred at room temperature for about 90 min, after which a mixture of ice-cold water (1 L) and saturated sodium bicarbonate solution (300 ml) was added slowly under stirring until pH 7 to 8 was reached. The organic phases were extracted twice with MTBE and washed with LiCl solution. Drying and evaporation of the solvents gave the intermediate 2-bromo-1[4-(4-chloro-phenoxy)-2-trifluoromethyl-phenyl]-ethanone as a brown oil (76 g, 83%). $^1$H-NMR (CDCl$_3$; 400 MHz) •• (ppm)=4.35 (s, 2H); 7.0 (d, 2H); 7.12 (d, 1H); 7.34 (s, 1H); 7.38 (d, 2H); 7.55 (d, 1H).

Step 4:
1,2,4-Triazole (3.76 g, 53 mmol) was added slowly and portionwise to a mixture of sodium hydride (1.28 g, 53 mmol) in THF (150 ml), and the mixture stirred at room temperature for about 30 min. To this mixture 2-bromo-1-[4-(4-chloro-phenoxy)-2-trifluoromethyl-phenyl]-ethanone (20.0 g, 40.7 mmol) in THF (100 ml) was added dropwise and stirred at room temperature for about 150 min. The reaction mixture was cooled to about 10° C. and added slowly to a mixture of ice-cold water and saturated ammonium chloride solution, and the organic components extracted three times with ethyl acetate. The organic phases were combined, dried and the solvents evaporated. Recrystallization from diisopropyl ether gave the intermediate 1-[4-(4-chloro-phenoxy)-2-trifluoromethyl-phenyl]-2-[1,2,4]triazol-1-yl-ethanone as a white solid (14.5 g, 84%). $^1$H-NMR (CDCl$_3$; 400 MHz) •• (ppm)=5.42 (s, 2H); 7.05 (d, 2H); 7.15 (d, 1H); 7.38 (s, 1H); 7.42 (d, 2H); 7.60 (d, 1H); 8.0 (s, 1H); 8.25 (s, 1H).

Step 5:
1-[4-(4-chlorophenoxy)-2-(trifluoromethyl)phenyl]-2-(1,2,4-triazol-1-yl)ethanone (0.5 g, 1.31 mmol) was dissolved in THF (5.0 mL) with a solution of LaCl$_3$.2LiCl (2.4 mL, 0.6M in THF) and stirred for 30 min at room temperature. The resulting solution was added dropwise to 1-propynyl-magnesium bromide (1.5 mL, 0.5M in THF) at room temperature. After 30 min at room temperature, the resulting mixture was quenched with a 10% aqueous solution of HCl and extracted with MTBE. The organic phase was washed with brine, dried and evaporated to give after purification on reverse phase chromatography 2-[4-(4-chlorophenoxy)-2-(trifluoromethyl)phenyl]-1-(1,2,4-triazol-1-yl)pent-3-yn-2-ol as solid (25 mg, HPLC-MS $R_f$=1.21 min, masse=422**(conditions B see below), m.p=137° C.).

Example 6

Preparation of 1-[2-[4-(4-chlorophenoxy)-2-(trifluoromethyl)phenyl]-2-methoxy-butyl]-1,2,4-triazole (compound I-9)

To a solution of 2-[4-(4-chlorophenoxy)-2-(trifluoromethyl)phenyl]-1-(1,2,4-triazol-1-yl)butan-2-ol (4.0 g, 9.71 mmol) in 20 mL of THF was added sodium hydride (294 mg, 11.64 mmol) at room temperature. The reaction mixture was then stirred for 30 min followed by the addition of methyliodide (1.67 g, 11.78 mmol) and stirred at room temperature for 10 hours. After addition of an aq. solution of sodium chloride, the mixture was extracted with dichloromethane, dried, evaporated. The crude residue was purified by flash chromatography on silica gel to give the title compound as a colorless oil (2.42 g, 54%; HPLC-MS $R_f$=1.32 min; masse=426**(conditions B see below)).

Example 7

Preparation of 2-[4-(4-chlorophenoxy)-2-(trifluoromethyl)phenyl]-3-methyl-1-(1,2,4-triazol-1-yl)butan-2-ol (compound I-7)

Step 1:
To a solution of 1-bromo-4-(4-chlorophenoxy)-2-(trifluoromethyl)benzene (450.0 g, 1.15 mol) in 500 mL of THF was added dropwise to isopropyl magnesium chloride lithium chloride complex (1.152 L, 1.3 M in THF) at room temperature and stirred for 1 hour. The reaction mixture was then added dropwise over 1.5 hours at 10° C. to a solution of isopropyl carbonyl chloride (187.9 g, 1.73 mol), LiCl (3.30 g, 0.08 mol), AlCl$_3$ (4.61 g, 0.03 mol), CuCl (3.42 g, 0.03 mol) in THF (4 L). After 1 hour at room temperature, the resulting mixture was quenched with an aqueous solution of ammonium chloride at 10° C. and extracted with MTBE. The organic phase was washed with an aqueous solution of ammoniac then ammonium chloride, dried and evaporated to give after distillation (b.p.=150-155° C., P=0.25 mbar) 1-[4-(4-chlorophenoxy)-2-(trifluoromethyl)phenyl]-2-methyl-propan-1-one as yellowish oil (227.0 g, 52%). $^1$H-NMR (CDCl$_3$; 400 MHz) •• (ppm)=1.20 (d, 6H); 3.20 (m, 1H); 7.0 (d, 2H); 7.10 (d, 1H); 7.34 (s, 1H); 7.38 (d, 2H); 7.41 (d, 1H).

Step 2:

DMSO (120 ml) was added to a mixture of sodium hydride (4.43 g, 175.24 mmol) in THF (130 ml) and cooled to about 5° C. Trimethylsulfonium iodide (34.97 g, 167.9 mmol) in DMSO (12 ml) was then added dropwise and the mixture was stirred at about 5° C. for a further hour. The intermediate 1-[4-(4-chlorophenoxy)-2-(trifluoromethyl)phenyl]-2-methyl-propan-1-one (25.0 g, 72.9 mmol) in DMSO (60 ml) was then added dropwise over a period of about five minutes. The mixture was then stirred overnight at room temperature, then quenched with saturated ammonium chloride solution and extracted three times with MTBE. The organic phases were combined, washed with an aqueous solution of ammonium chloride, filtrated and dried. Evaporation of the solvent gave after purification on silica gel 2-[4-(4-chlorophenoxy)-2-(trifluoromethyl)phenyl]-2-isopropyl-oxirane as a yellowish oil (24.2 g, 84%, HPLC-MS: $R_t$=1.540 min; masse=356**(conditions B see below)).

Step 3:

To 2-[4-(4-chlorophenoxy)-2-(trifluoromethyl)phenyl]-2-isopropyl-oxirane (173.0 g, 0.41 mol) dissolved in N-methyl-2-pyrrolidon (1 L) was added sodium hydroxide (41.2 g, 1.03 mol) and triazole (145.2 g, 2.06 mol) at room temperature. The mixture was then stirred for 12 hours at 125° C. A solution of ammonium chloride and ice water was then added, the mixture extracted with MTBE and washed with an aqueous solution of lithium chloride. The crude residue was purified by recrystallization (Heptane/MTBE, 1:1) to give 2-[4-(4-chlorophenoxy)-2-(trifluoromethyl)phenyl]-3-methyl-1-(1,2,4-triazol-1-yl)butan-2-ol as a colorless solid (110 g, m.p.=114° C.; HPLC-MS $R_t$=1.27 min; masse=426**(conditions B see below)).

Example 8

Preparation of 1-[2-[4-(4-chlorophenoxy)-2-(trifluoromethyl)phenyl]-2-methoxy-3-methyl-butyl]-1,2,4-triazole (compound I-11)

To a solution of 2-[4-(4-chlorophenoxy)-2-(trifluoromethyl)phenyl]-3-methyl-1-(1,2,4-triazol-1-yl)butan-2-ol (3.0 g, 6.69 mmol) in 15 mL of THF was added sodium hydride (0.24 g, 9.37 mmol) at room temperature. The reaction mixture was then stirred for 30 min followed by the addition of methyliodide (1.33 g, 9.37 mmol) and stirred at room temperature for 10 hours. After addition of an aq. solution of sodium chloride, the mixture was extracted with dichloromethane, dried, evaporated. The crude residue was purified by flash chromatography on silica gel to give the title compound as a yellowish oil (HPLC-MS $R_t$=1.33 min; masse=440**(conditions B see below)).

Example 9

Preparation of 1-[4-(4-chlorophenoxy)-2-(trifluoromethyl)phenyl]-1-cyclopropyl-2-(1,2,4-triazol-1-yl)ethanol (compound I-8)

Step 1:

To a solution of 1-bromo-4-(4-chlorophenoxy)-2-(trifluoromethyl)benzene (70.0 g, 199 mmol, 1.0 eq.) in 700 mL of THF was added dropwise isopropyl magnesium chloride lithium chloride complex (199.1 mL, 1.3 M in THF) at room temperature and stirred for 2 hours. The reaction mixture was then added dropwise to a solution of cyclopropane carbonyl chloride (27.05 g, 258 mmol), LiCl (0.5 g, 11.9 mmol), AlCl$_3$ (0.79 g, 5.9 mmol), CuCl (0.59 g, 5.9 mmol) in THF (700 mL). After 30 min at room temperature, the resulting mixture was quenched with an aqueous solution of ammonium chloride at 10° C. and extracted with MTBE. The organic phase was washed with an aqueous solution of ammoniac, dried and evaporated to give [4-(4-chlorophenoxy)-2-(trifluoromethyl)phenyl]-cyclopropyl-methanone as a brownish oil (66.8 g). $^1$H-NMR (CDCl$_3$; 400 MHz) •• (ppm)=1.10 (m, 2H); 1.30 (m, 2H); 2.32 (m, 1H); 7.0 (d, 2H); 7.15 (d, 1H); 7.32 (s, 1H); 7.37 (d, 2H); 7.60 (d, 1H).

Step 2:

To a solution of sodium hydride (10.77 g, 448 mmol) in THF (750 mL) and dry DMSO (250 mL) was added under argon drop wise at 5° C. a solution of trimethylsulfonium iodide (87.62 g, 429 mmol) in dry DMSO (800 mL). The mixture was stirred 1 hour at 5° C. followed by a dropwise addition of [4-(4-chlorophenoxy)-2-(trifluoromethyl)phenyl]-cyclopropyl-methanone (66.5 g, 195 mmol) in DMSO (500 mL). The resulting mixture was then warmed to room temperature overnight and quenched with an aqueous solution of ammonium chloride and iced water, and then extracted with MTBE. The organic solvents were washed with water, dried and evaporated to give 2-[4-(4-chlorophenoxy)-2-(trifluoromethyl)phenyl]-2-cyclopropyl-oxirane as an oil (66.0 g). $^1$H-NMR (CDCl$_3$; 400 MHz) •• (ppm)=0.38-0.50 (m, 4H); 1.40 (m, 1H); 2.90-3.0 (dd, 2H); 6.90 (d, 2H); 7.15 (d, 1H); 7.29 (s, 1H); 7.35 (d, 2H); 7.50 (d, 1H).

Step 3:

To 2-[4-(4-chlorophenoxy)-2-(trifluoromethyl)phenyl]-2-cyclopropyl-oxirane (866.0 g, 186 mmol) dissolved in N-methyl-2-pyrrolidon (820 mL) was added sodium hydroxide (18.6 g, 465 mmol) and 1,2,4-triazole (64.2 g, 930 mmol) at room temperature. The mixture was then stirred for 12 hours at 125° C. A solution of ammonium chloride and ice water was then added, the mixture extracted with MTBE and washed with an aqueous solution of lithium chloride. The crude residue was purified by flash chromatography on silica gel to give 1-[4-(4-chlorophenoxy)-2-(trifluoromethyl)phenyl]-1-cyclopropyl-2-(1,2,4-triazol-1-yl)ethanol as an oil (64.5 g, HPLC-MS Rt=1.24 min; masse=424**(conditions B see below)).

The compounds I listed in Table I and Table I continued have been prepared in an analogous manner.

TABLE I

| ex.-no. | R | $R^1$ | $R^2$ | $R^3_n$ | $R^4_m$ | HPLC* $R_t$ (min) | m.p. (° C.) |
|---|---|---|---|---|---|---|---|
| I-1 | $CF_3$ | H | H | — | 4-Cl | 3.086 | |
| I-2 | $CF_3$ | $CH_3$ | H | — | 4-Cl | 3.196 | 121-122 |
| I-3 | $CF_3$ | $CH_2CH_3$ | H | — | 4-Cl | 3.366 | |
| I-4 | $CF_3$ | $CH_2CH_2CH_3$ | H | — | 4-Cl | 3.516 | |

TABLE I-continued

| ex.-no. | R | R¹ | R² | R³ₙ | R⁴ₘ | |
|---|---|---|---|---|---|---|
| I-5 | $CF_3$ | C≡CH | H | — | 4-Cl | 3.166 |
| I-6 | $CF_3$ | C≡CCH$_3$ | H | — | 4-Cl | 3.248 |

"—" when referring to $R^3{}_n$ means that n is zero;
"—" when referring to $R^4{}_m$ means that m is zero;
m.p. = melting point.
*(conditions A): HPLC column: RP-18 column (Chromolith Speed ROD from Merck KgaA, Germany), 50 mm × 4.6 mm with Eluent: acetonitrile + 0.1% trifluoroacetic acid (TFA)/water + 0.1% TFA (gradient from 5:95 to 95:5 in 5 min at 40° C., flow of 1.8 ml/min)

| ex.-no. | R | R¹ | R² | R³ₙ | R⁴ₘ | HPLC** R$_t$ (min) |
|---|---|---|---|---|---|---|
| I-7  | $CF_3$ | CH(CH$_3$)$_2$       | H                | — | 4-Cl     | 1.27 |
| I-8  | $CF_3$ | C$_3$H$_5$ (cyclopropyl) | H            | — | 4-Cl     | 1.24 |
| I-9  | $CF_3$ | CH$_2$CH$_3$         | CH$_3$           | — | 4-Cl     | 1.32 |
| I-10 | $CF_3$ | CH$_3$               | CH$_3$           | — | 4-Cl     | 1.26 |
| I-11 | $CF_3$ | CH(CH$_3$)$_2$       | CH$_3$           | — | 4-Cl     | 1.33 |
| I-12 | $CF_3$ | C$_3$H$_5$ (cyclopropyl) | CH$_3$       | — | 4-Cl     | 1.31 |
| I-13 | $CF_3$ | H                    | H                | — | 2,4-Cl$_2$ | 1.17 |
| I-14 | $CF_3$ | H                    | CH$_3$           | — | 4-Cl     | 1.25 |
| I-15 | $CF_3$ | CF$_3$               | H                | — | 4-Cl     | 1.23 |
| I-16 | $CF_3$ | CH$_3$               | H                | — | 4-F      | 1.08 |
| I-17 | $CF_3$ | CH$_3$               | CH$_2$CH$_3$     | — | 4-Cl     | 1.34 |
| I-18 | $CF_3$ | CH$_3$               | CH$_2$CH=CH$_2$  | — | 4-Cl     | 1.36 |
| I-19 | $CF_3$ | C≡CCH$_3$            | CH$_2$CH$_3$     | — | 4-Cl     | 1.38 |
| I-20 | $CF_3$ | C≡CCH$_3$            | CH$_2$C≡CH       | — | 4-Cl     | 1.32 |

"—" when referring to $R^3{}_n$ means that n is zero;
"—" when referring to $R^4{}_m$ means that m is zero;
m.p. = melting point.
**(conditions B): HPLC methode Data for continued Table I:
Mobile Phase: A: Water + 0.1% TFA, B: acetonitrile; Gradient: 5% B to 100% B in 1.5 min; Temperature: 60° C.; MS method: ESI positive; mass area (m/z): 10-700; Flow: 0.8 ml/min to 1.0 ml/min in 1.5 min; Column: Kinetex XB C18 1.7µ 50 × 2.1 mm; Aparatus: Shimadzu Nexera LC-30 LCMS-2020

II. EXAMPLES OF THE ACTION AGAINST HARMFUL FUNGI

The fungicidal action of the compounds of the formula I was demonstrated by the following experiments:

A) Greenhouse Tests

The active substances were formulated separately or together as a stock solution comprising 25 mg of active substance which was made up to 10 ml using a mixture of acetone and/or DMSO and the emulsifier Wettol EM 31 (wetting agent having emulsifying and dispersing action based on ethoxylated alkylphenols) in a volume ratio of solvent/emulsifier of 99 to 1. This solution was then made up to 100 ml using water. This stock solution was diluted with the solvent/emulsifier/water mixture described to the active substance concentration given below.

Use Example 1: Preventative Fungicidal Control of Early Blight on Tomatoes (*Alternaria solani*)

Young seedlings of tomato plants were grown in pots. These plants were sprayed to run-off with an aqueous suspension containing the concentration of active ingredient mentioned in the table below. The next day, the treated plants were inoculated with an aqueous suspension of *Alternaria solani*. Then, the trial plants were immediately transferred to a humid chamber. After 5 days at 20 to 22° C. and a relative humidity close to 100%, the extent of fungal attack on the leaves was visually assessed as % diseased leaf area.

In this test, the plants which had been treated with 150 ppm of the active substance from examples I-2 and I4, respectively, showed an infection of less than or equal to 15% whereas the untreated plants were 90% infected.

Use Example 2: Preventative Control of Grey Mold (*Botrytis cinerea*) on Leaves of Green Pepper Young seedlings of green pepper were grown in pots to the 2 to 3 leaf stage. These were sprayed to run-off with an aqueous suspension containing the concentration of active ingredient or their mixture mentioned in the table below. The next day the treated plants were inoculated with a spore suspension of *Botrytis cinerea* in a 2% aqueous biomalt solution. Then, the trial plants were immediately transferred to a dark, humid chamber. After 5 days at 22 to 24° C. and a relative humidity close to 100% the extent of fungal attack on the leaves was visually assessed as % diseased leaf area. In this test, the plants which had been treated with 150 ppm of the active substance from examples I-2, I-3 and I4, respectively, showed an infection of less than or equal to 15% whereas the untreated plants were 90% infected.

Use Example 3: Preventative Control of Brown Rust on Wheat Caused by *Puccinia recondita*

The first two developed leaves of pot-grown wheat seedling were sprayed to run-off with an aqueous suspension containing the concentration of active ingredient as described below. The next day the plants were inoculated with spores of *Puccinia recondita*. To ensure the success the artificial inoculation, the plants were transferred to a humid chamber without light and a relative humidity of 95 to 99% and 20 to 22° C. for 24 h. Then, the trial plants were cultivated for 6 days in a greenhouse chamber at 22-26° C. and a relative humidity between 65 and 70%. The extent of fungal attack on the leaves was visually assessed as % diseased leaf area. In this test, the plants which had been treated with 150 ppm of the active substance from examples I-2, I-3 and I-4, respectively, showed an infection of less than or equal to 15% whereas the untreated plants were 90% infected.

Use Example 4: Preventative Control of Soy Bean Rust on Soy Beans Caused by *Phakopsora pachyrhizi*

Leaves of pot-grown soy bean seedlings were sprayed to run-off with an aqueous suspension containing the concentration of active ingredient as described below. The plants were allowed to air-dry. The next day the plants were inoculated with spores of *Phakopsora pachyrhizii*. To ensure the success of the artificial inoculation, the plants were transferred to a humid chamber with a relative humidity of about 95% and 23 to 27° C. for 24 h. Thereafter the trial plants were cultivated for 14 days in a greenhouse chamber at 23-27° C. and a relative humidity between 60 and 80%. The extent of fungal attack on the leaves was visually assessed as % diseased leaf area.

In this test, the plants which had been treated with 150 ppm of the active substance from examples I-2, I-3 and I-4, respectively, showed an infection of less than or equal to 15% whereas the untreated plants were 90% infected.

Use Example 5: Preventative Control of Leaf Blotch on Wheat Caused by *Septoria tritici*

The first two developed leaves of pot-grown wheat seedling were sprayed to run-off with an aqueous suspension containing the concentration of active ingredient as described below. The next day the plants were inoculated with a spore suspension in water of *Septoria tritici*. To ensure the success the artificial inoculation, the plants were transferred for 4 days to a humid chamber with a relative humidity of 95 to 99% and 20 to 24° C. Thereafter the plants were cultivated for 4 weeks at a relative humidity of 70%. The extent of fungal attack on the leaves was visually assessed as % diseased leaf area.

In this test, the plants which had been treated with 150 ppm of the active substance from examples I-2, I-3 and I-4, respectively, showed an infection of less than or equal to 15% whereas the untreated plants were 90% infected.

Use Example 6:
Microtest

The active compounds were formulated separately as a stock solution having a concentration of 10000 ppm in dimethyl sulfoxide.

M1. Activity Against Rice Blast *Pyricularia oryzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds. Compounds I-3, I-4 and I-10 showed a growth of 4% or less at 2 ppm.

Green House:
The spray solutions were prepared in several steps:
The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

G1. Preventative Control of Leaf Blotch on Wheat Caused by *Septoria tritici* (Septtr P7)

Leaves of pot-grown wheat seedling were sprayed to run-off with an aqueous suspension of the active compound or their mixture, prepared as described. The plants were allowed to air-dry. Seven days later the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

G2. Preventative Control of Leaf Blotch on Wheat Caused by *Septoria tritici* (Septtr P1)

Leaves of pot-grown wheat seedling were sprayed to run-off with an aqueous suspension of the active compound or their mixture, prepared as described. The plants were allowed to air-dry. The next day the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

| Compound Structure | Growth (%) at 0.5 ppm Pyrior | Disease (%) at 16 ppm Septtr P7 |
| --- | --- | --- |
| prior art J. Agric. Food Chem, Vol 57, No 11, 2009; compound V18 | 82 | 60 |
| according to the invention compound I-2, Table I | 68 | 10 |
| Untreated control | — | 80 |

| Compound | Disease(%) at 150 ppm Septtr P1 |
|---|---|
| prior art EP 0 275 955-compound V6 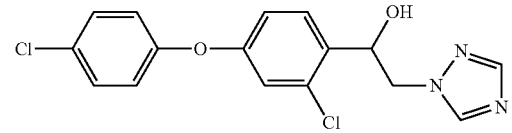 [SMILES: OC(Cn1cncn1)c1ccc(Oc2ccc(Cl)cc2)cc1Cl] | 60 |
| according to the invention compound I-1, Table I | 0 |
| Untreated control | 80 |

Use Example 7:

Microtest

The active compounds were formulated separately as a stock solution having a concentration of 10000 ppm in dimethyl sulfoxide.

M1: Activity Against Rice Blast *Pyricularia oryzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds.

| Compound | Growth (%) at 0.5 ppm Pyrior |
|---|---|
| prior art J. Agric. Food Chem, Vol 57, No 11, 2009; compound V18 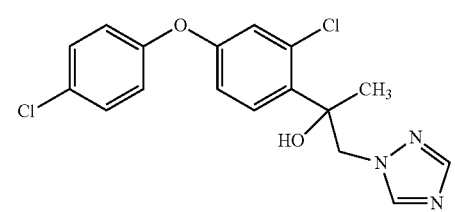 [SMILES: CC(O)(Cn1cncn1)c1ccc(Oc2ccc(Cl)cc2)cc1Cl] | 82 |
| according to the invention compound I-3, Table I | 58 |
| according to the invention compound I-4, Table I | 19 |
| according to the invention compound I-2, Table I | 68 |

| Compound | Growth (%) at 0.5 ppm Pyrior |
|---|---|
| according to the invention compound I-6, Table I | 37 |
| according to the invention compound I-1, Table I | 47 |

Use Example 8:

Green House

The Spray Solutions were Prepared in Several Steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

G1: Preventative Control of Leaf Blotch on Wheat Caused by *Septoria tritici* (Septtr P7)

Leaves of pot-grown wheat seedling were sprayed to run-off with an aqueous suspension of the active compound or their mixture, prepared as described. The plants were allowed to air-dry. Seven days later the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

| Compound | Disease (%) at 16 ppm Septtr P7 |
|---|---|
| prior art J. Agric. Food Chem, Vol 57, No 11, 2009; compound V19 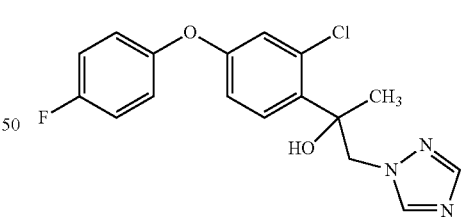 | 60 |
| according to the invention compound I-4, Table I | 25 |
| according to the invention compound I-6, Table I | 0 |
| according to the invention compound I-1, Table I | 2 |
| untreated control | 80 |

Use Example 9:

Green House

The Spray Solutions were Prepared in Several Steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

G1. Preventative Control of Leaf Blotch on Wheat Caused by *Septoria tritici* (Septtr P1)

Leaves of pot-grown wheat seedling were sprayed to run-off with an aqueous suspension of the active compound or their mixture, prepared as described. The plants were allowed to air-dry. The next day the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

| Compound | Disease (%) at 150 pm Septtr P1 |
|---|---|
| prior art DE3801233 compound 2 | 30 |
| according to the invention compound I-14, Table I | 0 |
| prior art J. Agric. Food Chem, Vol 57, No 11, 2009; compound V19 | 40 |
| according to the invention compound I-16, Table I | 0 |
| Untreated control | 90 |

Use Example 10:
Microtest

The active compounds were formulated separately as a stock solution having a concentration of 10000 ppm in dimethyl sulfoxide. The stock solutions were mixed according to the ratio, pipetted onto a micro titer plate (MTP) and diluted with water to the stated concentrations. A spore suspension of the described fungus in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

Fungus

M1. Activity against the grey mold *Botrytis cinerea* in the microtiterplate test (Botrci). Compounds I-13 and I-16 showed a growth of 2% or less at 32 ppm.

M2. Activity against rice blast *Pyricularia oryzae* in the microtiterplate test (Pyrior). Compounds I-13 and I-16 showed a growth of 2% or less at 32 ppm.

M3. Activity against leaf blotch on wheat caused by *Septoria tritici* (Septtr). Compounds I-13 and I-16 showed a growth of 6% or less at 32 ppm.

M4. Activity against early blight caused by *Alternaria solani* (Alteso). Compounds I-13 and I-16 showed a growth of 1% or less at 32 ppm.

M5. Activity against wheat leaf spots caused by *Leptosphaeria nodorum* (Leptno). Compounds I-13 and I-16 showed a growth of 1% or less at 32 ppm.

M6. Activity against net blotch *Pyrenophora teres* on barley in the microtiter test (Pyrnte). Compound I-13 showed a growth of 1% at 32 ppm.

The measured parameters were compared to the growth of the active compound-free control variant (100%) and the fungus-free and active compound-free blank value to determine the relative growth in % of the pathogens in the respective active compounds.

Use Example 11:
Green House
The Spray Solutions were Prepared in Several Steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution was diluted with the described solvent-emulsifier-water mixture to the given concentration.

G1. Preventative Control of Leaf Blotch on Wheat Caused by *Septoria tritici* (Septtr P7)

Leaves of pot-grown wheat seedling were sprayed to run-off with an aqueous suspension of the active compound or their mixture, prepared as described. The plants were allowed to air-dry. Seven days later the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area.

G2. Curative Control of Leaf Blotch on Wheat Caused by *Septoria tritici* (Septtr K7)

Leaves of pot-grown wheat seedling were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. Seven days after inoculation the plants were sprayed to run-off with an aqueous suspension of the active compound or their mixture, prepared as described. Then the plants were transferred back to the chamber with 18-22° C. and a relative humidity close to 70%. After 4 weeks the extent of fungal attack on the leaves was visually assessed as % diseased leaf area.

G3. Control of Powdery Mildew on Grape Caused by *Uncinula necator* (Uncine P3)

Grape cuttings were grown in pots to the 4 to 5 leaf stage. These plants were sprayed to run-off with an aqueous suspension, containing the concentration of active ingredient or their mixture mentioned in the table below. Three days later the treated plants were inoculated with spores of *Uncinula necator* by shaking heavily infestated stock plants over the treated pots. After cultivation in the greenhouse for 10 days at 21-23° C. and a relative humidity between 40 to 70% the extent of fungal attack on the leaves was visually assessed as % diseased leaf area.

G4. Preventative Fungicidal Control of Early Blight on Tomatoes (*Alternaria solani*) (Alteso P7)

Young seedlings of tomato plants were grown in pots. These plants were sprayed to run-off with an aqueous suspension, containing the concentration of active ingredient or mixture mentioned in the table below. Seven days later the treated plants were inoculated with an aqueous suspension of *Alternaria solani*. Then the trial plants were immediately transferred to a humid chamber. After 5 days at 18 to 20° C. and a relative humidity close to 100%, the extent of fungal attack on the leaves was visually assessed as % diseased leaf area.

Comparison was diluted with the described solvent-emulsifier-water mixture to the given concentration.

G1. Protective control of soy bean rust on soy beans caused by *Phakopsora pachyrhizi* (Phakpa P1)

Leaves of pot-grown soy bean seedlings were sprayed to run-off with an aqueous suspension, containing the concentration of active ingredient or their mixture as described below. The plants were allowed to air-dry. The trial plants were cultivated for 1 day in a greenhouse chamber at 23-27° C. and a relative humidity between 60 and 80%. Then the plants were inoculated with spores of *Phakopsora pachyrhizi*. To ensure the success the artificial inoculation, the plants were transferred to a humid chamber with a relative

| Compound | Growth (%) at 0.125 ppm Botrci | Disease (%) at 16 ppm Septtr P7 | Disease (%) at 16 ppm Septtr K7 | Disease (%) at 16 ppm Uncine P3 | Disease (%) at 63 ppm Alteso P7 | Disease (%) at 16 ppm Alteso P7 |
|---|---|---|---|---|---|---|
| prior art J. Agric. Food Chem, Vol 57, No 11, 2009; compound V18 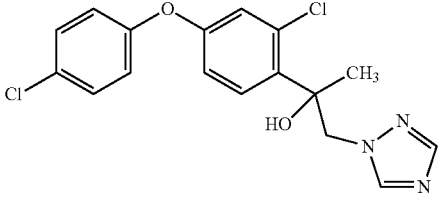 [SMILES: CC(O)(Cn1cncn1)c1ccc(Oc2ccc(Cl)cc2)cc1Cl] | | 67 | | | | 60 |
| according to the invention compound I-2, Table I | | 17 | | | | 15 |
| prior art EP0275955 compound 6 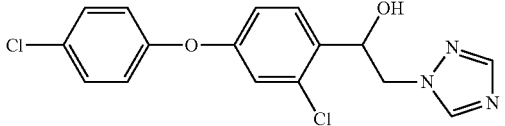 [SMILES: OC(Cn1cncn1)c1ccc(Oc2ccc(Cl)cc2)cc1Cl] | | 30 | 40 | 40 | | |
| according to the invention compound I-1, Table I | | 3 | | 0 | | 3 |
| prior art DE3801233 compound 2 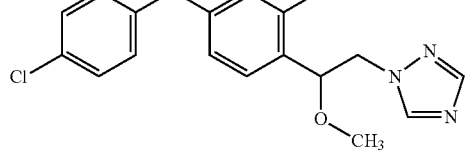 | | 90 | 80 | | | |
| according to the invention compound I-14, Table I | | 15 | 20 | | | |
| Untreated control | — | 90 | 90 | 100 | 100 | 90 |

Use Example 12:

Green House

The Spray Solutions were Prepared in Several Steps:

The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml. This stock solution humidity of about 95% and 20 to 24 C for 24 h. The trial plants were cultivated for fourteen days in a greenhouse chamber at 23-27° C. and a relative humidity between 60 and 80%. The extent of fungal attack on the leaves was visually assessed as % diseased leaf area. In this test, the plants which had been treated with 300 ppm of the active substance from examples I-9, I-12, I-17 and I-18, respectively, showed an infection of less than or equal to 1%, whereas the untreated plants were 80% infected.

G2. Preventative Control of Brown Rust on Wheat Caused by *Puccinia recondita* (Puccrt P1)

The first two developed leaves of pot-grown wheat seedling were sprayed to run-off with an aqueous suspension, containing the concentration of active ingredient or their mixture as described below. The next day the plants were inoculated with spores of *Puccinia recondita*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20-24° C. and a relative humidity between 65 and 70%. The extent of fungal attack on the leaves was visually assessed as % diseased leaf area. In this test, the plants which had been treated with 300 ppm of the active substance from examples I-9, I-11, I-12, I-17, I-18, I-19 and I-20, respectively, showed an infection of less than or equal to 10% whereas the untreated plants were 80% infected.

G3. Preventative Control of Leaf Blotch on Wheat Caused by *Septoria tritici* (Septtr P1)

Leaves of pot-grown wheat seedling were sprayed to run-off with an aqueous suspension of the active compound or their mixture, prepared as described. The plants were allowed to air-dry. At the following day the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area. In this test, the plants which had been treated with 300 ppm of the active substance from examples I-9, I-11, I-12, I-17, I-18, I-19 and I-20, respectively, showed an infection of less than or equal to 7% whereas the untreated plants were 80% infected.

G4. Preventative Fungicidal Control of *Botrytis cinerea* on Leaves of Green Pepper (Botrci P1)

Young seedlings of green pepper were grown in pots to the 4 to 5 leaf stage. These plants were sprayed to run-off with an aqueous suspension, containing the concentration of active ingredient or their mixture mentioned in the table below. The next day the plants were inoculated with a aqueous biomalt solution containing the spore suspension of *Botrytis cinerea*. Then the plants were immediately transferred to a humid chamber. After 5 days at 22 to 24° C. and a relative humidity close to 100% the extent of fungal attack on the leaves was visually assessed as % diseased leaf area. In this test, the plants which had been treated with 300 ppm of the active substance from examples I-9, I-11 and I-18, respectively, showed an infection of less than or equal to 10% whereas the untreated plants were 90% infected.

G5. Preventative Fungicidal Control of Early Blight on Tomatoes (*Alternaria Solani*) (Alteso P1)

Young seedlings of tomato plants were grown in pots. These plants were sprayed to run-off with an aqueous suspension, containing the concentration of active ingredient or mixture mentioned in the table below. The next day, the treated plants were inoculated with an aqueous suspension of *Alternaria solani*. Then the trial plants were immediately transferred to a humid chamber. After 5 days at 18 to 20° C. and a relative humidity close to 100%, the extent of fungal attack on the leaves was visually assessed as % diseased leaf area. In this test, the plants which had been treated with 300 ppm of the active substance from examples I-12, I-17, I-18, I-19 and I-20, respectively, showed an infection of less than or equal to 10% whereas the untreated plants were 90% infected.

We claim:

1. A compound of formula

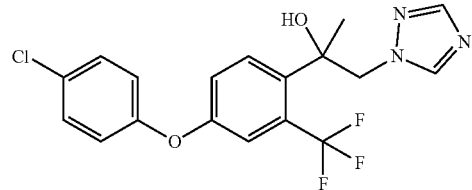 [SMILES: CC(O)(Cn1cncn1)c1ccc(Oc2ccc(Cl)cc2)cc1C(F)(F)F]

or an N-oxide or an agriculturally acceptable salt thereof.

2. An agrochemical composition comprising an auxiliary and the compound of claim 1, the N-oxide or the agriculturally acceptable salt thereof.

3. The composition according to claim 2, comprising an active substance additional to the compound, the N-oxide or the agriculturally acceptable salt thereof.

4. A method for combating phytopathogenic fungi, comprising: treating the fungi or the materials, plants, the soil or seeds to be protected against fungal attack with an effective amount of the compound of claim 1, the N-oxide or the agriculturally acceptable salt thereof.

5. Seed coated with at least one compound of claim 1, the N-oxide or the agriculturally acceptable salt thereof, in an amount of from 0.1 g to 10 kg per 100 kg of seed.

* * * * *